(12) United States Patent
Trottmann et al.

(10) Patent No.: US 6,355,653 B1
(45) Date of Patent: Mar. 12, 2002

(54) AMINO-TRIAZOLOPYRIDINE DERIVATIVES

(75) Inventors: Gerda Huber Trottmann, Grindel; Walter Hunkeler, Magden, both of (CH); Roland Jakob-Roetne, Inzlingen (DE); Gavin John Kilpatrick, Eltisley (GB); Matthias Heinrich Nettekoven, Grenzach-Wyhlen; Claus Riemer, Freiburg, both of (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/645,127

(22) Filed: Aug. 24, 2000

(30) Foreign Application Priority Data

Sep. 6, 1999 (EP) .............................. 99117578

(51) Int. Cl.[7] ................ A61K 31/4439; A61K 31/4433; A61K 31/4436; C07D 401/04; C07D 405/14
(52) U.S. Cl. .................... 514/303; 514/338; 514/339; 514/340; 546/272.4; 546/280.4; 546/282.4; 546/283.4
(58) Field of Search ................. 514/303, 338, 514/339, 340; 546/119, 121, 272.4, 280.4, 282.4, 283.4

(56) References Cited

FOREIGN PATENT DOCUMENTS

| WO | 94/14812 | 7/1994 |
| WO | 99/43678 | 9/1999 |

OTHER PUBLICATIONS

Phadke et al., "A Novel, One–Step Synthesis of [1,2,4] Triazolo[1,5–a]–pyridine Derivatives," Synthesis, vol. 10, pp. 860–862 (1986).*

Bioorganic and Medicinal Chemistry, vol. 6, pp. 619–641 (1998).

(List continued on next page.)

Primary Examiner—T. A. Solola
(74) Attorney, Agent, or Firm—George W. Johnston; Patricia S. Rocha-Tramaloni; Arthur D. Dawson

(57) ABSTRACT

The invention relates to compounds of formula

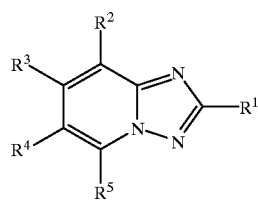

wherein $R^1$ is a 5 or 6 membered heteroaryl group, containing 1 to 3 heteroatoms, selected from N, O or S, and which groups are optionally substituted by one or two substituents, which are lower alkyl, —$(CH_2)_n$OH, halogen or lower alkoxy, and wherein the heteroaryl groups may be optionally linked to the pyrazole ring via an alkylene or alkenyl group, or is phenyl, optionally substituted by one or two substituents being lower alkyl, hydroxy-lower alkyl, halogen, hydroxy or lower alkoxy or is —$O(CH_2)_n$,phenyl, benzofuryl, indolyl or benzothiophenyl, or is —S-lower alkyl;

$R^2$ and $R^4$ are independently from each other hydrogen, cyano or —$S(O)_2$-phenyl;

$R^3$ is hydrogen, halogen or is a 5 or 6 membered heteroaryl group, containing 1 to 3 heteroatoms, selected from N, O or S, and which groups are optionally substituted by one or two substituents, which are lower alkyl, —$(CH_2)_n$-aryl, hydroxy, halogen, lower alkoxy, morpholinyl, amino, lower alkylamino or —$C(O)NR'_2$, and wherein R' is lower alkyl or hydrogen, or is phenyl, optionally substituted by one or two substituents being halogen, lower alkyl, lower alkoxy, amino, di-lower alkyl amino, $CF_3$, —$OCF_3$, —NHC(O)lower alkyl, cyano, —C(O)-lower alkyl, —C(O)O-lower alkyl, —S-lower alkyl, —$S(O)_2$NH-phenyl, —$S(O)_2$-methylpiperazinyl; or is —NR'R", wherein R' and R" are independently from each other hydrogen, —$(CH_2)_n$phenyl, which phenyl ring is optionally substituted by halogen or lower alkoxy, —CH(lower alkyl)-phenyl, indan-1-yl, 1,2,3,4-tetrahydro-naphthalen, or cycloalkyl; or is —O-phenyl, which phenyl ring is optionally substituted by halogen, lower alkyl or lower alkoxy, —O-tetrahydronaphthalenyl or —O—$CH_2$-6-methyl-pyridin-2-yl; or is -benzo[1,3]dioxolyl, -1H-indol-5-yl, naphthyl, benzofuran-2-yl, 1,3,4,9-tetrahydro-b-carbolin-2-yl, piperidin-1-yl, pyrrolidin-1-yl, piperazin-4-yl-methyl or morpholinyl;

$R^5$ is —$NR_2$, wherein R may be the same or different and is hydrogen, lower alkyl, phenyl, benzyl, —CO-lower alkyl, —CO-lower alkoxy, -lower alkenyl, —$CO(CH_2)_n$-phenyl or —$COO(CH_2)_n$-phenyl, wherein the phenyl ring is optionally substituted by $CF_3$, lower alkoxy, halogen or lower alkyl, —$CO(CH_2)_3$-NHCO-lower alkoxy, —$(CH_2)_n$-phenyl, wherein the phenyl ring is optionally substituted by lower alkoxy, $CF_3$ or halogen, or is 4,5-dihydro-1H-imidazol-2-yl-benzoic acid, 1,4,5,6-tetrahydro-pyrimidin-2-yl-benzoic acid or 4,5,6,7-tetrahydro-1H-[1,3]diazepin-2-yl-benzoic acid;

n is 0–4 and their pharmaceutically acceptable salts

84 Claims, No Drawings

OTHER PUBLICATIONS

Bioorganic and Medicinal Chemistry, vol. 6, pp. 707–719 (1998).
J. Med. Chem. (1998) vol. 41, pp. 2835–2845.
J. Med. Chem. (1998) vol. 41, pp. 3186–3201.
J. Med. Chem. (1998) vol. 41, pp. 2126–2133.
J. Med. Chem. (1999) vol. 42, pp. 706–721.
J. Med. Chem. (1996) vol. 39, pp. 1164–1171.
Arch. Pharm. Med. Chem. vol. 332, pp. 39–41, 1999.
Dionisotti, et al. (1997) Br. J. Pharmacol. vol. 121 pp. 353–360.
Baraldi et al., J. Med. Chem., vol. 41, pp. 2126–2133 (1998).
Abstract of WO 99/43678 (Document B2).

* cited by examiner

AMINO-TRIAZOLOPYRIDINE DERIVATIVES

BACKGROUND OF THE INVENTION

The present invention relates to adenosine receptor ligands. Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilises cAMP as a second messenger. The $A_1$ and $A_3$ receptors, coupled with GC proteins inhibit adenylate cyclase, leading to a decrease in cellular cAMP levels, while $A_{2A}$ and $A_{2B}$ receptors couple to $G_S$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identity among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$, with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$-antagonists have therapeutic potential in the treatment of various forms of dementia, for example in Alzheimer's disease and are useful as neuroprotective agents. Adenosine $A_2$-receptor antagonists inhibit the release of dopamine from central synaptic terminals and reduce locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs acting at adenosine receptors therefore have also therapeutic potential as sedatives, muscle relaxants, antipsychotics, anxiolytics, analgesics, respiratory stimulants and antidepressants.

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonize the renal affects of adenosine, have potential as renal protective agents. Furthermore, adenosine $A_3$ and/or $A_{2B}$ antagonists may be useful in the treatment of asthma and other allergic responses.

Numerous documents describe the current knowledge on adenosine receptors, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171, and
Arch. Pharm. Med. Chem., 332, 39–41, (1999).

SUMMARY OF THE INVENTION

The present invention relates to compounds of the formula

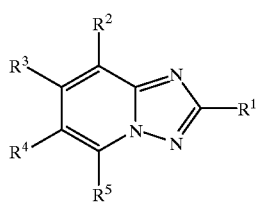

I wherein
- R$^1$ is a 5 or 6 membered heteroaryl group, containing 1 to 3 heteroatoms, selected from N, O or S, and which groups are optionally substituted by one or two substituents,
  - which are lower alkyl, —(CH$_2$)$_n$OH, halogen or lower alkoxy, and wherein the heteroaryl groups may be optionally linked to the pyrazole ring via an alkylene or alkenyl group, or is
  - phenyl, optionally substituted by one or two substituents being lower alkyl, hydroxy-lower alkyl, halogen, hydroxy or lower alkoxy or is
  - —O(CH$_2$)$_n$phenyl, benzofuryl, indolyl or benzothiophenyl, or is —S-lower alkyl;
- R$^2$ and R$^4$ are independently from each other hydrogen, cyano or —S(O)$_2$-phenyl;
- R$^3$ is hydrogen, halogen or is
  - a 5 or 6 membered heteroaryl group, containing 1 to 3 heteroatoms, selected from N, O or S, and which groups are optionally substituted by one or two substituents, which are lower alkyl, —(CH$_2$)$_n$-aryl, hydroxy, halogen, lower alkoxy, morpholinyl, amino, lower alkylamino or —C(O)NR'$_2$, and wherein R' is lower alkyl or hydrogen, or is
  - phenyl, optionally substituted by one or two substituents being halogen, lower alkyl, lower alkoxy, amino, di-lower alkyl amino, CF$_3$, —OCF$_3$, —NHC(O)lower alkyl, cyano, —C(O)-lower alkyl, —C(O)O-lower alkyl, —S-lower alkyl, —S(O)$_2$NH-phenyl, —S(O)$_2$-methylpiperazinyl; or is
  - —NR'R", wherein R' and R" are independently from each other hydrogen, —(CH$_2$)$_n$phenyl, which phenyl ring is optionally substituted by halogen or lower alkoxy, —CH(lower alkyl)-phenyl, indan-1-yl, 1,2,3,4-tetrahydro-naphthalen, or cycloalkyl; or is
  - —O-phenyl, which phenyl ring is optionally substituted by halogen, lower alkyl or lower alkoxy, —O-tetrahydronaphthalenyl or —O—CH$_2$-6-methyl-pyridin-2-yl; or is
  - -benzo [1,3]dioxolyl, -1H-indol-5-yl, naphthyl, benzofuran-2-yl, 1,3,4,9-tetrahydro-b-carbolin-2-yl, piperidin-1-yl, pyrrolidin-1-yl, piperazin-4-yl-methyl or morpholinyl;
- R$^5$ is —NR$_2$, wherein R may be the same or different and is hydrogen, lower alkyl, phenyl, benzyl, —CO-lower alkyl, —CO-lower alkoxy, -lower alkenyl, —CO(CH$_2$)$_n$-phenyl or —COO(CH$_2$)$_n$-phenyl, wherein the phenyl ring is optionally substituted by CF$_3$, lower alkoxy, halogen or lower alkyl, —CO(CH$_2$)$_3$-NHCO-lower alkoxy, —(CH$_2$)$_n$-phenyl, wherein the phenyl ring is optionally substituted by lower alkoxy, CF$_3$ or halogen, or is 4,5-dihydro-1H-imidazol-2-yl-benzoic acid, 1,4,5,6-tetrahydro-pyrimidin-2-yl-benzoic acid or 4,5,6,7-tetrahydro-1H-[1,3]diazepin-2-yl-benzoic acid;
- n is 0–4 and to their pharmaceutically acceptable salts.

It has surprisingly been found that the compounds of formula I are adenosine receptor ligands.

The present invention is directed to compounds of formula I and their pharmaceutically acceptable salts per se and as pharmaceutically active substances, their manufacture, medicaments based on a compound in accordance with the invention and their production as well as the use of compounds of formula I in the control or prevention of illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents. The most preferred indications in accordance with the present invention are those, which base on the A$_{2A}$ receptor antagonistic activity and which include disorders of the central nervous system, for example the treatment or prevention of certain depressive disorders, neuroprotection and Parkinson's disease.

DETAILED DESCRIPTION OF THE INVENTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

As used herein, the term "lower alkenyl" denotes an unsaturated straight- or branched-chain alkyl group containing from 2 to 6 carbon atoms, for example, ethylen, propylen, isopropylen, n-butylen, i-butylen, 2-butylen, t-butylen and the like. Preferred lower alkyl groups are groups with 2–4 carbon atoms.

The term "cycloalkyl" denotes a saturated carbocyclic group, containing 3–6 carbon atoms.

The term "halogen" denotes chlorine, iodine, fluorine and bromine.

The term "lower alkoxy" denotes a group wherein the alkyl residues is as defined above, and which is attached via an oxygen atom.

The term "5 or 6 membered heteroaryl group" denotes, for example furyl, thiophenyl, thiazolyl, pyridinyl, tetrahydrofuranyl, 5,6-dihydro-4H-pyran-2-yl, isoxazol-5-yl, 4,5-dihydro-furan-2-yl, 5,6-dihydro-pyran-2-yl, pyrazol-1-yl, 1,2,4-triazol-1-yl, imidazol-1-yl and the like.

Preferred "aryl" groups are, for example phenyl or naphthyl groups.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Exemplary preferred compounds, showing activity on the A$_{2A}$ receptor, are compounds of formula I, wherein R$^5$ is an unsubstituted amino group and R$^1$ is furyl, for example the following compounds:

- 2-furan-2-yl-7-pyridin-4-yl-[1,2,4]triazolo[1,5-a]pyridin-5-ylamine,
- 2-furan-2-yl-7-pyridin-3-yl-[1,2,4]triazolo[1,5-a]pyridin-5-ylamine,
- 2-furan-2-yl-7-pyridin-2-yl-[1,2,4]triazolo[1,5-al pyridin-5-ylamine,
- 7(3,5-blis-trifluoromethyl-phenyl)-2-furan-2-yl-[1,2,4] triazolo 1,5-a ]pyridin-5-ylamine,
- 7-(3,5-dichloro-phenyl)-2-furan-2-yl-[1,2,4]triazolo[1,5-a]pyridin-5-ylamine,
- 7-(4-chloro-phenyl)-2-furan-2-yl-[1,2,4]triazolo[1,5-a] pyridin-5-ylamine,
- 2-furan-2-yl-7-(2-methyl-pyridin-4-yl)-[1,2,4]triazolo[1,5-a]pyridin-5-ylamine, 7-(2-ethyl-pyridin-4-yl)-2-furan-2-yl-[1,2,4]triazolo[1,5-a]pyridin-5-ylamine,
2-furan-2-yl-7-(2-propyl-pyridin-4-yl)-[1,2,4]triazolo[1,5-a]pyridin-5-ylamine,
2-furan-2-yl-7-(2-isopropyl-pyridin-4-yl)-[1,2,4]triazolo[1,5-a]pyridin-5-ylamine,
7-(4-fluoro-phenyl)-2-furan-2-yl-[1,2,4]triazolo[1,5-a]pyridin-5-ylamine,
2-furan-2-yl-7-(1-oxy-pyridin-4-yl)-[1,2,4]triazolo[1,5-a]pyridin-5-ylamine,
5-amino-2-furan-2-yl-7-pyridin-4-yl-[1,2,4]triazolo[1,5-a]pyridine-6-carobonitrile,
7-(3-amino-phenyl)-2-furan-2-yl-[1,2,4]triazolo[1,5-a]pyridin-5-ylamine,
7-(3,4-dimethoxy-phenyl)-2-furan-2-yl-[1,2,4]triazolo[1,5-a]pyridin-5-ylamine,
7-(3,4-dichloro-phenyl)-2-furan-2-yl-[1,2,4]triazolo[1,5-a]pyridin-5-ylamine,
7-(3-fluoro-phenyl)-2-furan-2-yl-[1,2,4]triazolo[1,5-a]pyridin-5-ylamine,
1-[3-(5-amino-2-furan-2-yl-[1,2,4]triazolo[1,5-a]pyridin-7-yl)-phenyl]-ethanone,
7-(2-fluoro-phenyl)-2-furan-2-yl-[1,2,4]triazolo[1,5-a]pyridin-5-ylamine,
2-furan-2-yl-7-m-tolyl-[1,2,4]triazolo[1,5-a]pyridin-5-ylamine,
2-furan-2-yl-7-(4-methylsulfanyl-phenyl)-[1,2,4]triazolo[1,5-a]pyridin-5-ylamine,
2-furan-2-yl-7-thiophen-3-yl-[1,2,4]triazolo[1,5-a]pyridin-5-ylamine,
2-furan-2-yl-7-(3-trifluoromethyl-phenyl)-[1,2,4]triazolo[1,5-a]pyridin-5-ylamine,
2-furan-2-yl-7-(3-methoxy-phenyl)-[1,2,4]triazolo[1,5-a]pyridin-5-ylamine,
N-[3-(5-amino-2-furan-2-yl-[1,2,4]triazolo[1,5-a]pyridin-7-yl)-phenyl]-acetamide,
2-furan-2-yl-7-(1H-indol-5-yl)-[1,2,4]triazolo[1,5-a]pyridin-5-ylamine,
N-[4-(5-amino-2-furan-2-yl-[1,2,4]triazolo[1,5-a]pyridin-7-yl)-2-methyl-phenyl]-acetamide,
2-furan-2-yl-7-piperidin-1-yl-[1,2,4]triazolo[1,5-a]pyridin-5-ylamine,
2-furan-2-yl-7-pyrrolidin-1-yl-[1,2,4]triazolo[1,5-a]pyridin-5-ylamine,
2-furan-2-yl-7-(4-methyl-piperazin-1-yl)-[1,2,4]triazolo[1,5-a]pyridin-5-ylamine,
N7-(2-chloro-benzyl)-2-furan-2-yl-[1,2,4]triazolo[1,5-a]pyridine-5,7-diamine,
2-furan-2-yl-N7-(2-methoxy-benzyl)-[1,2,4]triazolo[1,5-a]pyridine-5,7-diamine,
2-furan-2-yl-N7-(1-phenyl-ethyl)-[1,2,4]triazolo[1,5-a]pyridine-5,7-diamine,
7-(5-butyl-pyridin-2-yl)-2-furan-2-yl-[1,2,4]triazolo[1,5-a]pyridin-5-ylamine,
7-(2-fluoro-pyridin-4-yl)-2-furan-2-yl-[1,2,4]triazolo[1,5-a]pyridin-5-ylamine,
7-(5-chloro-pyridin-2-yl)-2-furan-2-yl-[1,2,4]triazolo[1,5-a]pyridin-5-ylamine,
2-furan-2-yl-7-(6-methoxy-pyridin-3-yl)-[1,2,4]triazolo[1,5-a]pyridin-5-ylamine.

Further preferred compounds are those, wherein $R^5$ is an unsubstituted amino group and $R^1$ is methyl substituted furyl, for example the following compounds:

7-(4-chloro-phenyl)-2-(5-methyl-furan-2-yl)-[1,2,4]triazolo[1,5-a]pyridin-5-ylamine,
7-(3-methoxy-phenyl)-2-(5-methyl-furan-2-yl)-[1,2,4]triazolo[1,5-a]pyridin-5-ylamine,
7-(3,4-dimethoxy-phenyl)-2-(5-methyl-furan-2-yl)-[1,2,4]triazolo[1,5-a]pyridin-5-ylamine,
N-{3-[5-amino-2-(5-methyl-furan-2-yl)-[1,2,4]triazolo[1,5-a]pyridin-7-yl-phenyl}-acetamide or
N-{4-[5-amino-2-(5-methyl-furan-2-yl)-1,2,4]triazolo[1,5-a]pyridin-7-yl]-phenyl}-acetamide.

Further preferred compounds are those, wherein $R^5$ is an unsubstituted amino group and $R^1$ is pyridin-2-yl, for example the following compounds:

7-(4-fluoro-phenyl)-2-pyridin-2-yl-[1,2,4]triazolo[1,5-a]pyridin-5-ylamine,
7-(3-methoxy-phenyl)-2-pyridin-2-yl-[1,2,4]triazolo[1,5-a]pyridin-5-ylamine,
7-(3-amino-phenyl)-2-pyridin-2-yl-[1,2,4]triazolo[1,5-a]pyridin-5-ylamine,
7-(2-ethyl-pyridin-4-yl)-2-pyridin-2-yl-[1,2,4]triazolo[1,5-a]pyridin-5-ylamine,
7-(2-methyl-pyridin-4-yl)-2-pyridin-2-yl-[1,2,4]triazolo[1,5-a]pyridin-5-ylamine,
7-(5-ethyl-pyridin-2-yl)-2-pyridin-2-yl-[1,2,4]triazolo[1,5-a]pyridin-5-ylamine,
2,7-di-pyridin-2-yl-[1,2,4]triazolo[1,5-a]pyridin-5-ylamine,
7-(5-chloro-pyridin-2-yl)-2-pyridin-2-yl-[1,2,4]triazolo[1,5-a]pyridin-5-ylamine,
7-(6-chloro-pyridin-2-yl)-2-pyridin-2-yl-[1,2,4]triazolo[1,5-a]pyridin-5-ylamine, Preferred compounds are further those, wherein $R^5$ is an unsubstituted amino group and $R^1$ is 4,5-dihydro-furan-2-yl, for example the following compounds:

7-(3,4-dichloro-phenyl)-2-(4,5-dihydro-furan-2-yl)-[1,2,4]triazolo[1,5-a]pyridin-5-ylamine,
2-(4,5-dihydro-furan-2-yl)-7-(3-fluoro-phenyl)-[1,2,4]triazolo[1,5-a]pyridin-5-ylamine,
2-(4,5-dihydro-furan-2-yl)-7-(4-fluoro-phenyl)-[1,2,4]triazolo[1,5-a]pyridin-5-ylamine,
2-(4,5-dihydro-furan-2-yl)-7-m-tolyl-[1,2,4]triazolo[1,5-a]pyridin-5-ylamine or
2-(4,5-dihydro-furan-2-yl)-7-(3-trifluoromethyl-phenyl)-[1,2,4]triazolo[1,5-a]pyridin-5-ylamine.

Preferred compounds are further those, wherein $R^5$ is an unsubstituted amino group and $R^1$ is pyrazol-1-yl, for example the following compound:

2-pyrazol-1-yl-7-pyridin-2-yl-[1,2,4]triazolo[1,5-a]pyridin-5-ylamine.

Exemplary preferred compounds are those, wherein $R^5$ is a substituted amino group, and $R^1$ is phenyl, for example the following compounds:

but-3-enyl-(2-phenyl-7-pyridin-4-yl-[1,2,4]triazolo[1,5-a]pyridin-5-yl)-amine,
ethyl-(2-phenyl-7-pyridin-4-yl-[1,2,4]triazolo[1,5-a]pyridin-5-yl)-amine,
(2-phenyl-7-pyridin-4-yl-[1,2,4]triazolo[1,5-a]pyridin-5-yl)-carbamic acid ethyl ester,
N-(2-phenyl-7-pyridin-4-yl-[1,2,4]triazolo[1,5-a]pyridin-5-yl)-4-trifluoromethyl-benzamide,
2-(2-chloro-phenyl)-N-(2-phenyl-7-pyridin-4-yl-[1,2,4]triazolo[1,5-a]pyridin-5-yl-acetamide,
2-(2,4-dichloro-phenyl)-N-(2-phenyl-7-pyridin-4-yl-[1,2,4]triazolo[1,5-a]pyridin-5-yl)-acetamide, N-(2-phenyl-7-pyridin-4-yl-[1,2,4]triazolo[1,5-a]pyridin-5-yl)-2-(2-trifluoromethyl-phenyl-acetamide, N-(2-phenyl-7-pyridin-4-yl-[1,2,4]triazolo[1,5-a]pyridin-5-yl)-2-(4-trifluoromethyl-phenyl)-acetamide, 3-phenyl-N-(2-phenyl-7-pyridin-4-yl-[1,2,4]triazolo[1,5-a]pyridin-5-yl)-propionamide, N-(2-phenyl-7-pyridin-4-yl-[1,2,4]triazolo[1,5-a]pyridin-5-yl)-2-o-tolyl-acetamide, 2-(2-bromo-phenyl)-N-(2-phenyl-7-pyridin-4-yl-[1,2,4]triazolo[1,5-a]pyridin-5-yl)-acetamide, 2-(2-iodo-phenyl)-N-(2-phenyl-7-pyridin-4-yl-[1,2,4]triazolo [1,5-a]pyridin-5-yl)-acetamide, 3-(2-phenyl-7-pyridin-4-yl-[1,2,4]triazolo[1,5-a]pyridin-5-ylcarbamoyl)-propyl]-carbamic acid tert-butyl ester, 2-(2-chloro-phenyl)-ethyl]-(2-phenyl-7-pyridin-4-yl-[1,2,4]triazolo[1,5-a]pyridin-5-yl)-amine, 2-(2,4-dichloro-phenyl)-ethyl]-(2-phenyl-7-pyridin-4-yl-[1,2,4]triazolo[1,5-a]pyridin-5-yl)-amine, (2-phenyl-7-pyridin-4-yl-[1,2,4]triazolo[1,5-a]pyridin-5-yl)-(4-trifluoromethyl-benzyl)-amine, (3-phenyl-propyl)-(2-phenyl-7-pyridin-4-yl-[1,2,4]triazolo[1,5-a]pyridin-5-yl)-amine or diethyl-(2-phenyl-7-pyridin-4-yl-[1,2,4]triazolo[1,5-a]pyridin-5-yl)-amine.

The present compounds of formula I and their pharmaceutically acceptable salts can be prepared by methods known in the art, for example, by processes described below, which process comprises a) reacting a compound of formula

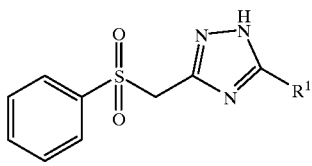

II with a compound of formula

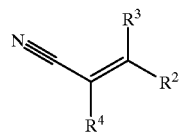

III to a compound of formula

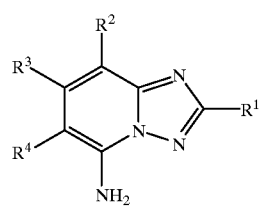

I-1 wherein $R^1$–$R^4$ have the significances given above, or b) substituting one or two hydrogen atoms of the amino group in formula I-1 by R, which is lower alkyl, phenyl, benzyl, —CO-lower alkyl, —CO-lower alkoxy, -lower alkenyl, —CO(CH$_2$)$_n$-phenyl or —COO(CH$_2$)$_n$-phenyl, wherein the phenyl ring is optionally substituted by CF$_3$, lower alkoxy, halogen or lower alkyl, —CO(CH$_2$)$_3$-NHCO-lower alkoxy, —(CH$_2$)$_n$-phenyl, wherein the phenyl ring is optionally substituted by lower alkoxy, CF$_3$ or halogen.

c) reacting a compound of formula

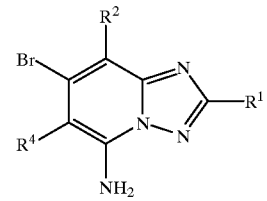

IV with a compound of formula $R^3B(OH)_2$  V to a compound of formula I-1, wherein $R^1$–$R^4$ have the significances given above, or d) modifying one or more substituents $R^1$–$R^5$ within the definitions given above, and if desired, converting the compounds obtained into pharmaceutically acceptable acid addition salts.

In accordance with process variant a) to a boiling suspension of sodiumhydride and THF is added a mixture of compounds of formula II and III, for example 3-benzenesulfonylmethyl-5-furan-2-yl-1H-[1,2,4]triazole and 3-(4-pyridinyl)-2-propenenitrile or 3-benzenesulfonylmethyl-5-furan-2-yl-1H-[1,2,4]triazole and (E)-3-(2-methyl-pyridin-4-yl)-acrylonitril. The reaction is carried out at boiling temperature.

The substitution of one or two hydrogen atoms of the amino group in formula I-1 by R, wherein R has the significance given above, is carried out by conventional methods, for example with corresponding acetyl- or benzoyl chlorides.

A further method for the preparation of compounds of formula I is described in process variant c). In accordance with this method, a mixture of a compound of formula IV, for example 7-bromo-2-phenyl-[1,2,4]pyridin-5-ylamine and of a compound of formula V, for example p-tolyl-boronic acid, is treated with tetrakis-(triphenylphosphine) palladium and heated to about 90° C. The reaction is carried out in the presence of a base, for example in Na$_2$CO$_3$, Cs$_2$CO$_3$ or triethylamine.

The salt formation is effected at room temperatures in accordance with methods which are known per se and which are familiar to any person skilled in the art. Not only salts with inorganic acids, but also salts with organic acids came into consideration. Hydrochlorides, hydrobromides, sulphates, nitrates, citrate, acetates, maleates, succinates, methan-sulphonates, p-toluenesulphonates and the like are examples of such salts.

In Examples 1–351 and in the following schemes 1 and 2 the preparation of compounds of formula I is described in more detail.

The starting materials of formulae III, V, VI, VIII and X are known compounds or maybe prepared according to methods known in the art.

Scheme 1

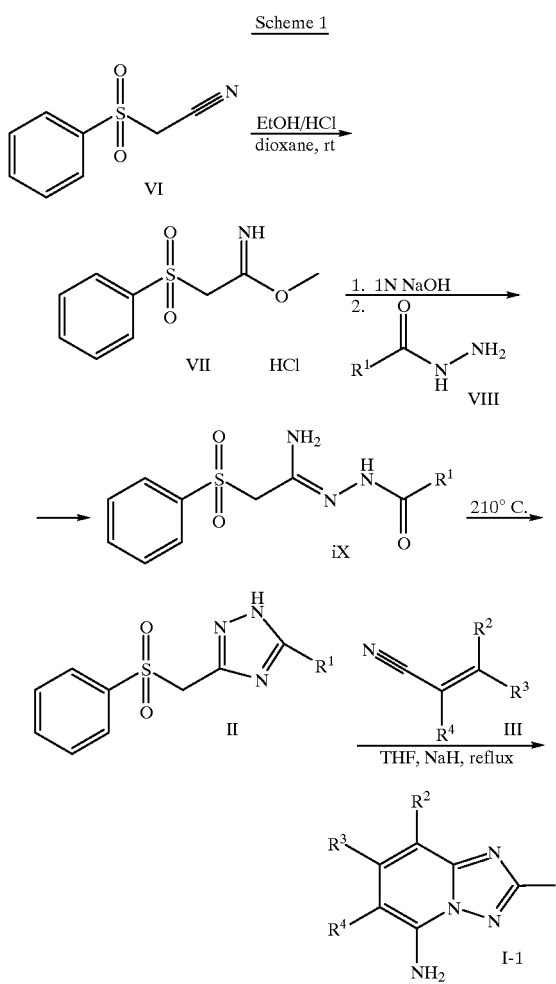

The meaning of the substituents $R^1$–$R^4$ is given above.

Scheme 2

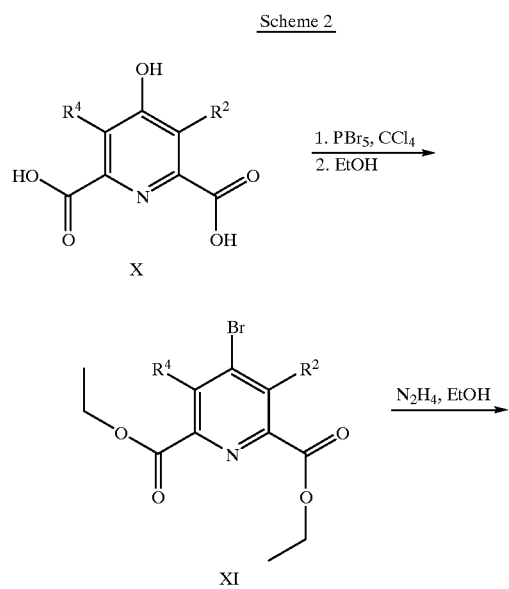

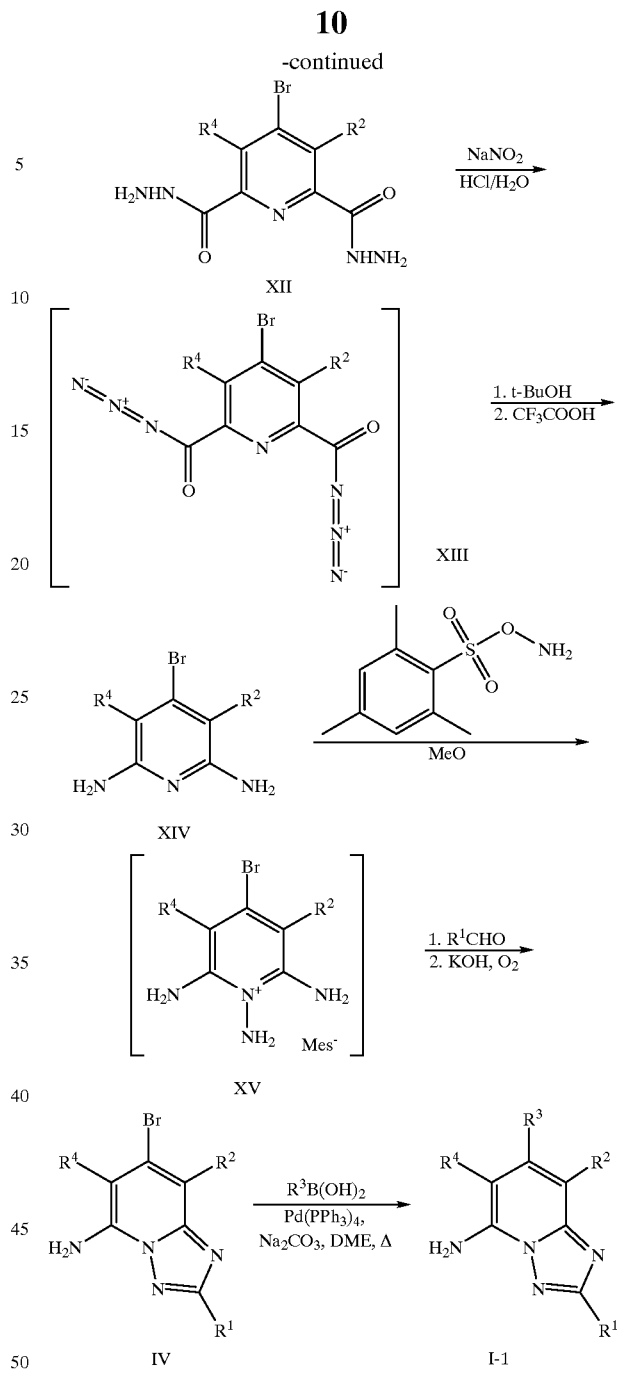

The compounds of formula I and their pharmaceutically usable addition salts possess valuable pharmacological properties. Specifically) it has been found that the compounds of the present invention are adenosine receptor ligands.

The compounds were investigated in accordance with the tests given hereinafter.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 nM KCl, 2 nM CaCl$_2$ and 10 mM MgCl$_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 μg of membrane protein, 0.5 mg of Ysi-poly-1-lysine SPA beads io and 0.1U adenosine deaminase in a final volume of 200 μl of buffer A. Non-specific binding was defined using xanthine amine congener (XAC; 2 μM). Compounds were tested at 10 concentrations from 10 μM–0.3 nM. All assays were conducted in duplicate and repeated at least two times. Assay plates were incubated for 1hour at room temperature before centrifugation and then bound ligand determined using a Packard Topcount scintillation counter. IC$_{50}$ values were calculated using a non-linear curve fitting program and Ki values calculated using the Cheng-Prussoff equation.

In accordance with the invention, it has been shown that compounds of formula I have a high affinity toward the A$_{2A}$ receptor. The preferred compounds have an pKi value in the range of 7.5 to 8.4 in the human A$_{2A}$ binding. In the table below are described some specific pKi values of preferred compounds.

| Compound | hA$_{2A}$pKi |
|---|---|
| 2-(4,5-Dihydro-furan-2-yl)-7-m-tolyl-[1,2,4]triazolo[1,5-a]pyridin-5-ylamine | 7.5 |
| 7-(2-Methyl-pyridin-4-yl)-2-pyridin-2-yl-[1,2,4]triazolo[1,5-a]pyridin-5-ylamine | 7.5 |
| 2-(4,5-Dihydro-furan-2-yl)-7-(3-fluoro-phenyl)-[1,2,4]triazolo[1,5-a]pyridin-5-ylamine | 7.6 |
| 7-(3,4-Dimethoxy-phenyl)-2-furan-2-yl-[,2,4]triazolo[1,5-a]pyridin-5-ylamine | 7.6 |
| 7-(2-Fluoro-pyridin-4-yl)-2-furan-2-yl-[1,2,4]triazolo[1,5-a]pyridin-5-ylamine | 7.8 |
| 2-Furan-2-yl-7-(6-methoxy-pyridin-3-yl)-[1,2,4]triazolo[1,5-a]pyridin-5-ylamine | 7.9 |
| 2-Furan-2-yl-7-m-tolyl-[1,2,4]triazolo[1,5-a]pyridin-5-ylamine | 8.0 |
| 7-(3,4-Dichloro-phenyl)-2-(4,5-dihydro-furan-2-yl)-[1,2,4]triazolo[1,5-a]pyridin-5-ylamine | 8.1 |
| 7-(2-Ethyl-pyridin-4-yl)-2-pyridin-2-yl-[1,2,4]triazolo[1,5-a]pyridin-5-ylamine | 8.1 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

2-Furan-2-yl-7-pyridin-4-yl-[1,2,4]triazolo[1,5-a]pyridin-5-ylamine a) Furan-2-carboxylic acid (1-amino-2-benzenesulfonyl-ethylidene)-hydrazide A suspension of 85.0 g (0.32 mol) 2-(phenylsulfonyl)-ethanimidic acid ethyl ester hydrochloride in 700 ml chloroform was treated with 320 ml 1N aqueous sodium hydoxide. 100 ml of a saturated aqueous sodiumbicarbonate solution was added and the mixture was extracted with chloroform. The extracts were combined and dried with sodium sulfate and the solvents were distilled off under reduced pressure. The resulting colorless oil was stirred together with 42.6 g (0.34 mol) 2-furancarboxylic acid hydrazide in 600 ml chloroform for 24 hours at 50° C. The resulting precipitate was filtered off and dried. A quantitative yield of furan-2-carboxylic acid (1-amino-2-benzenesulfonyl-ethylidene)-hydrazide was obtained as pale crystals, mp. 195° C. (decomposition), MS m/e (%): 308 (M+H$^+$, 100).

b) 3-Benzenesulfonylmethyl-5-furan-2-yl-1H-[1,2,4]triazole 105 g (0.34 mol) Furan-2-carboxylic acid (1-amino-2-benzenesulfonyl-ethylidene)-hydrazide were heated at 200° C. for 20 minutes. The molten mass was then cooled, dissolved in 250 ml hot ethanol and stirred overnight at room temperature. The precipitated crystals were filtered off and dried to yield 65.7 g (66%) 3-benzenesulfonylmethyl-5-furan-2-yl-1H-[1,2,4]triazole as white crystals with mp. 185–186° C., MS m/e (%): 290 (M+H$^+$, 100).

c) 2-Furan-2-yl-7-pyridin-4-yl-[1,2,4]triazolo[1,5-a]pyridin-5-ylamine

To a boiling suspension of 5.9 g(0.12 mol) sodiumhydride (55%) in 100 ml tetrahydrofuran was slowly added over a period of 6 hours a mixture of 10.1 g (0.035 mol) 3-benzenesulfonyl-methyl-5-furan-2-yl-1H-[1,2,4]triazole and 4.56 g (0.035 mol) 3-(4-pyridinyl)-2-propenenitrile in 400 ml tetrahydrofuran. Boiling was continued for 15 hours and then 50 ml methanol were added at room temperature. Evaporation of the solvent and chromatography on silicagel with dichloromethane/methanol 95/5 gave 1.3 g (13%) 2-furan-2-yl-7-pyridin-4-yl-[1,2,4]triazolo [1,5-a]pyridin-5-ylamine as yellow crystals with mp. 294–296° C.

EXAMPLE 2

2-Furan-2-yl-7-pyridin-3-yl-[1,2,4]triazolo[1,5-a]pyridin-5-ylamine

The title compound, MS m/e (%): 277 (M$^+$, 100), was prepared in accordance with the general method of example 1 from 3-benzenesulfonylmethyl-5-furan-2-yl-1H-[1,2,4]triazole and 3-(3-pyridinyl)-2-propenenitrile.

EXAMPLE 3

2-Furan-2-yl-7-pyridin-2-yl-[1,2,4]triazolo[1,5-a]pyridin-5-ylamine

The title compound, MS m/e (%): 278 (M+H$^+$, 100), was prepared in accordance with the general method of example 1 from 3-benzenesulfonylmethyl-5-furan-2-yl-1H-[1,2,4]triazole and 3-(2-pyridinyl)-2-propenenitrile.

EXAMPLE 4

7-(3,5-Bis-trifluoromethyl-phenyl)-2-furan-2-yl-[1,2,4]triazolo[1,5-a]pyridin-5-ylamine The title compound, MS m/e (%): 412 (M$^+$, 100), was prepared in accordance with the general method of example 1 from 3-benzenesulfonylmethyl-5-furan-2-yl-1H-[1,2,4]triazole and 3-[3,5-bis(trifluoromethyl)phenyl]acrylonitrile.

EXAMPLE 5

7-(3,5-Dichloro-phenyl)-2-furan-2-yl-[1,2,4]triazolo[1,5-a]pyridin-5-ylamine a) Mixture of (E)- and (Z)-3-(3,5-dichloro-phenyl)-acrylonitrile To a suspension of 0.68 g (0.024 mol) sodiumhydride in 20 ml tetrahydrofurane and 20 ml dimethylformamide were added 5.79 g (0.017 mol) (cyanomethyl) triphenylphosphonium chloride. After sirring for 1 hour at room temperature a solution of 3.00 g (0.017 mol) 3,5-dichlorobenzaldehyde in 3 ml tetrahydrofuran were added and stirring was continued for 15 hours. Then 2 ml methanol were added, the solvents were evaporated and the residue chromatographed on silicagel with ethylacetate/hexane 2/8 to yield 1.17 g (35%) (E)- and (Z)-3-(3,5-dichloro-phenyl)-acrylonitrile as white crystals. MS m/e (%): 197 (M$^+$, 100).

b) The title compound, mp. 257–260° C. and MS m/e (%): 345 (M+H$^+$, 100), was prepared in accordance with the general method of example 1 from 3-benzenesulfonylmethyl-5-furan-2-yl-1H-[1,2,4]triazole and 3-(3,5-dichloro-phenyl)-acrylonitrile

EXAMPLE 6

7-(4-Chloro-phenyl)-2-furan-2-yl-[1,2,4]triazolo[1,5-a]pyridin-5-ylamine 0.7 g (0.015 mol) sodiumhydride (55%) were added to a solution of 1.50 g (0.005 mol) 3-benzenesulfonylmethyl-5-furan-2-yl-1H-[1,2,4]triazole in 50 ml tetrahydrofuran. The mixture was refluxed and 0.85 g (0.005 mol) 3-(4-chlorophenyl)-2-propenenitrile in 30 ml tetrahydrofuran were added during, aperiod of 5.5 hours. Boiling was continued for 30 minutes and then 20 ml methanol were added at room temperature. Evaporation of the solvent and chromatography on silicagel with dichloromethane/methanol 99/1 gave 0.57 g (35%) 7-(4-chloro-phenyl)-2-furan-2-yl-[1,2,4]triazolo[1,5-a]pyridin-5-ylamine as pale crystals. MS m/e (%): 311 (M+H$^+$, 100).

EXAMPLE 7

2-Furan-2-yl-7-(2-methyl-pyridin-4-yl)-[1,2,4]triazolo[1,5-a]pyridin-5-ylamine

The title compound, mp. 100–101° C. and MS (EI) m/e (%): 291 (M$^+$, 100), was prepared in accordance with the general method of example 1 from 3-benzenesulfonylmethyl-5-furan-2-yl-1H-[1,2,4]triazole and (E)-3-(2-methyl-pyridin-4-yl)-acrylonitrile.

EXAMPLE 8

7-(2-Ethyl-pyridin-4-yl)-2-furan-2-yl-[1,2,4]triazolo[1,5-a]pyridin-5-ylamine a) (E)-3-(2-Ethyl-pyridin-4-yl)-acrylonitrile To a suspension of 1.79 g (0.041 mol) sodiumhydride in 50 ml tetrahydrofurane and 50 ml dimethylformamide were added 13.9 g (0.041 mol) (cyanomethyl)triphenylphosphonium chloride. After sirring for 1 hour at room temperature a solution of 5.54 g (0.041 mol) 2-ethyl-4-pyridinecarboxaldehyde in 10 ml tetrahydrofuran were added and stirring was continued for 15 hours. Then 10 ml methanol were added, the solvents were evaporated and the residue chromatographed on aluminiumoxide with dichloromethane to yield 1.63 g (25%) (E)-3-(2-ethyl-pyridin-4-yl)-acrylonitrile as white waxy solid. MS m/e (%): 158 (M$^+$, 100).

b) The title compound, mp. 184–186° C. and MS m/e (%): 305 (M$^+$, 100), was prepared in accordance with the general method of example 1 from 3-benzenesulfonylmethyl-5-furan-2-yl-1H-[1,2,4]triazole and (E)-3-(2-ethyl-pyridin-4-yl)-acrylonitrile.

EXAMPLE 9

2-Furan-2-yl-7-(2-propyl-pyridin-4-yl)-[1,2,4]triazolo[1,5-a]pyridin-5-ylamine a) 3-(2-Propyl-pyridin-4-yl)-acrylonitrile To a suspension of 1.39 g (0.03 mol) sodiumhydride in 40 ml tetrahydrofurane and 40 ml dimethylformamide were added 10.13 g (0.03 mol) (cyanomethyl)triphenylphosphonium chloride. After sirring for 1 hour at room temperature a solution of 4.48 g (0.03 mol) 2-propyl-4-pyridinecarboxaldehyde in 15 ml tetrahydrofuran were added and stirring was continued for 15 hours. Then 10 ml methanol were added) the solvents were evaporated and the residue chromatographed on aluminiumoxide with dichloromethane to yield 2.42 g 3-(2-propyl-pyridin-4-yl)-acrylonitrile as yellow oil. MS m/e (%): 173 (M+H$^+$, 100).

b) The title compound, MS m/e (%): 319 (M$^+$, 100), was prepared in accordance with the general method of example 1 from 3-benzenesulfonylmethyl-5-furan-2-yl-1H-[1,2,4]triazole and 3-(2-propyl-pyridin-4-yl)-acrylonitrile.

EXAMPLE 10

2-Furan-2-yl-7-(2-isopropyl-pyridin-4-yl)-[1,2,4]triazolo[1,5-a]pyridin-5-ylamine a) 3-(2-Isopropyl-pyridin-4-yl)-acrylonitrile To a suspension of 6.55 g (0.15 mol) sodiumhydride in 220 ml tetrahydrofurane and 220 ml dimethylformamide were added 50.7 g (0.15 mol) (cyanomethyl)triphenylphosphonium chloride. After sirring for 1 hour at room temperature a solution of 22.4 g (0.15 mol) 2-isopropyl-4-pyridinecarboxaldehyde in 50 ml tetrahydrofuran were added and stirring was continued for 15 hours. Then 10 ml methanol were added, the solvents were evaporated and the residue chromatographed on aluminiumoxide with dichloromethane to yield 2.96 g 3-(2-isopropyl-pyridin-4-yl)-acrylonitrile as coorless oil. MS m/e (%): 172 (M$^+$, 100).

b)The title compound, MS m/e (%): 320 (M+H$^+$, 100), was prepared in accordance with the general method of example 1 from 3-benzenesulfonylmethyl-5-furan-2-yl-1H-[1,2,4]triazole and 3-(2-isopropyl-pyridin-4-yl)-acrylonitrile.

EXAMPLE 11

7-(4-Fluoro-phenyl)-2-furan-2-yl-[1,2,4]triazolo[1,5-a]pyridin-5-ylamine

The title compound, MS m/e (%): 295 (M+H$^+$, 100), was prepared in accordance with the general method of example 1 from 3-benzenesulfonylmethyl-5-furan-2-yl-1H-[1,2,4]triazole and 3-(4-fluoro-phenyl)-acrylonitrile.

EXAMPLE 12

2-Furan-2-yl-7-(1-oxy-pyridin-4-yl)-[1,2,4]triazolo[1,5-a]pyridin-5-ylamine a) 3-(1-Oxy-pyridin-4-yl)-acrylonitrile A mixture of 10.4 g (0.08 mol) 3-(4-pyridinyl)-2-propenenitrile, 0.1 g (0.0006 mol) methyltrioxorhenium, 15.5 ml hydrogenperoxide and 300 ml dichloromethane were stirred at room temperature for 6 hours. Then a small quantity of manganese dioxide was added and stirring was continued for one hour. After extraction with dichloromethane/water the organic phase was dried with sodium sulfate and the solvent was distilled off. Chromatography on silicagel with dichloromethane/methanol 95/5 gave 3.3 g (28%) 3-(1-oxy-pyridin-4-y)-acrylonitrile (E:Z= 1:1), MS m/e (%): 146 (M$^+$, 100).

b) 2-Furan-2-yl-7-(1-oxy-pyridin-4-yl)-[1,2,4]triazolo[1,5-a]pyridin-5-ylamine

The title compound, MS m/e (%): 294 (M+H$^+$, 100), was prepared in accordance with the general method of example 1 from 3-benzenesulfonylmethyl-5-furan-2-yl-1H-[1,2,4]triazole and 3-(1-oxy-pyridin-4-yl)-acrylonitrile.

EXAMPLE 13

5-Amino-2-furan-2-yl-7-pyridin-4-yl-[1,2,4]triazolo[1,5-a]pyridine-6-carbonitrile The title compound, MS m/e (%): 303 (M+H$^+$, 100), was prepared in accordance with the general method of example 1 from 3-benzenesulfonylmethyl-5-furan-2-yl-1H-[1,2,4]triazole and 4-pyridinylmethylen-propanedinitril.

EXAMPLE 14

2-(5-Methyl-furan-2-yl)-7-pyridin-4-yl-[1,2,4]triazolo[1,5-a]pyridin-5-ylamine a) 5-Methyl-furan-2-carboxylic acid (1-amino-2-benzenesulfonyl-ethylidene)-hydrazide A suspension of 85.0 g (0.32 mol) 2-(phenylsulfonyl)-ethanimidic acid ethyl ester hydrochloride in 700 ml chloroform was treated with 320 ml 1N aqueous sodium hydroxide. 100 ml of a saturated aqueous sodiumbicarbonate solution was added and the mixture was extracted with chloroform. The extracts were combined and dried with sodium sulfate and the solvents were distilled off under reduced pressure. 17.8 g (0.078 Mol) of the resulting colorless oil was stirred together with 9.15 g (0.065 mol) 5-methyl-furan-2-carboxylic acid hydrazide in 115 ml chloroform for 24 hours at 50° C. The resulting precipitate was filtered off and dried. 17.3 g of 5-methyl-furan-2-carboxylic acid (1-amino-2-benzenesulfonyl-ethylidene)-hydrazide was obtained as white crystals. Mp.: 219–220° C.

b) 3-Benzenesulfonylmethyl-5-methyl-furan-2-yl-1H-[1,2,4]triazole 8.0 g (0.025 mol) 5-Methyl-furan-2-carboxylic acid (1-amino-2-benzenesulfonyl-ethylidene)-hydrazide were heated at 210° C. for 20 minutes. The molten mass was then cooled, dissolved in 250 ml hot ethanol and stirred overnight at room temperature. The precipitated crystals were filtered off and subjected to column chromatography on silicagel with ethyl acetate hexanes 1:1 and 3:2 to yield 6.76 g (90%) 3-benzenesulfonylmethyl-5-methyl-furan-2-yl-1H-[1,2,4] triazole as white crystals.MS (EI) m/e (%): 303 (M+H$^+$, 16).

c) 2-(5-Methyl-furan-2-yl)-7-pyridin-4-yl-[1,2,4]triazolo[1, 5-a]pyridin-5-ylamine The title compound was prepared in accordance with the general method of example 1 from 3-benzenesulfonylmethyl-5-methyl-furan-2-yl-1H-[1,2,4] triazole and 3-(4-pyridinyl)-2-propenenitrile. Mp.: 270–272° C. (dec.).

EXAMPLE 15

N-[2-(5-Methyl-furan-2-yl)-7-pyridin-4-yl-[1,2,4] triazolo[1,5-a]pyridin-5-yl]-acetamide The title compound was obtained as a byproduct in the reaction above and isolated after chromatographic purification on SiO2 with 1% MeOH in dichloromethan. Mp.: 257–259° C.

EXAMPLE 16

2-(4,5-Dimethyl-furan-2-yl)-7-pyridin-4-yl-[1,2,4] triazolo[1,5-a]pyridin-5-ylamine a) 4,5-Dimethyl-furan-2-carboxylic acid (1-amino-2-benzenesulfonyl-ethylidene)-hydrazide A suspension of 1.18 g (0.004 mol) 2-(phenylsulfonyl)-ethanimidic acid ethyl ester hydrochloride in 15 ml chloroform was treated with 6 ml 1N aqueous sodium hydoxide. The mixture was extracted with dichloromethane. The extracts were combined and dried with magnesium sulfate and the solvents were distilled off under reduced pressure. The resulting colorless oil was stirred together with 0.68 g (0.004 mol) 4,5-dimethyl-furan-2-carboxylic acid hydrazide in 10 ml chloroform for 24 hours at reflux temperature. Evaporation of the solvent and chromatography on silicagel with dichloromethane/methanol 19/1 gave 1.14 g (76%) 4,5-dimethyl-furan-2-carboxylic acid (1-amino-2-benzenesulfonyl-ethylidene)-hydrazide as white crystals with mp. 197–199° C., MS m/e (%): 336 (M+H$^+$, 100).

b) 3-Benzenesulfonylmethyl-5-(4,5-dimethyl-furan-2-yl)-1H-[1,2,4]triazole 0.92 g (0.003 mol) 4,5-Dimethyl-furan-2-carboxylic acid (1-amino-2-benzenesulfonyl-ethylidene)-hydrazide were heated at 200° C. for 20 minutes. The molten mass was then cooled and purified by chromatography on silicagel with ethylacetate/hexane 7/3 to yield 0.76 g (83%) 3-benzenesulfonylmethyl-5-(4,5-dimethyl-furan-2-yl)-1H-[1,2,4]triazole as white amorphous powder. MS m/e (%): 318 (M+H$^+$, 100).

c) 2-(4,5-Dimethyl-furan-2-yl)-7-pyridin-4-yl-[1,2,4] triazolo[1,5-a]pyridin-5-ylamine, mp. 275–277° C., MS m/e (%): 306 (M+H$^+$, 100), was prepared in accordance with the general method of example 1 from 3-benzenesulfonylmethyl-5-(4,5-dimethyl-furan-2-yl)-1H-[1,2,4]triazole and 3-(4-pyridinyl)-2-propenenitrile.

EXAMPLE 17

2-Benzofuran-2-yl-7-pyridin-4-yl-[1,2,4]triazolo[1, 5-a]pyridin-5-ylamine a) Benzofuran-2-carboxylic acid (1-amino-2-benzenesulfonyl-ethylidene)-hydrazide 3.4 g (0.0125 Mol) of 2-(phenylsulfonyl)-ethanimidic acid ethyl ester was stirred together with 2.2 g (0.015 mol) benzofuran-2-carboxylic acid hydrazide in 80 ml chloroform for 24 hours at 50° C. The resulting precipitate was filtered off and dried. 2.67 g of benzofuran-2-carboxylic acid (1-amino-2-benzenesulfonyl-ethylidene)-hydrazide was obtained as off-white crystals. Mp.: 205–220° C.

b) 3-Benzenesulfonylmethyl-benzofuran-2-yl-1H-[1,2,4] triazole 2.60 g (0.00727 mol) Benzofuran-2-carboxylic acid (1-amino-2-benzenesulfonyl-ethylidene)-hydrazide were heated at 210° C. for 20 minutes. The molten mass was then cooled, dissolved in 250 ml hot ethanol and stirred overnight at room temperature. The precipitated crystals were filtered off and subjected to column chromatography on SiO-2 with ethyl acetate hexanes 1:1 to yield 2.05 g (83%) 3-benzenesulfonylmethyl-benzofuran-2-yl-1H-[1,2,4] triazole as white crystals, MS (EI) m/e (%): 339 (M$^+$, 24).

c) 2-(Benzofuran-2-yl)-7-pyridin-4-yl-[1,2,41 triazolo[1,5-a]pyridin-5-ylamine

The title compound was prepared in accordance with the general method of example 1 from 3-benzenesulfonylmethyl-benzofuran-2-yl-1H-[1,2,4] triazole and 3-(4-pyridinyl)-2-propenenitrile. Mp.: 270° C. (dec.).

EXAMPLE 18

7-Pyridin-4-yl-2-thiophen-2-yl-[1,2,4]triazolo[1,5-a] pyridin-5-ylamine a) Thiophene-2-carboxylic acid N'-(2-benzenesulfonyl-1-imino-ethyl)-hydrazide A suspension of 13.2 g (0.05 mol) 2-(phenylsulfonyl)-ethanimidic acid ethyl ester hydrochloride in 110 ml chloroform was treated with 50 ml 1N aqueous sodium hydoxide. 20 ml of a saturated aqueous sodiumbicarbonate solution was added and the mixture was extracted with chloroform. The extracts were combined and dried with sodium sulfate and the solvents were distilled off under reduced pressure. The resulting colorless oil was stirred together with 7.82 g (0.05 mol) 2-thiophencarboxylic acid hydrazide in 75 ml chloroform for 24 hours at 50° C. The resulting precipitate was filtered off and dried. A quantitative yield thiophene-2-carboxylic acid N'-(2-benzenesulfonyl-1-imino-ethyl)-hydrazide was obtained as white crystals. MS m/e (%): 324 (M+H$^+$, 100).

b) 3-Benzenesulfonylmethyl-5-thiophen-2-yl-1H-[1,2,4] triazole 1.00, (0.003 mol) Thiophene-2-carboxylic acid N'-(2-benzenesulfonyl-1-imino-ethyl)-hydrazide were heated at 200° C. for 20 minutes. The molten mass Bras then cooled, dissolved in 5 ml hot ethanol and stirred for one hour at room temperature. The precipitated crystals were filtered off and dried to yield 0.87 g (93%) 3-benzenesulfonylmethyl-5-thiophen-2-yl-1H-[1,2,4]triazole as yellow crystals with mp. 191–193° C. MS m/e (%): 305 (M$^+$, 100).

c) 7-Pyridin-4-yl-2-thiophen-2-yl-[1,2,4]triazolo[1,5-a] pyridin-5-ylamine, MS m/e (%): (M$^+$, 100), was prepared in accordance with the general method of example 1 from 3-benzenesulfonylmethyl-5-thiophen-2-yl-1H-[1,2,4] triazole and 3-pyridin-4-)yl-acrylonitrile.

EXAMPLE 19

2-(5-Methyl-thiophen-2-yl)-7-pyridin-4-yl-[1,2,4] triazolo[1,5-a]pyridin-5-ylamine a) 5-Methyl-thiophen-2-carboxylic acid (1-amino-2-benzenesulfonyl-ethylidene)-hydrazide 1.75 g (0.0077 Mol) of 2-(phenylsulfonyl)-ethanimidic acid ethyl ester was stirred together with 1.2 g (0.0077 mol)

5-methyl-thiophen-2-carboxylic acid hydrazide in 14 ml chloroform for 24 hours at 50° C. The resulting precipitate was filtered off and dried. 2.37 g of 5-methyl-thiophen-2-carboxylic acid (1-amino-2-benzenesulfonyl-ethylidene)-hydrazide was obtained as off-white crystals. Mp.: 222° C. (dec.).

b) 3-Benzenesulfonylmethyl-5-methyl-thiophen-2-yl-1H-[1,2,4]triazole 2.33 g (0.0069 mol) 5-Methylthiophen-2-carboxylic acid (1-amino-2-benzenesulfonyl-ethylidene)-hydrazide were heated at 210° C. for 20 minutes. The molten mass was then cooled, dissolved in 250 ml hot ethanol and stirred overnight at room temperature. The precipitated crystals were filtered off and subjected to column chromatography on silicagel with ethyl acetate hexanes 2:1 to yield 2.05 g (92%) 3-benzenesulfonylmethyl-5-methyl-thiophen-2-yl-1H-[1,2,4]triazole as a yellow foam, MS (EI) m/e (%): 319 (M$^+$, 24).

c) 2-(5-Methyl-thiophen-2-yl)-7-pyridin-4-yl-[1,2,4]triazolo 1,5-a]pyridin-5-ylamine The title compound was prepared in accordance with the general method of example 1 from 3-benzenesulfonylmethyl-5-methyl-thiophen-2-yl-1H-[1,2,4]triazole and 3-(4-pyridinyl)-2-propenenitrile. Mp.: 254–256° C. (dec.).

EXAMPLE 20

N-[2-(5-Methyl-thiophen-2-yl)-7-pyridin-4-yl-[1,2,4]triazolo[1,5-a]pyridin-5-yl)-acetamide This compound was obtained as a byproduct in the reaction above as a yellow solid. Mp.: 226–228° C.

EXAMPLE 21

2-Pyridin-2-yl-7-pyridin-4-yl-[1,2,4]triazolo[1,5-a]pyridin-5-ylamine a) Pyridine-2-carboxylic acid (1-amino-2-benzenesulfonyl-ethylidene)-hydrazide A suspension of 9.24 g (0.035 mol) 2-(phenylsulfonyl)-ethanimidic acid ethyl ester hydrochloride in 100 ml chloroform was treated with 35 ml 1N aqueous sodium hydoxide. 14 ml of a saturated aqueous sodiumbicarbonate solution was added and the mixture was extracted with chloroform. The extracts were combined and dried with sodium sulfate and the solvents were distilled off under reduced pressure. The resulting colorless oil was stirred together with 5.12 g (0.037 mol) 2-picolinyl hydrazide in 60 ml chloroform for 24 hours at 50° C. The resulting precipitate was filtered off and dried. A quantitative yield of pyridine-2-carboxylic acid (1-amino-2-benzenesulfonyl-ethylidene)-hydrazide was obtained as white crystals. MS m/e (%): 319 (M+H$^+$, 100).

b) 3-Benzenesulfonylmethyl-5-pyridin-2-yl-1H-[1,2,4]triazole 7.70 g (0.025 mol) Pyridine-2-carboxylic acid (1-amino-2-benzenesulfonyl-ethylidene)-hydrazide were heated at 200° C. for 20 minutes. The molten mass was then cooled, dissolved in 30 ml hot ethanol and stirred for two hous at room temperature. The precipitated crystals were filtered off and dried to yield 6.22 g (84%) 3-benzenesulfonylmethyl-5-pyridin-2-yl-1H-[1,2,4]triazole. MS m/e (%): 300 (M$^+$, 100).

c) 2-Pyridin-2-yl-7-pyridin-4-yl-[1,2,4]triazolo[1,5-a]pyridin-5-ylamine

The 2-pyridin-2-yl-7-pyridin-4-yl-[1,2,4]triazolo[1,5-a]pyridin-5-ylamine, MS m/e (%): 289 (M+H$^+$, 100), was prepared in accordance with the general method of example 1 from 3-benzenesulfonylmethyl-5-pyridin-2-yl-1H-[1,2,4]triazole and 3-pyridin-4-yl-acrylonitrile.

EXAMPLE 22

2-Phenyl-7-pyridin-4-yl-[1,2,4]triazolo[1,5-a]pyridin-5-ylamine a) Benzenecarboxylic acid (1-amino-2-benzenesulfonyl-ethylidene)-hydrazide A suspension of 40.0 g (0.15 mol) 2-(phenylsulfonyl)-ethanimidic acid ethyl ester hydrochloride in 350 ml chloroform was treated with 150 ml 1N aqueous sodium hydoxide. 60 ml of a saturated aqueous sodiumbicarbonate solution was added and the mixture was extracted with chloroform. The extracts were combined and dried with sodium sulfate and the solvents were distilled off under reduced pressure. The resulting colorless oil was stirred together with 22.4 g (0.16 mol) benzhydrazide in 50 ml chloroform for 24 hours at 50° C. The solvent was distilled off and the residue was suspended in 150 ml ethanol and stirred for 5 hours at room temperature. Filtration yielded 44.7 g (93%) of benzenecarboxylic acid (1-amino-2-benzene-sulfonyl-ethylidene)-hydrazide sulfonyl-ethylidene)-hydrazide as white crystals with mp. 209–112° C. MS m/e (%): 318 (M+H$^+$, 100).

b) 3-Benzenesulfonylmethyl-5-phenyl-1H-[1,2,4]triazole 93.1 g (0.29 mol) Benzenecarboxylic acid (1-amino-2-benzenesulfonyl-ethylidene)-hydrazide were heated at 200° C. for 30 minutes. The molten mass was then cooled, dissolved in 500 ml hot ethanol and stirred for 15 hous at room temperature. The precipitated crystals were filtered off and dried to yield 65.6 g (75%) 3-benzenesulfonylmethyl-5-phenyl-1H-[1,2,4]triazole with mp. 141–144° C. MS m/e (%): 299 (M$^+$, 100).

c) 2-Phenyl-7-pyridin-4-yl-[1,2,4]triazolo[1,5-a]pyridin-5-ylamine:

To a boiling suspension of 78.8 g(0.70 mol) potassium tert-butoxide in 400 ml tetrahydrofuran was slowly added over a period of 5 hours a mixture of 70.1 g (0.23 mol) 3-benzenesulfonylmethyl-5-phenyl-1H-[1,2,4]triazole and 30.5 g (0.23 mol) 3-(4-pyridinyl)-2-propenenitrile in 800 ml tetrahydrofuran. Boiling was continued for 18 hours and then the mixture was cooled to room temperature. Evaporation of the solvent and chromatography on silicael with dichloromethane/methanol 95/5 gave 19.8 g (29%) 2-phenyl-7-pyridin-4-yl-[1,2,4]triazolo[1,5-a]pyridin-5-ylamine as yellow crystals with mp. 207–210° C., MS m/e (%):287 (M$^+$, 100).

EXAMPLE 23

2-Phenyl-7-pyridin-2-yl-[1,2,4]triazolo[1,5-a]pyridin-5-ylamine

The title compound, mp. 278–280° C., MS m/e (%): 288 (M+H$^+$, 100), was prepared in accordance with the general method of example 22 from 3-benzenesulfonylmethyl-5-phenyl-1H-[1,2,4]triazole and 3-pyridin-2-yl-acrylonitrile.

EXAMPLE 24

2-Phenyl-7-pyridin-3-yl-[1,2,4]triazolo[1,5-a]pyridin-5-ylamine

The title compound, mp. 201–203° C., MS m/e (%): 288 (M+H$^+$, 100), was prepared in accordance with the general method of example 22 from 3-benzenesulfonylmethyl-5-phenyl-1H-[1,2,4]triazole and 3-pyridin-3-yl-acrylonitrile.

EXAMPLE 25

2,7-Diphenyl-[1,2,4]triazolo[1,5-a]pyridin-5-ylamine

The title compound, mp. 214–216° C., was prepared in accordance with the general method of example 22 from 3-benzenesulfonylmethyl-5-phenyl-1H-[1,2,4]triazole and cinnamonitrile.

EXAMPLE 26

5-Amino-2,7-diphenyl-[1,2,4]triazolo[1,5-a]pyridine-8-carbonitril

A solution of 0.18 g (0.001 mol) 5-phenyl-1H-1,2,4-triazole-3-acetonitrile in 7 ml tetrahydrofuran was treated at −70° C. with 1.56 ml (0.0025 mol) butyllithium (1.6 M in hexane). After one hour 0.21 g (0.001 mol) 3-bromo-3-phenyl-2-propenenitrile was added, stirring was continued for one hour, the mixture warmed to room temperature over night and water was added. Extraction with diethylether, chromatography on silicagel with dichloromethane/methanol 99/1 and crystallisation from diethylether gave 3.6 mg 5-amino-2,7-diphenyl-[1,2,4]triazolo[1,5-a]pyridine-8-carbonitril as white cystals. MS m/e (%): 312 (M+H$^+$, 100).

EXAMPLE 27

But-3-enyl-(2-phenyl-7-pyridin-4-yl-[1,2,4]triazolo[1,5-a]pyridin-5-yl)-amine

A solution of 0.20 g (0.0007 mol) 2-phenyl-7-pyridin-4-yl-[1,2,4]triazolo[1,5-a]pyridin-5-ylamine in 17.5 ml dimethylsulfoxide was treated with 0.69 g (0.001 mol) potassiumhydroxide(85%) for 20 minutes at room temperature. Then 0.10 g(0.0007 mol) 4-bromo-1-butene were added and stirring was continued for 40 hours. Saturated aqueous sodiumbicarbonate was added and the mixture was extracted with ethylacetate. Evaporation of the solvent and chromatography on silicagel with dichloromethane/methanol 97/3 gave 0.04 g(17%) but-3-enyl-(2-phenyl-7-pyridin-4-yl-[1,2,4]triazolo[1,5-a]pyridin-5-yl)-amine as beige crystals. MS m/e (%): 341 (M$^+$, 21), 300 (100), 287 (65).

EXAMPLE 28

Ethyl-(2-phenyl-7-pyridin-4-yl-[1,2,4]triazolo[1,5-a]pyridin-5-yl)-amine

A solution of 0.29 g (0.001 mol) 2-phenyl-7-pyridin-4-yl-[1,2,4]triazolo[1,5-a]pyridin-5-ylamine in 50 ml dimethylformamide was treated with 0.05 g (0.001 mol) sodiumhydride(55%) for 15 minutes at room temperature. Then 0.22 g (0.001 mol) ethyl-p-toluenesulfonate were added and stirring was continued for 22 hours. Saturated aqueous sodiumbicarbonate was added and the mixture was extracted with dichloromethane. Evaporation of the solvent and chromatography on silicagel with dichloromethane/methanol 96/4 gave 0.37 g(17%) ethyl-(2-phenyl-7-pyridin-4-yl-[1,2,4]triazolo[1,5-a]pyridin-5-yl)-amine as beige crystals. MS m/e (%): 316 (M+H$^+$, 100).

EXAMPLE 29

(2-Phenyl-7-pyridin-4yl-[1,2,4]triazolo[1,5-a]pyridin-5-yl)-carbamic acid ethyl ester The title compound, MS m/e (%): 360 (M+H$^+$, 100), was prepared in accordance with the general method of example 27 from 2-phenyl-7-pyridin-4-yl-[1,2,4]triazolo[1,5-a]pyridin-5-ylamine and ethyl chloroformate.

EXAMPLE 30

N-(2-Phenyl-7-pyridin-4-yl-[1,2,4]triazolo[1,5-a]pyridin-5-yl)-4-trifluoromethyl-benzamide A mixture of 0.29 g (0.001 mol) 2-phenyl-7-pyridin-4-yl-[1,2,4]triazolo[1,5-a]pyridin-5-ylamine and 1.13 ml(0.014 mol) pyridine in 30 ml dichloromethane was stirred with 0.63 g(0.003 mol) p-trifluoromethyl benzoyl chloride for 18 hours at room temperature. Then another 0.63 g(0.003 mol) p-trifluoromethyl benzoyl chloride were added and stirring was continued at reflux temperature for 48 hours. After extraction with aqueous sodium hydroxide the organic solvents were distilled off and the residue was recrystallised from methanol to yield 0.28 g(60%) N-(2-phenyl-7-pyridin-4-yl-[1,2,4]triazolo[1,5-a]pyridin-5-yl)-4-trifluoromethyl-benzamide as white crystals. MS m/e (%): 460 (M+H$^+$, 100).

EXAMPLE 31

2-(2-Methoxy-phenyl)-N-(2-phenyl-7-pyridin-4-yl-[1,2,4]triazolo[1,5-a]pyridin-5-yl)-acetamide A mixture of 0.29 g (0.001 mol) 2-phenyl-7-pyridin-4-yl-[1,2,4]triazolo[1,5-a]pyridin-ylamine and 1.13 ml(0.014 mol) pyridine in 30 ml dichloromethane was stirred with 0.55 g(0.003 mol) 3-methoxyphenylacetyl chloride for 18 hours at room temperature. After extraction with aqueous sodium hydroxide the organic solvents were distilled off and the residue was purified by chromatography on silicagel with dichloromethane/methanol 98/2 and crystallisation from methanol to yield 0.25 g(56%) 2-(2-methoxy-phenyl)-N-(2-phenyl- 7-pyridin-4-yl-[1,2,4]triazolo[1,5-a]pyridin-5-yl)-acetamide as beige crystals. MS m/e (%): 436 (M+H$^{30}$, 100).

EXAMPLE 32

2-(2-Chloro-phenyl)-N-(2-phenyl-7-pyridin-4-yl-[1,2,4]triazolo[1,5-a]pyridin-5-yl)-acetamide The title compound, MS m/e (%): 440 (M+H$^+$, 100), was prepared in accordance with the general method of example 31 from 2-phenyl-7-pyridin-4-yl-[1,2,4]triazolo[1,5-a]pyridin-5-ylamine and 2-chlorophenylacetyl chloride.

EXAMPLE 33

2-(2,4-Dichloro-phenyl)-N-(2-phenyl-7-pyridin-4-yl-[1,2,4]triazolo[1,5-a]pyridin-5-yl)-acetamide The title compound, MS m/e (%): 474 (M+H$^+$, 100), was prepared in accordance with the general method of example 31 from 2-phenyl-7-pyridin-4-yl-[1,2,4]triazolo[1,5-a]pyridin-5-ylamine and 2,4-dichlorophenylacetyl chloride.

EXAMPLE 34

2-(3-Chloro-phenyl)-N-(2-phenyl-7-pyridin-4-yl-[1,2,4]triazolo[1,5-a]pyridin-5-yl)-acetamide The title compound, MS m/e (%): 440 (M+H$^+$, 100), was prepared in accordance with the general method of example 31 from 2-phenyl-7-pyridin-4-yl-[1,2,4]triazolo[1,5-a]pyridin-5-ylamine and 3-chlorophenylacetyl chloride.

EXAMPLE 35

2-(3-Fluoro-phenyl)-N-(2-phenyl-7-pyridin-4-yl-[1,2,4]triazolo[1,5-a]pyridin-5-yl)-acetamide The title compound, MS m/e (%): 424 (M+H$^+$, 100), was prepared in accordance with the general method of example 31 from 2-phenyl-7-pyridin-4-yl-1,2,4]triazolo[1,5-a]pyridin-5-ylamine and 3-fluorophenylacetyl chloride.

EXAMPLE 36

N-(2-Phenyl-7-pyridin-4-yl-[1,2,4]triazolo[1,5-a]pyridin-5-yl)-2-(2-trifluoromethyl-phenyl-acetamide The title compound, MS m/e (%): 474 (M+H$^+$, 100), was prepared in accordance with the general method of example 31 from 2-phenyl-7-pyridin-4-yl-[1,2,4]triazolo[1,5-a]pyridin-5-ylamine and 2-(trifluoromethyl)phenylacetyl chloride.

EXAMPLE 37

N-(2-Phenyl-7-pyridin-4-yl-[1,2,4]triazolo[1,5-a]pyridin-5-yl)-2-(3-trifluoromethyl-phenyl-acetamide The title compound, MS m/e (%): 474 (M+H$^+$, 100), was prepared in accordance with the general method of example 31 from 2-phenyl-7-pyridin-4-yl-[1,2,4]triazolo[1,5-a]pyridin-5-ylamine and 3-(trifluoromethyl)phenylacetyl chloride.

EXAMPLE 38

N-(2-Phenyl-7-pyridin-4-yl-[1,2,4]triazolo[1,5-a]pyridin-5-yl)-2-(4-trifluoromethyl-phenyl-acetamide The title compound, MS m/e (%): 474 (M+H$^+$, 100), was prepared in accordance with the general method of example 31 from 2-phenyl-7-pyridin-4-yl-[1,2,4]triazolo[1,5-a]pyridin-5-ylamine and 4-(trifluoromethyl)phenylacetyl chloride.

EXAMPLE 39

3-Phenyl-N-(2-phenyl-7-pyridin-4-yl-[1,2,4]triazolo[1,5-a]pyridin-5-yl)-propionamide The title compound, MS m/e (%): 420 (M+H$^+$, 100), was prepared in accordance with the general method of example 31 from 2-phenyl-7-pyridin-4-yl-[1,2,4]triazolo[1,5-a]pyridin-5-ylamine and phenylpropionyl chloride.

EXAMPLE 40

(2-Phenyl-7-pyridin-4-yl-[1,2,4]triazolo[1,5-a]pyridin-5-yl)-carbamic acid phenyl ester The title compound, MS m/e (%): 408 (M+H$^+$, 100), was prepared in accordance with the general method of example 31 from 2-phenyl-7-pyridin-4-yl-[1,2,4]triazolo[1,5-a]pyridin-5-ylamine and phenyl chloroformate.

EXAMPLE 41

2-Phenyl-N-(2-phenyl-7-pyridin-4-yl-[1,2,4]triazolo[1,5-a]pyridin-5-yl)-acetamide The title compound, MS m/e (%): 406 (M+H$^+$, 100), was prepared in accordance with the general method of example 31 from 2-phenyl-7-pyridin-4-yl-[1,2,4]triazolo[1,5-a]pyridin-5-ylamine and phenylacetyl chloride.

EXAMPLE 42

N-(2-Phenyl-7-pyridin-4-yl-[1,2,4]triazolo[1,5-a]pyridin-5-yl)-benzamide

The title compound, MS m/e (%): 391 (M$^+$, 100), was prepared in accordance with the general method of example 31 from 2-phenyl-7-pyridin-4-yl-[1,2,4]triazolo[1,5-a]pyridin-5-ylamine and benzoylchloride.

EXAMPLE 43

N-(2-Phenyl-7-pyridin-4-yl-[1,2,4]triazolo[1,5-a]pyridin-5-yl)-acetamide

The title compound, MS m/e (%): 330 (M+H$^+$, 100), was prepared in accordance with the general method of example 31 from 2-phenyl-7-pyridin-4-yl-[1,2,4]triazolo[1,5-a]pyridin-5-ylamine and acetylchloride.

EXAMPLE 44

N-(2-Phenyl-7-pyridin-4-yl-[1,2,4]triazolo[1,5-a]pyridin-5-yl)-2-o-tolyl-acetamide The title compound, MS m/e (%): 420 (M+H$^+$, 100), was prepared in accordance with the general method of example 31 from 2-phenyl-7-pyridin-4-yl-[1,2,4]triazolo[1,5-a]pyridin ylamine and o-tolylacetyl chloride.

EXAMPLE 45

2-(2-Bromo-phenyl)-N-(2-phenyl-7-pyridin-4-yl-[1,2,4]triazolo[1,5-a]pyridin-5-yl)-acetamide The title compound, MS m/e (%): 484,486 (M+H$^+$, 100), was prepared in accordance with the general method of example 31 from 2-phenyl-7-pyridin-4-yl-[1,2,4]triazolo[1,5-a]pyridin-5-ylamine and o-bromphenylacetyl chloride.

EXAMPLE 46

2-(2-Iodo-phenyl)-N-(2-phenyl-7-pyridin-4-yl-[1,2,4]triazolo[1,5-a]pyridin-5-yl)-acetamide The title compound, MS m/e (%): 532 (M+H$^+$, 100), was prepared in accordance with the general method of example 31 from 2-phenyl-7-pyridin-4-yl-[1,2,4]triazolo[1,5-a]pyridin-5-ylamine and o-iodophenylacetyl chloride.

EXAMPLE 47

3-(2-Phenyl-7-pyridin-4-yl-[1,2,4]triazolo[1,5-a]pyridin-5-ylcarbamoyl)-propyl]-carbamic acid tert-butyl ester A solution of 0.82 g (0.004 mol) Boc-4 aminobutyric acid and 0.66 g (0.004 mol) 1,1-carbonyl-diimidazole in 70 ml tetrahydrofuran was stirred at room temperature for one hour and was then added at room temperature to a suspension of 0.29 g (0.001 mol) 2-phenyl-7-pyridin-4-yl-[1,2,4]triazolo[1,5-a]pyridin-5-ylamine and 0.10 g (0.002 mol) sodiumhydride(55%) in 50 ml dimethylformamide. After stirring at 80° C. for 20 hours another 0.10 mg (0.002 mol) sodium hydride(55%) and 0.82 g (0.004 mol) Boc-4 aminobutyric acid were added and stirring was continued for 20 hours at 80° C. The solvent was evaporated, the residue taken up with saturated aqueous sodiumbicarbonate. Extraction with dichloromethane and chromatography on silicagel with dichloromethane/methanol gave 0.02 g (5%) [3-(2-phenyl-7-pyridin-4-yl-[1,2,4]triazolo[1,5-a]pyridin-5-ylcarbamoyl)-propyl]-carbamic acid tert-butyl ester. MS m/e (%): 473 (M+H$^+$, 100).

EXAMPLE 48

[2-(2-Methoxy-phenyl)-ethyl](2-phenyl-7-pyridin-4-yl-[1,2,4]triazolo[1,5-a]pyridin-5-yl-amine To 10 ml of a 1 molar solution of lithiumborohydride in tetrahydrofuran were added 2.17 g (0.02 mol) trimethylchlorosilane. After stirring for one hour at room temperature the suspension was added dropwise to a suspension of 0.11 g (0.25 mol) 2-(2-methoxy-phenyl)-N-(2-phenyl-7-pyridin-4-yl-[1,2,4]triazolo[1,5-a]pyridin-5-yl)-acetamide and the mixture heated for 18 hours at 50° C. Then 5 ml methanol were slowly added, the solvents were distilled off and the residue taken up in ethylacetate. The solution was washed with aqueous sodiumhydroxide and with water, dried with sodiumsulfate and evaporated. Recrystallisation from ethanol yielded 0.10 g (94%) [2-(2-methoxy-phenyl)-ethyl]-(2-phenyl-7-pyridin-4-yl-[1,2,4]triazolo[1,5-a]pyridin-5-yl)-amine as beige crystals. MS m/e(%):422 (M+H$^+$, 100).

EXAMPLE 49

(2-Phenyl-7-pyridin-4-yl-[1,2,4]triazolo[1,5-a]pyridin-5-yl)-[2-(3-trifluoromethyl-phenyl)-ethyl]-amine The title compound, MS m/e (%): 460 (M+H$^+$, 100), was prepared in accordance with the general method of example 48 from N-(2-Phenyl-7-pyridin-4-yl-[1,2,4]triazolo[1,5-a]pyridin-5-yl)-2-(3-trifluoromethyl-phenyl)-acetamide.

EXAMPLE 50

2-(2-Chloro-phenyl)-ethyl]-(2-phenyl-7-pyridin-4-yl-[1,2,4]triazolo[1,5-a]pyridin-5-yl)-amine The title compound, MS m/e (%): 426 (M+H$^+$, 100), was prepared in accordance with the general method of example 48 from 2-(2-Chloro-phenyl)-N-(2-phenyl-7-pyridin-4-yl-[1,2,4]triazolo[1,5-a]pyridin-5-yl)-acetamide.

EXAMPLE 51

2-(2,4-Dichloro-phenyl)-ethyl ]-(2-phenyl-7-pyridin-4-yl-[1,2,4]triazolo[1,5-a]pyridin-5-yl)-amine The title compound, MS m/e (%): 460 (M+H$^+$, 100), was prepared in accordance with the general method of example 48 from 2-(2,4-dichloro-phenyl)-N-(2-phenyl-7-pyridin-4-yl-[1,2,4]triazolo[1,5-a]pyridin-5-yl)-acetamide.

EXAMPLE 52

2-(3-Chloro-phenyl)-ethyl]-(2-phenyl-7-pyridin-4-yl-[1,2,4]triazolo[1,5-a]pyridin-5-yl)-amine The title compound, MS m/e (%): 426 (M+H$^+$, 100), was prepared in accordance with the general method of example 48 from 2-(3-chloro-phenyl)-N-(2-phenyl-7-pyridin-4-yl-[1,2,4]triazolo[1,5-a]pyridin-5-yl)-acetamide.

EXAMPLE 53

(2-Phenyl-7-pyridin-4yl-[1,2,4]triazolo[1,5-a]pyridin-5-yl)-(4-trifluoromethyl-benzyl)-amine The title compound, MS m/e (%): 446(M+H$^+$, 100), was prepared in accordance with the general method of example 48 from N-(2-phenyl-7-pyridin-4-yl-[1,2,4]triazolo[1,5-a]pyridin-5-yl)-4-trifluoromethyl-benzamide.

EXAMPLE 54

2-(3-Fluoro-phenyl)-ethyl]-(2-phenyl-7-pyridin-4-yl-[1,2,4]triazolo[1,5-a]pyridin-5-yl)-amine The title compound, MS m/e (%): 410 (M+H$^+$, 100), was prepared in accordance with the general method of example 48 from 2-(3-fluoro-phenyl)-N-(2-phenyl-7-pyridin-4-yl-[1,2,4]triazolo[1,5-a]pyridin-5-yl)-acetamide.

EXAMPLE 55

(2-Phenyl-7-pyridin-4-yl-[1,2,4]triazolo[1,5-a]pyridin-5-yl)-[2-(2-trifluoromethyl-phenyl-ethyl]-amine The title compound, MS m/e (%): 460(M+H$^+$, 100), was prepared in accordance with the general method of example 48 from N-(2-phenyl-7-pyridin-4-yl-[1,2,4]triazolo[1,5-a]pyridin-5-yl)-2-(2-trifluoromethyl-phenyl)-acetamide.

EXAMPLE 56

(2-Phenyl-7-pyridin-4-yl-[1,2,4]triazolo[1,5-a]pyridin-5-yl)-[2-(4-trifluoromethyl-phenyl)-ethyl]-amine The title compound, MS m/e (%): 460 (M+H$^+$, 100), was prepared in accordance with the general method of example 48 from N-(2-phenyl-7-pyridin-4-yl-[1,2,4]triazolo[1,5-a]pyridin-5-yl)-2-(4-trifluoromethyl-phenyl)-acetamide.

EXAMPLE 57

(3-Phenyl-propyl)-(2-phenyl-7-pyridin-4-yl-[1,2,4]triazolo[1,5-a]pyridin-5-yl)-amine The title compound, MS m/e (%): 406 (M+H$^+$, 100), was prepared in accordance with the general method of example 48 from 3-phenyl-N-(2-phenyl-7-pyridin-4-yl-[1,2,4]triazolo[1,5-a]pyridin-5-yl)-propionamide.

EXAMPLE 58

Dibenzyl-(2-phenyl-7-pyridin-4-yl-[1,2,4]triazolo[1,5-a]pyridin-5-yl)-amine

A solution of 0.20 g (0.0007 mol) 2-phenyl-7-pyridin-4-yl-[1,2,4]triazolo[1,5-a]pyridin-5-ylamine in 17.5 ml dimethylsulfoxide was treated with 0.69 g (0.01 mol) potassiumhydroxide(85%) for 20 minutes at room temperature. Then 0.26 g (0.0015 mol) benzylbromide were added and stirring was continued for 70 hours. Saturated aqueous sodiumbicarbonate was added and the mixture was extracted with chloroform. Evaporation of the solvent and chromatography on silicagel with dichloromethane/methanol 98/2 and crystallisation from diethylether gave 0.12 g (44%) dibenzyl-(2-phenyl-7-pyridin-4-yl-[1,2,4]triazolo[1,5-a]pyridin-5-yl)-amine as light brown crystals. MS m/e (%): 468 (M+H$^+$, 100).

EXAMPLE 59

Diethyl-(2-phenyl-7-pyridin-4yl-[1,2,4]triazolo[1,5-a]pyridin-5-yl)-amine

A solution of 0.29 g (0.001 mol) 2-phenyl-7-pyridin-4-yl-[1,2,4]triazolo[1,5-a]pyridin-5-ylamine in 50 ml dimethylformamide was treated with 0.05 g (0.001 mol) sodiumhydride(55%) for 15 minutes at room temperature. Then 0.22 g (0.001 mol) ethyl-p-toluenesulfonate were added and stirring was continued for 22 hours. Addition of sodiumhydride and p-toluenesulfonate was repeated three times. After each addition stirring was continued at 50° C. for 20 hours. Saturated aqueous sodiumbicarbonate was added and the mixture was extracted with dichloromethane. Evaporation of the solvent and chromatography on silicagel with dichloromethane/methanol 96/4 gave 0.05 g (15%) diethyl-(2-phenyl-7-pyridin-4-yl-[1,2,4]triazolo[1,5-a]pyridin-5-yl)-amine as yellow oil. MS m/e (%): 343 (M+, 59), 314 (100), 300 (73), 104 (51).

EXAMPLE 60

2-[1-(2-Phenyl-7-pyridin-4-yl-[1,2,4]triazolo[1,5-a]pyridin-5-yl)-4,5 dihydro-1H-imidazole-2-yl]-benzoic acid The title compound, MS m/e (%): 461 (M+H+, 100), was prepared in accordance with the general method of example 27 from 2-phenyl-7-pyridin-4-yl-[1,2,4]triazolo[1,5-a]pyridin ylamine and N-(2-bromoethyl)-phthalimide.

EXAMPLE 61

2-[1-(2-Phenyl-7-pyridin-4-yl-[1,2,4]triazolo[1,5-a]pyridin-5-yl)-1,4,5,6-tetrahydro-pyrimidin-2-yl]-benzoic acid The title compound, MS m/e (%): 475 (M+H+, 100), was prepared in accordance with the general method of example 27 from 2-phenyl-7-pyridin-4-yl-[1,2,4]triazolo[1,5-a]pyridin-5-ylamine and N-(3-bromopropyl)-phthalimide.

EXAMPLE 62

2-[1-(2-Phenyl-7-pyridin-4-yl-[1,2,4]triazolo[1,5-a]pyridin-5-yl)-4,5,6,7-tetrahydro-1H-[1,3]diazepin-2-yl]-benzoic acid The title compound, MS m/e (%): 489 (M+H+, 100), was prepared in accordance with the general method of example 27 from 2-phenyl-7-pyridin-4-yl-[1,2,4]triazolo[1,5-a]pyridin-5-ylamine and N-(4-bromobutyl)-phthalimide.

EXAMPLE 63

2-Phenyl-7-p-tolyl-3H-[1,2,4]triazolo[1,5-a]pyridin-5-ylamine a) 4-Bromo-pyridine-2,6-dicarboxylic acid diethyl ester A mixture of 4.02 g (20 mmol) chelidamic acid monohydrate and 34.4 g (80 mmol) PBr$_5$ in 60 ml CCl$_4$ was heated to reflux for 12 h and afterwards cautiously treated with 20 ml EtOH. After 30 min at 80° C. the mixture was cooled to room temperature and the volatile components distilled off under reduced pressure. The remaining residue was treated with 200 ml ice/water mixture and stirred for 1 h. The white precipitate was filtered off washed with water and dried in high vacuum to yield 5.61 g (92.9%) of 4-bromo-pyridine-2,6-dicarboxylic acid diethyl ester, MS m/e (%): 302 (M+H+, 4), 229 (M+-(CO$_2$Et), 100)

b) 4-Bromo-pyridine-2,6-dicarboxylic acid dihydrazide

A solution of 4.76 g (15.7mmol) 4-bromo-pyridine-2,6-dicarboxylic acid diethyl ester in 87 ml ethanol was treated with 18.3 ml of a 24% solution of hydrazine in water and heated to 80° C. The formed white suspension was filtered hot and the collected white precipitate was dried to yield 3.51 g (81.4%) of the title compound, MS m/e (%): 276 (M++2, 100).

c) 4-Bromo-pyridine-2,6-diamine

A suspension of 1 g (3.65 mmol) 4-bromo-pyridine-2,6-dicarboxylic acid dihydrazide in 32 ml water was treated with 1.6 ml HCl (37%) at room temperature. The resulting mixture was cooled to 0° C. and 554 mg NaNO$_2$ in 2.4 ml water was added slowly maintaining the temperature below 2° C. Upon completion saturated NaHCO$_3$ solution was added to pH 8 and the white precipitate was filtered off and washed with water. The residue was dissolved in CHCl$_3$ and dried with MgSO$_4$. The filtrate was concentrated at 20° C. to yield 920 mg (85%) of a white solid 450 mg (1.5 mmol) of the white residue were suspended in toluene/t-butanol 5/1. After refluxing for 12h the solvent was removed under reduced pressure and 5 ml toluene and 0.3 ml trifluoroacetic acid were added and refluxed for 2 h. The solvents were removed and the residue was purified by flash chromatography on silica eluting with dichloromethane/methanol 9/1. After removal of the solvents the title compound was liberated through addition of 1N NaOH to a suspension of the residue in diethylether. The organic phase was dried with Na$_2$SO$_4$ and the solvents removed under reduced pressure yielding 192 mg (67%) of the desired product, MS m/e (%): 188 (M+, 100).

d) 7-Bromo-2-phenyl-[1,2,4]triazolo[,1,5-a]pyridin-5-ylamine

To a solution of 96 mg (0.51 mmol) 4-bromo-pyridine-2,6-diamine in 2.4 ml MeOH was added 121 mg (0.56 mmol) O-mesitylenesulfonylhydroxylamine (prepared from ethyl o-mesitylene-sulfonylacetohydroxamate and HClO$_4$ (70%)) in 0.6 ml MeOH at –5° C. and after 15min 71 mg (0.56 mmol) benzaldehyde and stirred for 30 min. The addition of 4.8 ml 1N KOH was followed by extraction with ethylacetate, drying of the organic layer with Na$_2$SO$_4$, and removal of the volatile components. The residue was purified by column chromatography on silica eluting with ethylacetate and hexane (2:3). 58 mg(39%) of 7-bromo-2-phenyl-[1,2,4]triazolo[1,5-a]pyridin-5-ylamine were isolated, MS m/e (%): 290 (M++2, 44).

e) 2-Phenyl-7-p-tolyl-3H-[1,2,4]triazolo[1,5-a]pyridin-5-ylamine

A mixture of 30 mg (0.1 mmol) 7-bromo-2-phenyl-[1,2,4]triazolo[1,5-a]pyridin-5-ylamine, 15.5 mg (0.11 mmol) p-tolyl-boronic acid, and 0.1 ml aqueous 2M Na$_2$CO$_3$ in 0.5 ml 1,2-dimethoxyethane was treated with 6 mg (0.01 mmol) tetrakis-(triphenylphosphine)-palladium(0) and heated to 90° C. for 15 h. Water was added and the mixture was adjusted to pH=12 with 2M NaOH and extracted with ethylacetate. The organic phases were dried with Na$_2$SO$_4$ and concentrated under reduced pressure yielding 22 mg (71%) 2-phenyl-7-p-tolyl-3H-[1,2,4]triazolo[1,5-a]pyridin-5-ylamine, MS m/e (%): 300 (M+, 100).

EXAMPLE 64

7-Bromo-2-furan-2-yl-[1,2,4]triazolo[1,5-a]pyridin-5-ylamine

The title compound, MS m/e (%): 281 (M++2, 100), was prepared in accordance with the (general method of example 63 from 4-bromo-pyridine-2,6-diamine, O-mesitylene-sulfonylhydroxylamine, and furfural. The purification was performed with reversed phase HPLC eluting with an acetonitrile/water gradient.

EXAMPLE 65

7-Bromo-2-(5-methyl-furan-2-yl)-[1,2,4 ]triazolo 1,5-a]pyridin-5-ylamine

The title compound, MS m/e (%): 295 (M++2, 100), was prepared in accordance with the general method of example 63 from 4-bromo-pyridine-2,6-diamine, O-mesitylene-sulfonylhydroxylamine, and 5-methyl-furfural. The purification was performed with reversed phase HPLC eluting a with an acetonitrile/water gradient.

EXAMPLE 66

[5-(5-Amino-7-bromo-[1,2,4]triazolo[1,5-a]pyridin-2-yl)-furan-2-yl]-methanol

The title compound, MS m/e (%): 311 (M$^{30}$ +2, 100), was prepared in accordance with the general method of example 63 from 4-bromo-pyridine-2,6-diamine, O-mesitylene-sulfonylhydroxylamine, and 5-hydroxymethyl-furfural. The purification was performed with reversed phase HPLC eluting with an acetonitrile/water gradient.

EXAMPLE 67

7-Bromo-2-(5-bromo-furan-2-yl)-[1,2,4]triazolo[1,5-a]pyridin-5-ylamine

The title compound, MS m/e (%): 359 ($M^+$+1, 100), was prepared in accordance with the general method of example 63 from 4-bromo-pyridine-2,6-diamine, O-mesitylene-sulfonylhydroxylamine, and 5-bromo-furfural. The purification was performed with reversed phase HPLC eluting with an acetonitrile/water gradient.

EXAMPLE 68

7-Bromo-2-(4-bromo-furan-2-yl)-[1,2,4]triazolo[1,5-a]pyridin-5-ylamine

The title compound, MS m/e (%): 359 ($M^+$+1, 100), was prepared in accordance with the general method of example 63 from 4-bromo-pyridine-2,6-diamine, O-mesitylene-sulfonylhydroxylamine, and 4-bromo-furfural. The purification was performed with reversed phase HPLC eluting with an acetonitrile/water gradient.

EXAMPLE 69

7-Bromo-2-(2-furan-2-yl-vinyl)-[1,2,4]triazolo[1,5-a]pyridin-5-ylamine

The title compound, MS m/e (%): 305 ($M^+$, 100), was prepared in accordance with the general method of example 63 from 4-bromo-pyridine-2,6-diamine, O-mesitylene-sulfonylhydroxylamine, and 3-(2-furyl)-acrolein. The purification was performed with reversed phase HPLC eluting with an acetonitrile/water gradient.

EXAMPLE 70

7-Bromo-2-thiophen-2-yl-[1,2,4]triazolo[1,5-a]pyridin-5-ylamine

The title compound, MS m/e (%): 297 ($M^+$+2, 100), was prepared in accordance with the general method of example 63 from 4-bromo-pyridine-2,6-diamine, O-mesitylene-sulfonylhydroxylamine, and 2-thiophenecarboxaldehyde. The purification was performed with reversed phase HPLC eluting with an acetonitrile/water gradient.

EXAMPLE 71

7-Bromo-2-(3-methyl-thiophen-2-yl)-[1,2,4]triazolo[1,5-a]pyridin-5-ylamine

The title compound, MS m/e (%): 309 ($M^+$, 100), was prepared in accordance with the general method of example 63 from 4-bromo-pyridine-2,6-diamine, O-mesitylene-sulfonylhydroxylamine, and 3-methylthiophene-2-carboxaldehyde. The purification was performed with reversed phase HPLC eluting with an acetonitrile/water gradient.

EXAMPLE 72

7-Bromo-2-(4-bromo-thiophen-2-yl)-[1,2,4]triazolo[1,5-a]pyridin-5-ylamine

The title compound, MS m/e (%): 375 ($M^+$+1, 100), was prepared in accordance with the general method of example 63 from 4-bromo-pyridine-2,6-diamine, O-mesitylene-sulfonylhydroxylamine, and 4-bromothiophene-2-carboxaldehyde. The purification was performed with reversed phase HPLC eluting with an acetonitrile/water gradient.

EXAMPLE 73

7-Bromo-2-(1-methyl-1H-pyrrol-2-yl)-[1,2,4]triazolo[1,5-a]pyridin-5-ylamine

The title compound, MS m/e (%): 294 ($M^+$+2, 100), was prepared in accordance with the general method of example 63 from 4-bromo-pyridine-2,6-diamine, O-mesitylene-sulfonylhydroxylamine, and 1-methylpyrrole-2-carboxaldehyde. The purification was performed with reversed phase HPLC eluting with an acetonitrile/water gradient.

EXAMPLE 74

7-Bromo-2-thiazol-2-yl-[1,2,4]triazolo[1,5-a]pyridin-5-ylamine

The title compound, MS m/e (%): 298 ($M^+$+2, 100), was prepared in accordance with the general method of example 63 from 4-bromo-pyridine-2,6-diamine, O-mesitylene-sulfonylhydroxylamine, and 2-formylthiazole. The purification was performed with reversed phase HPLC eluting with an acetonitrile/water gradient.

EXAMPLE 75

7-Bromo-2-pyridin-4-yl-[1,2,4]triazolo[1,5-a]pyridin-5-ylamine

The title compound, MS m/e (%): 292 ($M^+$+2, 100), was prepared in accordance with the general method of example 63 from 4-bromo-pyridine-2,6-diamine, O-mesitylene-sulfonylhydroxylamine, and 4-pyridinecarboxaldehyde. The purification was performed with reversed phase HPLC eluting with an acetonitrile/water gradient.

EXAMPLE 76

7-Bromo-2-(6-methyl-pyridin-+2-yl)-[1,2,4]triazolo[1,5-a]pyridin-5-ylamine

The title compound, MS m/e (%): 306 ($M^+$2, 100), was prepared in accordance with the general method of example 63 from 4-bromo-pyridine-2,6-diamine, O-mesitylene-sulfonylhydroxylamine, and 6-methylpyridine-2-aldehyde. The purification was performed with reversed phase HPLC eluting with an acetonitrile/water gradient.

EXAMPLE 77

7-Bromo-2-(1H-indol-3-yl)-[1,2,4]triazolo[1,5-a]pyridin-5-ylamine

The title compound, MS m/e (%): 328 ($M^+$, 100), was prepared in accordance with the general method of example 63 from 4-bromo-pyridine-2,6-diamine, O-mesitylene-sulfonyl-hydroxylamine, and indole-3-carboxaldehyde. The purification was performed with reversed phase HPLC eluting with an acetonitrile/water gradient.

EXAMPLE 78

2-(5-Amino-7-bromo-[1,2,4]triazolo[1,5-a]pyridin-2-yl)-phenol

The title compound, MS m/e (%): 307 ($M^+$2, 100), was prepared in accordance with the general method of example 63 from 4-bromo-pyridine-2,6-diamine, O-mesitylene-sulfonylhydroxylamine, and salicylaldehyde. The purification was performed with reversed phase HPLC eluting with an acetonitrile/water gradient.

EXAMPLE 79

7-Bromo-2-(2-methoxy-phenyl)-[1,2,4]triazolo[1,5-a]pyridin-5-ylamine

The title compound, MS m/e (%): 321 ($M^+ +2$, 100), was prepared in accordance with the general method of example 63 from 4-bromo-pyridine-2,6-diamine, O-mesitylene-sulfonylhydroxylamine, and o-anisaldehyde. The purification was performed with reversed phase HPLC eluting with an acetonitrile/water gradient.

EXAMPLE 80

7-Bromo-2-(5-ethyl-furan-2-yl)-[1,2,4]triazolo[1,5-a]pyridin-5-ylamine

The title compound, MS m/e (%): 309 ($M^+ +2$, 100), was prepared in accordance with the general method of example 63 from 4-bromo-pyridine-2,6-diamine, O-mesitylene-sulfonylhydroxylamine, and 5-ethyl-2-furaldehyde. The purification was performed with reversed phase HPLC eluting with an acetonitrile/water gradient.

EXAMPLE 81

7-Bromo-2-furan-3-yl-[1,2,4]triazolo[1,5-a]pyridin-5-ylamine

The title compound, MS m/e (%): 281 ($M^+ +2$, 100), was prepared in accordance with the general method of example 63 from 4-bromo-pyridine-2,6-diamine, O-mesitylene-sulfonylhydroxylamine, and 3-furaldehyde. The purification was performed with reversed phase HPLC eluting with an acetonitrile/water gradient.

EXAMPLE 82

7-Bromo-2-(5-methyl-thiophen-2-yl)-[1,2,4]triazolo[,1,5-a]pyridin-5-ylamine

The title compound, MS m/e (%): 311 ($M^+ +2$, 100), was prepared in accordance with the general method of example 63 from 4-bromo-pyridine-2,6-diamine, O-mesitylene-sulfonylhydroxylamine, and 5-methyl-2-thiophenecarboxaldehyde. The purification was performed with reversed phase HPLC eluting with an acetonitrile/water gradient.

EXAMPLE 83

7-Bromo-2-(tetrahydro-furan-2-yl)-[1,2,4]triazolo[1,5-a]pyridin-5-ylamine

The title compound, MS m/e (%): 283 ($M^+$, 100), was prepared in accordance with the general method of example 63 from 4-bromo-pyridine-2,6-diamine, O-mesitylene-sulfonylhydroxylamine, and tetrahydro-furan-2-carbaldehyde. The purification was performed with reversed phase HPLC eluting with an acetonitrile/water gradient.

EXAMPLE 84

7-Bromo-2-(3-fluoro-phenyl)-[1,2,4]triazolo[1,5-a]pyridin-5-ylamine

The title compound, MS m/e (%): 307 ($M^+$, 100), was prepared in accordance with the general method of example 63 from 4-bromo-pyridine-2,6-diamine, O-mesitylene-sulfonylhydroxylamine, and 3-fluoro-benzaldehyde. The purification was performed with reversed phase HPLC eluting with an acetonitrile/water gradient.

EXAMPLE 85

7-Bromo-2-(5-methoxy-thiophen-2-yl)-[1,2,4]triazolo[1,5-a]pyridin-5-ylamine

The title compound, MS m/e (%): 325 ($M^+$, 100), was prepared in accordance with the general method of example 63 from 4-bromo-pyridine-2,6-diamine, O-mesitylene-sulfonylhydroxylamine, and 5-methoxy-thiophene-2-carbaldehyde. The purification was performed with reversed phase HPLC eluting with an acetonitrile/water gradient.

EXAMPLE 86

7-Bromo-2-(4-methoxy-thiophen-2-yl)-[1,2,4]triazolo[1,5-a]pyridin-5-ylamine

The title compound, MS m/e (%): 325 ($M^+$, 100), was prepared in accordance with the general method of example 63 from 4-bromo-pyridine-2,6-diamine, O-mesitylene-sulfonylhydroxylamine, and 4-methoxy-thiophene-2-carbaldehyde. The purification was performed with reversed phase HPLC eluting with an acetonitrile/water gradient.

EXAMPLE 87

7-Bromo-2-(5,6-dihydro-4H-pyran-2-yl)-[1,2,4]triazolo[1,5-a]pyridin-5-ylamine

The title compound, MS m/e (%): 295 ($M^+$, 100), was prepared in accordance with the general method of example 63 from 4-bromo-pyridine-2,6-diamine, O-mesitylene-sulfonylhydroxylamine, and 5,6-dihydro-4H-pyran-2-carbaldehyde. The purification was performed with reversed phase HPLC eluting with an acetonitrile/water gradient.

EXAMPLE 88

7-Bromo-2-pyridin-2-yl-[1,2,4]triazolo[1,5-a]pyridin-5-ylamine

The title compound, MS m/e (%): 290 ($M^+$, 100), was prepared in accordance with the general method of example 63 from 4-bromo-pyridine-2,6-diamine, O-mesitylene-sulfonylhydroxylamine, and pyridine-2-carbaldehyde. The purification was performed with reversed phase HPLC eluting with an acetonitrile/water gradient.

EXAMPLE 89

7-Bromo-2-(2-fluoro-phenyl)-[1,2,4]triazolo[1,5-a]pyridin-5-ylamine

The title compound, MS m/e (%): 290 ($M^+$, 100), was prepared in accordance with the general method of example 63 from 4-bromo-pyridine-2,6-diamine, O-mesitylene-sulfonyl-hydroxylamine, and 2-fluoro-benzaldehyde. The purification was performed with reversed phase HPLC eluting with an acetonitrile/water gradient.

EXAMPLE 90

7-Bromo-2-(6-methoxy-pyridin-2-yl)-[1,2,4]triazolo[1,5-a]pyridin-5-ylamine

The title compound, MS m/e (%): 320 ($M^+$, 100), was prepared in accordance with the general method of example

EXAMPLE 91

7-Bromo-2-isoxazol-5-yl-[1,2,4]triazolo[1,5-a]pyridin-5-ylamine

The title compound, MS m/e (%): 280 (M$^+$, 100), was prepared in accordance with the general method of example 63 from 4-bromo-pyridine-2,6-diamine, O-mesitylene-sulfonylhydroxylamine, and isoxazole-5-carbaldehyde. The purification was performed with reversed phase HPLC eluting with an acetonitrile/water gradient.

EXAMPLE 92

7-(4-Methoxy-phenyl)-2-pyridin-2-yl-[1,2,4]triazolo[1,5-a]pyridin-5-ylamine

A mixture of 72.5 mg (0.25 mmol) 7-bromo-2-pyridin-2-yl-[1,2,4]triazolo[1,5-a]pyridin-5-ylamine, 37.4 mg (0.275 mmol) p-methoxy-boronic acid, and 0.22 ml 2M Na$_2$CO$_3$ in 0.78 ml dioxane was treated with 0.05 eq. dichloro (1,1'-bis(diphenylphosphino) ferrocene)palladium (II) dichloromethane adduct and heated to 100° C. for 15 h. Formic acid was added and the mixture was purified by reversed phase column chromatography eluting with an acetonitrile/water gradient yielding 13.3 mg (17%) of the title compound. MS m/e (%): 318 (M+H$^+$, 100)

According to example 63 or example 92 triazolopyridine derivatives have been synthesised. The results are compiled in the following list comprising example 93 to example 220.

(Previous column continued:)
63 from 4-bromo-pyridine-2,6-diamine, O-mesitylene-sulfonyl-hydroxylamine, and 6-methoxy-pyridine-2-carbaldehyde. The purification was performed with reversed phase HPLC eluting with an acetonitrile/water gradient.

| Example No. | Structure | Name | MS m/e (%) | MW | Synthesis according to example No. |
|---|---|---|---|---|---|
| 93 | 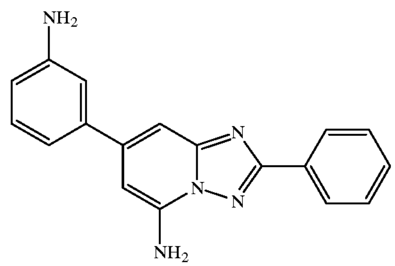 | 7-(3-Amino-phenyl)-2-phenyl-[1,2,4]triazolo[1,5-a]pyridin-5-ylamine | M + H⁺(100) | 301.4 | 63 |
| 94 | 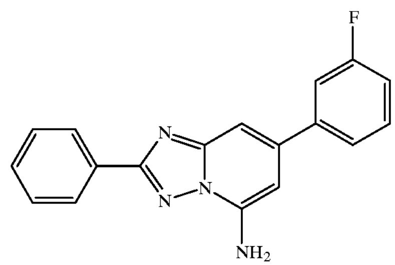 | 7-(3-Fluoro-phenyl)-2-phenyl-[1,2,4]triazolo[1,5-a]pyridin-5-ylamine | M + H⁺(100) | 304.3 | 63 |
| 95 | 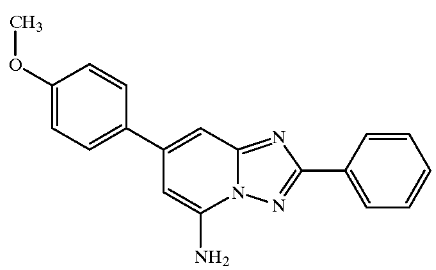 | 7-(4-Methoxy-phenyl)-2-phenyl-[1,2,4]triazolo[1,5-a]pyridin-5-ylamine | M + H⁺(100) | 316.4 | 63 |

| Example No. | Structure | Name | MS m/e (%) | MW | Synthesis according to example No. |
|---|---|---|---|---|---|
| 96 | 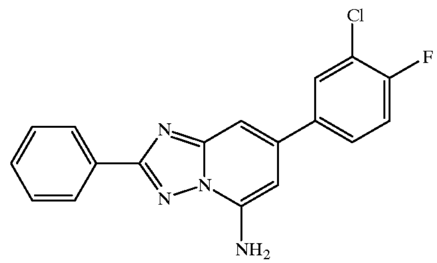 | 7-(3-Chloro-4-fluoro-phenyl)-2-phenyl-[1,2,4]triazolo[1,5-a]pyridin-5-ylamine | M + H⁺(100) | 338.8 | 63 |
| 97 | 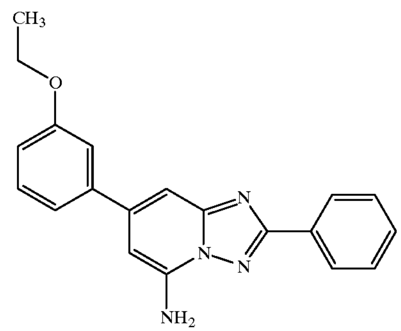 | 7-(3-Ethoxy-phenyl)-2-phenyl-[1,2,4]triazolo[1,5-a]pyridin-5-ylamine | M + H⁺(100) | 330.4 | 63 |
| 98 | 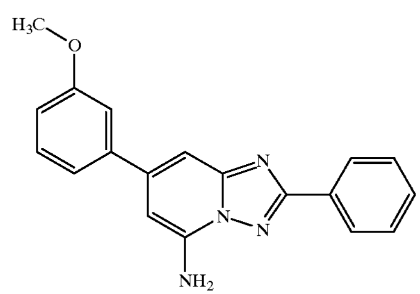 | 7-(3-Methoxy-phenyl)-2-phenyl-[1,2,4]triazolo[1,5-a]pyridin-5-ylamine | M + H⁺(100) | 316.4 | 63 |

-continued

| Example No. | Structure | Name | MS m/e (%) | MW | Synthesis according to example No. |
|---|---|---|---|---|---|
| 99 | 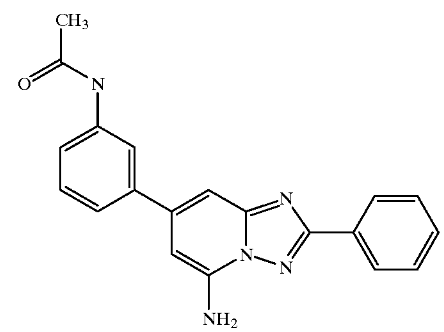 | N-[3-(5-Amino-2-phenyl-[1,2,4]triazolo[1,5-a]pyridin-7-yl)-phenyl]-acetamide | M + H⁺(100) | 343.4 | 63 |
| 100 | 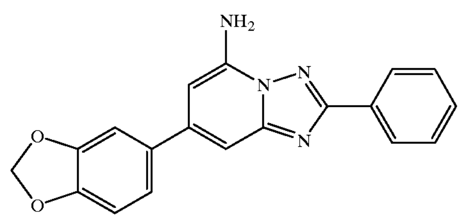 | 7-Benzo[1,3]dioxol-5-yl-2-phenyl-[1,2,4]triazolo[1,5-a]pyridin-5-ylamine | M + H⁺(100) | 330.3 | 63 |
| 101 | 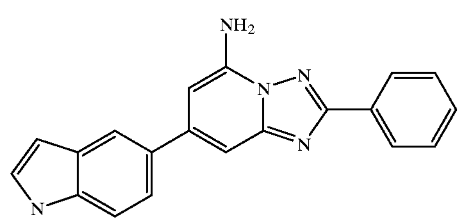 | 7-(1H-Indol-5-yl)-2-phenyl-[1,2,4]triazolo[1,5-a]pyridin-5-ylamine | M + H⁺(100) | 325.4 | 63 |

-continued

| Example No. | Structure | Name | MS m/e (%) | MW | Synthesis according to example No. |
|---|---|---|---|---|---|
| 102 | 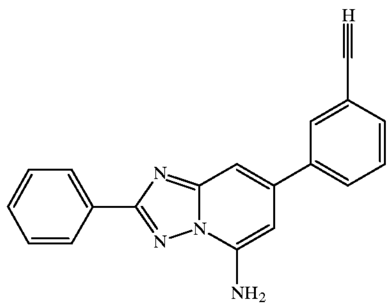 | 3-(5-Amino-2-phenyl-[1,2,4]triazolo[1,5-a]pyridin-7-yl)-benzonitrile | M + H⁺(100) | 311.3 | 63 |
| 103 | 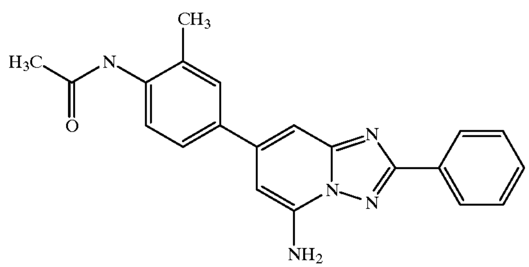 | N-[4-(5-Amino-2-phenyl-[1,2,4]triazolo[1,5-a]pyridin-7-yl)-2-methyl-phenyl]-acetamide | M + H⁺(100) | 357.4 | 63 |
| 104 | 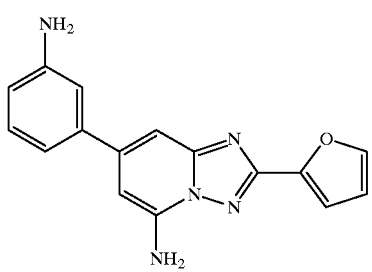 | 7-(3-Amino-phenyl)-2-furan-2-yl-[1,2,4]triazolo[1,5-a]pyridin-5-ylamine | M + H⁺(100) | 291.3 | 63 |

| Example No. | Structure | Name | MS m/e (%) | MW | Synthesis according to example No. |
|---|---|---|---|---|---|
| 105 | 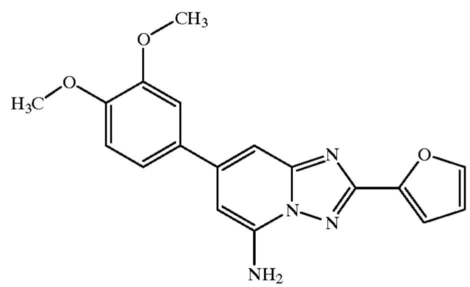 | 7-(3,4-Dimethoxy-phenyl)-2-furan-2-yl-[1,2,4]triazolo[1,5-a]pyridin-5-ylamine | M + H⁺(100) | 336.4 | 63 |
| 106 | 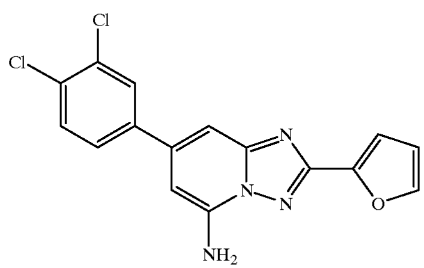 | 7-(3,4-Dichloro-phenyl)-2-furan-2-yl-[1,2,4]triazolo[1,5-a]pyridin-5-ylamine | M⁺(100) | 345.2 | 63 |
| 107 | 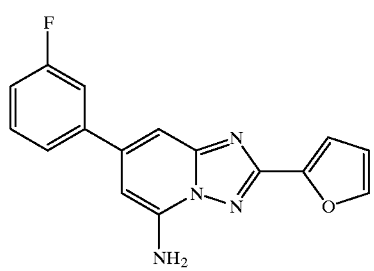 | 7-(3-Fluoro-phenyl)-2-furan-2-yl-[1,2,4]triazolo[1,5-a]pyridin-5-ylamine | M + H⁺(100) | 294.3 | 63 |

-continued

| Example No. | Structure | Name | MS m/e (%) | MW | Synthesis according to example No. |
|---|---|---|---|---|---|
| 108 | 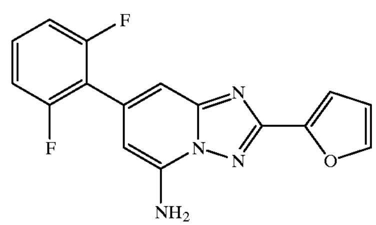 | 7-(2,6-Difluoro-phenyl)-2-furan-2-yl-[1,2,4]triazolo[1,5-a]pyridin-5-ylamine | M + H$^+$(100) | 312.3 | 63 |
| 109 | 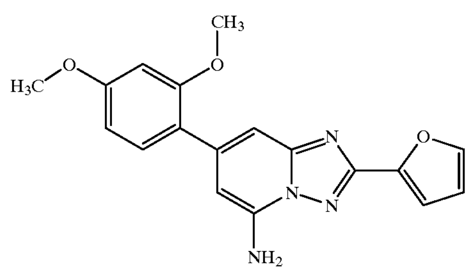 | 7-(2,4-Dimethoxy-phenyl)-2-furan-2-yl-[1,2,4]triazolo[1,5-a]pyridin-5-ylamine | M + H$^+$(100) | 336.4 | 63 |
| 110 | 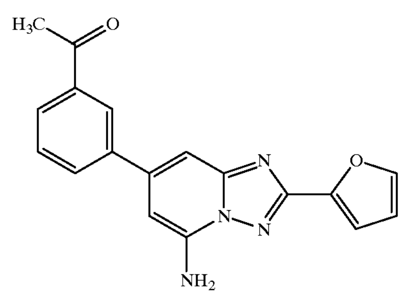 | 1-[3-(5-Amino-2-furan-2-yl-[1,2,4]triazolo[1,5-a]pyridin-7-yl)-phenyl]-ethanone | M + H$^+$(100) | 318.3 | 63 |

-continued

| Example No. | Structure | Name | MS m/e (%) | MW | Synthesis according to example No. |
|---|---|---|---|---|---|
| 111 | 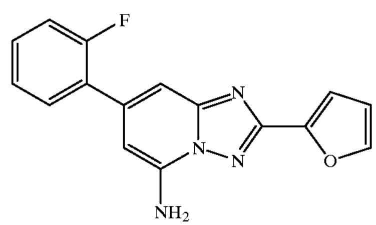 | 7-(2-Fluoro-phenyl)-2-furan-2-yl-[1,2,4]triazolo[1,5-a]pyridin-5-ylamine | M + H⁺(100) | 294.3 | 63 |
| 112 | 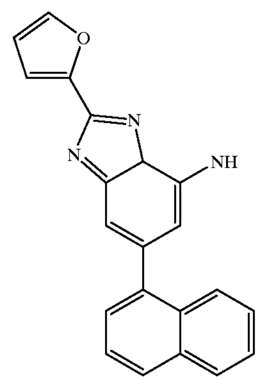 | 2-Furan-2-yl-7-naphthalen-1-yl-[1,2,4]triazolo[1,5-a]pyridin-5-ylamine | M + H⁺(100) | 326.4 | 63 |
| 113 | 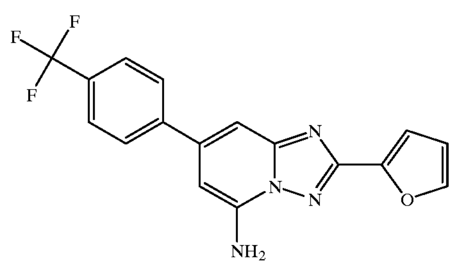 | 2-Furan-2-yl-7-(4-trifluoromethyl-phenyl)-[1,2,4]triazolo[1,5-a]pyridin-5-ylamine | M + H⁺(100) | 344.3 | 63 |

-continued

| Example No. | Structure | Name | MS m/e (%) | MW | Synthesis according to example No. |
|---|---|---|---|---|---|
| 114 | 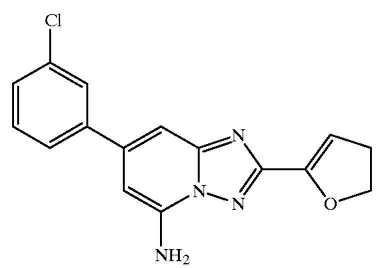 | 7-(3-Chloro-phenyl)-2-furan-2-yl-[1,2,4]triazolo[1,5-a]pyridin-5-ylamine | M + H⁺(100) | 310.7 | 63 |
| 115 | 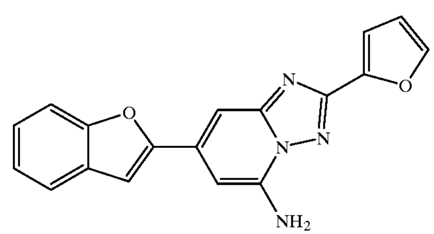 | 7-Benzofuran-2-yl-2-furan-2-yl-[1,2,4]triazolo[1,5-a]pyridin-5-ylamine | M + H⁺(100) | 316.3 | 63 |
| 116 | 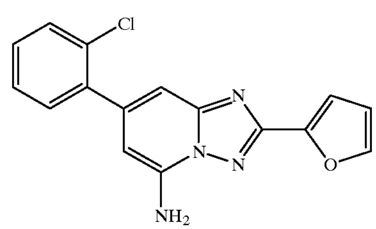 | 7-(2-Chloro-phenyl)-2-furan-2-yl-[1,2,4]triazolo[1,5-a]pyridin-5-ylamine | M + H⁺(100) | 310.7 | 63 |

| Example No. | Structure | Name | MS m/e (%) | MW | Synthesis according to example No. |
|---|---|---|---|---|---|
| 117 | 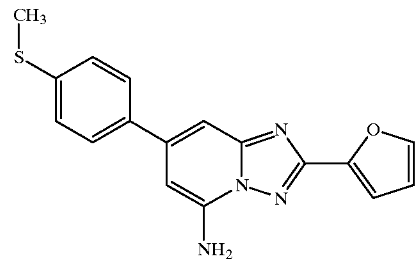 | 2-Furan-2-yl-7-(4-methylsulfanyl-phenyl)-[1,2,4]triazolo[1,5-a]pyridin-5-ylamine | M + H⁺(100) | 322.4 | 63 |
| 118 | 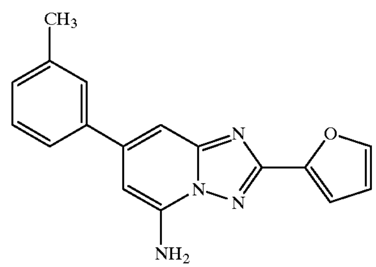 | 2-Furan-2-yl-7-m-tolyl-[1,2,4]triazolo[1,5-a]pyridin-5-ylamine | M + H⁺(100) | 290.3 | 63 |
| 119 | 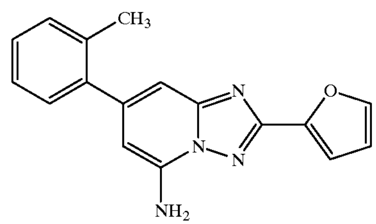 | 2-Furan-2-yl-7-o-tolyl-[1,2,4]triazolo[1,5-a]pyridin-5-ylamine | M + H⁺(100) | 290.3 | 63 |
| 120 | 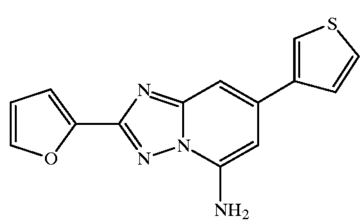 | 2-Furan-2-yl-7-thiophen-3-yl-[1,2,4]triazolo[1,5-a]pyridin-5-ylamine | M + H⁺(100) | 282.3 | 63 |

-continued

| Example No. | Structure | Name | MS m/e (%) | MW | Synthesis according to example No. |
|---|---|---|---|---|---|
| 121 | 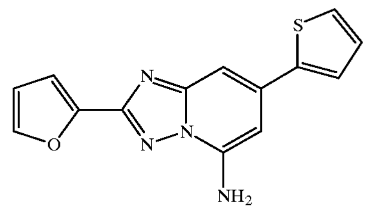 | 2-Furan-2-yl-7-thiophen-2-yl-[1,2,4]triazolo[1,5-a]pyridin-5-ylamine | M + H⁺(100) | 282.3 | 63 |
| 122 | 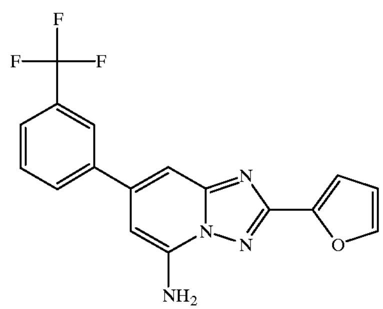 | 2-Furan-2-yl-7-(3-trifluoromethyl-phenyl)-[1,2,4]triazolo[1,5-a]pyridin-5-ylamine | M + H⁺(100) | 344.3 | 63 |
| 123 | 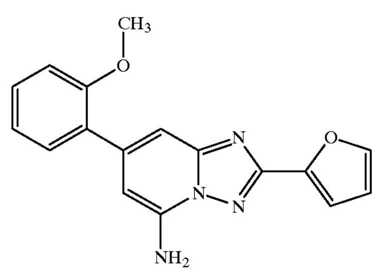 | 2-Furan-2-yl-7-(2-methoxy-phenyl)-[1,2,4]triazolo[1,5-a]pyridin-5-ylamine | M + H⁺(100) | 306.3 | 63 |

| Example No. | Structure | Name | MS m/e (%) | MW | Synthesis according to example No. |
|---|---|---|---|---|---|
| 124 | 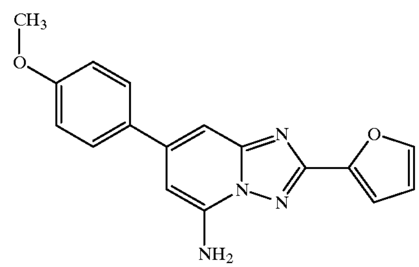 | 2-Furan-2-yl-7-(4-methoxy-phenyl)-[1,2,4]triazolo[1,5-a]pyridin-5-ylamine | M + H⁺(100) | 306.3 | 63 |
| 125 | 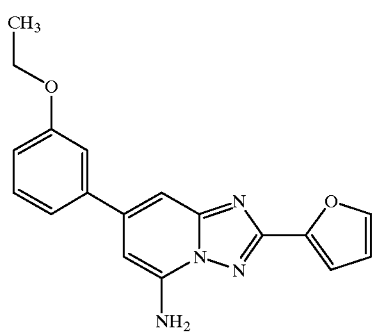 | 7-(3-Ethoxy-phenyl)-2-furan-2-yl-[1,2,4]triazolo[1,5-a]pyridin-5-ylamine | M + H⁺(100) | 320.4 | 63 |
| 126 | 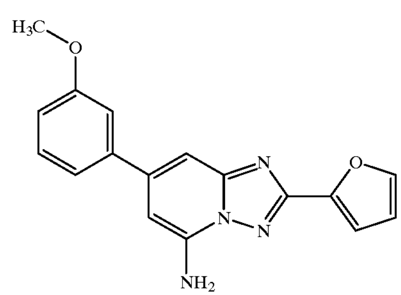 | 2-Furan-2-yl-7-(3-methoxy-phenyl)-[1,2,4]triazolo[1,5-a]pyridin-5-ylamine | M + H⁺(100) | 306.3 | 63 |

-continued

| Example No. | Structure | Name | MS m/e (%) | MW | Synthesis according to example No. |
|---|---|---|---|---|---|
| 127 | 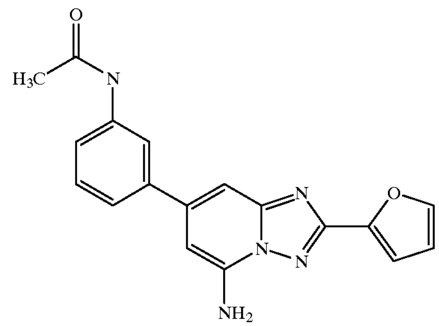 | N-[3-(5-Amino-2-furan-2-yl-[1,2,4]triazolo[1,5-a]pyridin-7-yl)-phenyl]-acetamide | M + H⁺(100) | 333.4 | 63 |
| 128 | 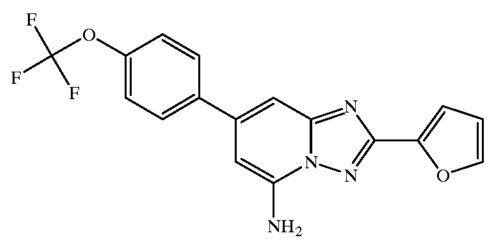 | 2-furan-2-yl-7-(4-trifluoromethoxy-phenyl)-[1,2,4]triazolo[1,5-a]pyridin-5-ylamine | M + H⁺(100) | 360.3 | 63 |
| 129 | 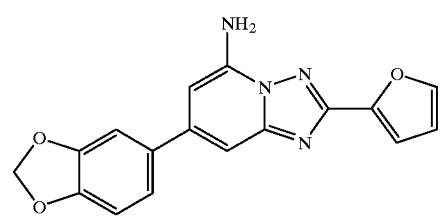 | 7-Benzo[1,3]dioxol-5-yl-2-furan-2-yl-[1,2,4]triazolo[1,5-a]pyridin-5-ylamine | M + H⁺(100) | 320.3 | 63 |

-continued

| Example No. | Structure | Name | MS m/e (%) | MW | Synthesis according to example No. |
|---|---|---|---|---|---|
| 130 | 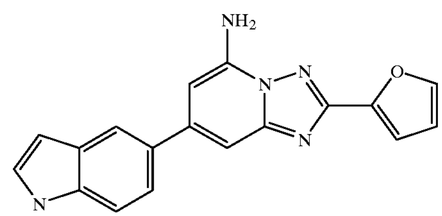 | 2-Furan-2-yl-7-(1H-indol-5-yl)-[1,2,4]triazolo[1,5-a]pyridin-5-ylamine | M + H⁺(100) | 315.3 | 63 |
| 131 | 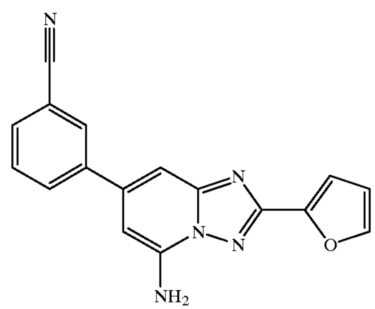 | 3-(5-Amino-2-furan-2-yl-[1,2,4]triazolo[1,5-a]pyridin-7-yl)-benzonitrile | M + H⁺(100) | 301.3 | 63 |
| 132 | 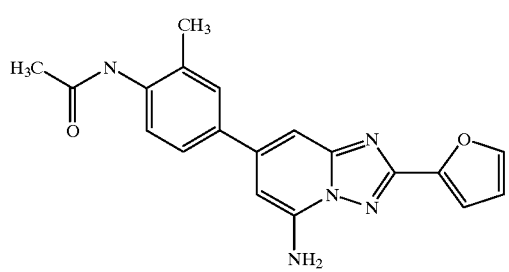 | N-[4-(5-Amino-2-furan-2-yl-[1,2,4]triazolo[1,5-a]pyridin-7-yl)-2-methyl-phenyl]-acetamide | M + H⁺(100) | 347.4 | 63 |

-continued

| Example No. | Structure | Name | MS m/e (%) | MW | Synthesis according to example No. |
|---|---|---|---|---|---|
| 133 | 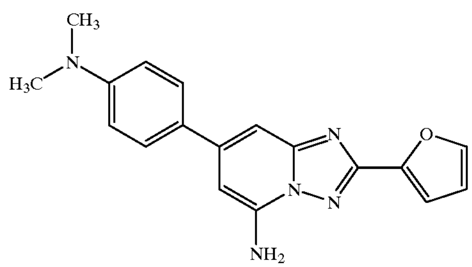 | 7-(4-Dimethylamino-phenyl)-2-furan-2-yl-[1,2,4]triazolo[1,5-a]pyridin-5-ylamine | M + H⁺(100) | 319.4 | 63 |
| 134 | 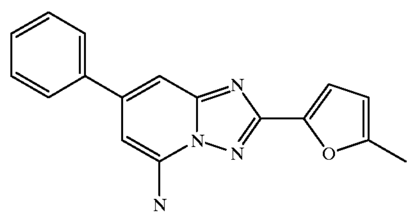 | 2-(5-Methyl-furan-2-yl)-7-phenyl-[1,2,4]triazolo[1,5-a]pyridin-5-ylamine | M + H⁺(100) | 290.3 | 63 |
| 135 | 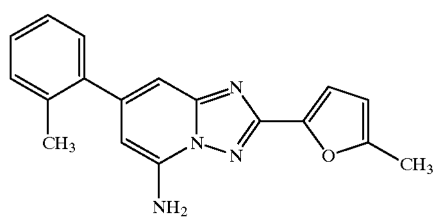 | 2-(5-Methyl-furan-2-yl)-7-o-tolyl-[1,2,4]triazolo[1,5-a]pyridin-5-ylamine | M + H⁺(100) | 304.4 | 63 |
| 136 | 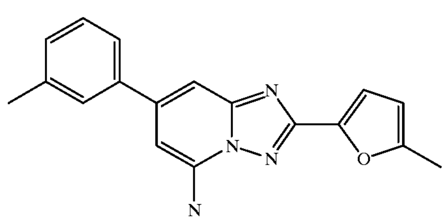 | 2-(5-Methyl-furan-2-yl)-7-m-tolyl-[1,2,4]triazolo[1,5-a]pyridin-5-ylamine | M + H⁺(100) | 304.4 | 63 |

| Example No. | Structure | Name | MS m/e (%) | MW | Synthesis according to example No. |
|---|---|---|---|---|---|
| 137 | 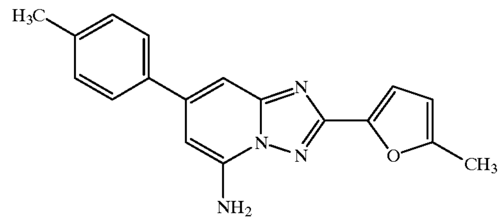 | 2-(5-Methyl-furan-2-yl)-7-p-tolyl-[1,2,4]triazolo[1,5-a]pyridin-5-ylamine | M + H⁺(100) | 304.4 | 63 |
| 138 | 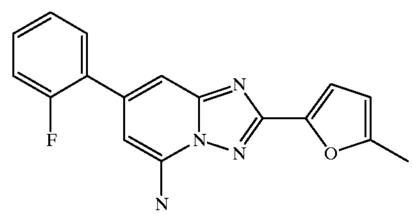 | 7-(2-Fluoro-phenyl)-2-(5-methyl-furan-2-yl)-[1,2,4]triazolo[1,5-a]pyridin-5-ylamine | M + H⁺(100) | 308.3 | 63 |
| 139 | 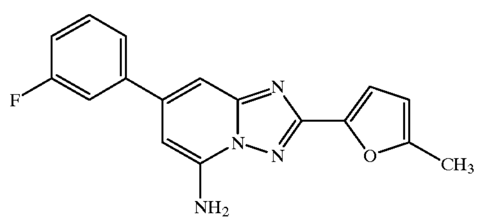 | 7-(3-Fluoro-phenyl)-2-(5-methyl-furan-2-yl)-[1,2,4]triazolo[1,5-a]pyridin-5-ylamine | M + H⁺(100) | 308.3 | 63 |
| 140 | 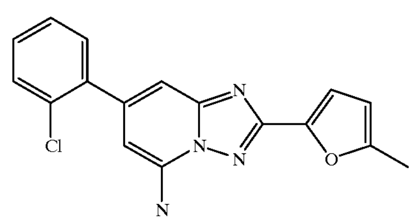 | 7-(2-Chloro-phenyl)-2-(5-methyl-furan-2-yl)-[1,2,4]triazolo[1,5-a]pyridin-5-ylamine | M⁺(100) | 324.8 | 63 |

| Example No. | Structure | Name | MS m/e (%) | MW | Synthesis according to example No. |
|---|---|---|---|---|---|
| 141 | 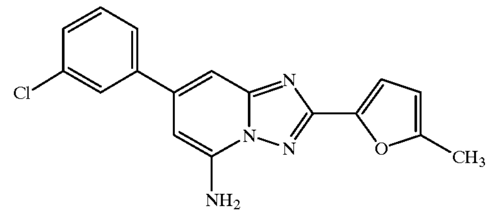 | 7-(3-Chloro-phenyl)-2-(5-methyl-furan-2-yl)-[1,2,4]triazolo[1,5-a]pyridin-5-ylamine | M⁺(100) | 324.8 | 63 |
| 142 | 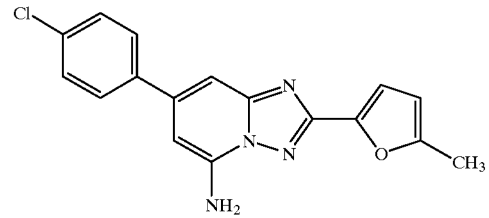 | 7-(4-Chloro-phenyl)-2-(5-methyl-furan-2-yl)-[1,2,4]triazolo[1,5-a]pyridin-5-ylamine | M⁺(100) | 324.8 | 63 |
| 143 | 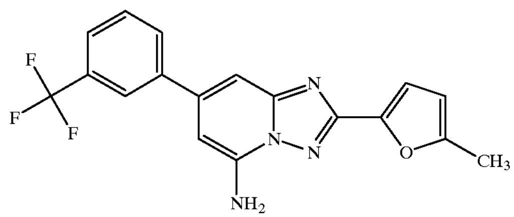 | 2-(5-Methyl-furan-2-yl)-7-(3-trifluoromethyl-phenyl)-[1,2,4]triazolo[1,5-a]pyridin-5-ylamine | M + H⁺(100) | 358.3 | 63 |
| 144 | 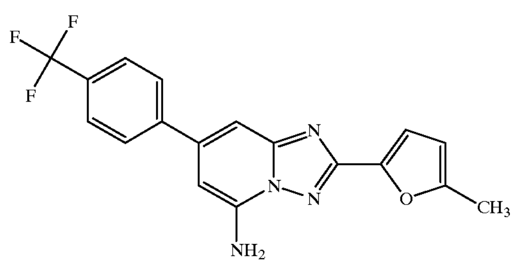 | 2-(5-Methyl-furan-2-yl)-7-(4-trifluoromethyl-phenyl)-[1,2,4]triazolo[1,5-a]pyridin-5-ylamine | M + H⁺(100) | 358.3 | 63 |

-continued

| Example No. | Structure | Name | MS m/e (%) | MW | Synthesis according to example No. |
|---|---|---|---|---|---|
| 145 | 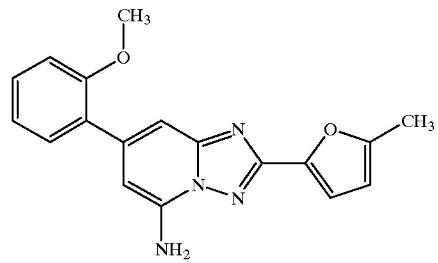 | 7-(2-Methoxy-phenyl)-2-(5-methyl-furan-2-yl)-[1,2,4]triazolo[1,5-a]pyridin-5-ylamine | M + H⁺(100) | 320.4 | 63 |
| 146 | 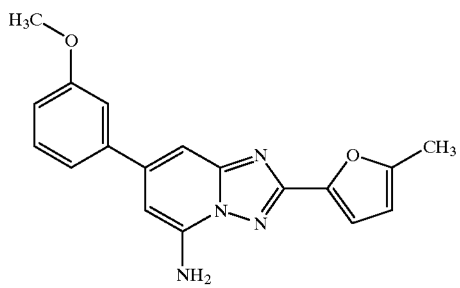 | 7-(3-Methoxy-phenyl)-2-(5-methyl-furan-2-yl)-[1,2,4]triazolo[1,5-a]pyridin-5-ylamine | M + H⁺(100) | 320.4 | 63 |
| 147 | 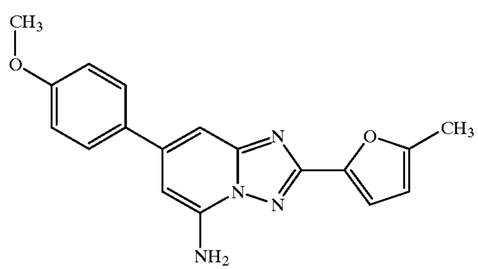 | 7-(4-Methoxy-phenyl)-2-(5-methyl-furan-2-yl)-[1,2,4]triazolo[1,5-a]pyridin-5-ylamine | M + H⁺(100) | 320.4 | 63 |

| Example No. | Structure | Name | MS m/e (%) | MW | Synthesis according to example No. |
|---|---|---|---|---|---|
| 148 | 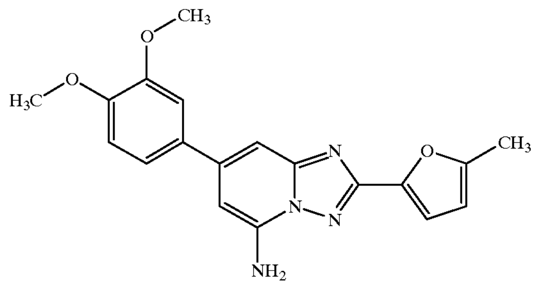 | 7-(3,4-Dimethoxy-phenyl)-2-(5-methyl-furan-2-yl)-[1,2,4]triazolo[1,5-a]pyridin-5-ylamine | M + H⁺(100) | 350.4 | 63 |
| 149 | 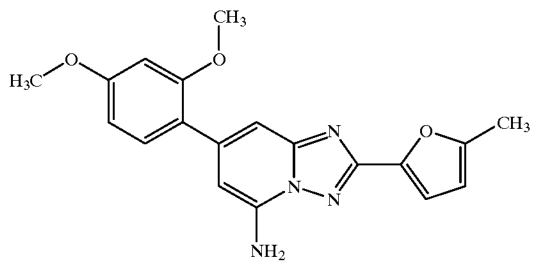 | 7-(2,4-Dimethoxy-phenyl)-2-(5-methyl-furan-2-yl)-[1,2,4]triazolo[1,5-a]pyridin-5-ylamine | M + H⁺(100) | 350.4 | 63 |
| 150 | 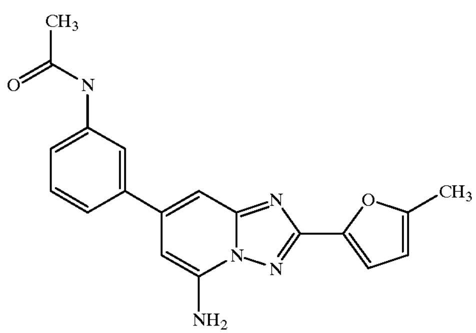 | N-{3-[5-Amino-2-(5-methyl-furan-2-yl)-[1,2,4]triazolo[1,5-a]pyridin-7-yl]-phenyl}-acetamide | M + H⁺(100) | 347.4 | 63 |

-continued

| Example No. | Structure | Name | MS m/e (%) | MW | Synthesis according to example No. |
|---|---|---|---|---|---|
| 151 | 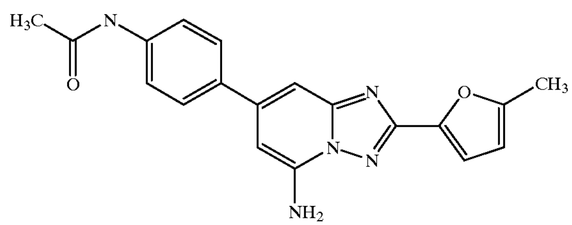 | N-{4-[5-Amino-2-(5-methyl-furan-2-yl)-[1,2,4]triazolo[1,5-a]pyridin-7-yl]-phenyl}-acetamide | M + H$^+$(100) | 347.4 | 63 |
| 152 | 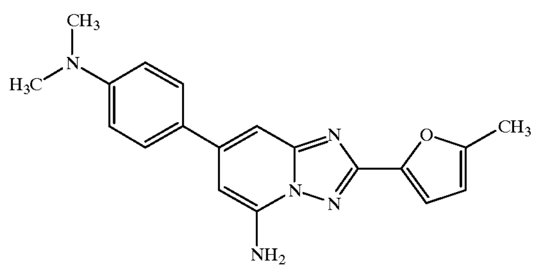 | 7-(4-Dimethylamino-phenyl)-2-(5-methyl-furan-2-yl)-[1,2,4]triazolo[1,5-a]pyridin-5-ylamine | M + H$^+$(100) | 333.4 | 63 |
| 153 | 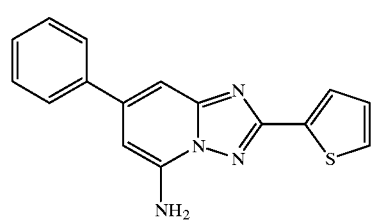 | 7-Phenyl-2-thiophen-2-yl-[1,2,4]triazolo[1,5-a]pyridin-5-ylamine | M + H$^+$(100) | 292.4 | 63 |
| 154 | 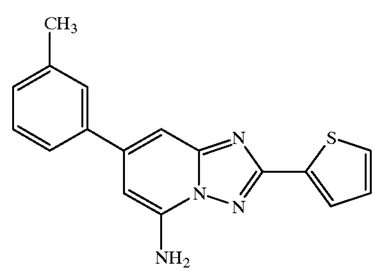 | 2-Thiophen-2-yl-7-m-tolyl-[1,2,4]triazolo[1,5-a]pyridin-5-ylamine | M + H$^+$(100) | 306.4 | 63 |

-continued

| Example No. | Structure | Name | MS m/e (%) | MW | Synthesis according to example No. |
|---|---|---|---|---|---|
| 155 | 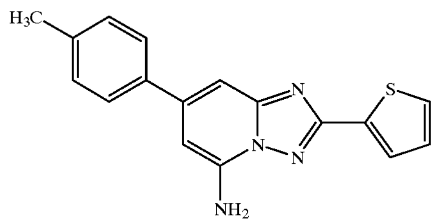 | 2-Thiophen-2-yl-7-p-tolyl-[1,2,4]triazolo[1,5-a]pyridin-5-ylamine | M + H⁺ (100) | 306.4 | 63 |
| 156 | 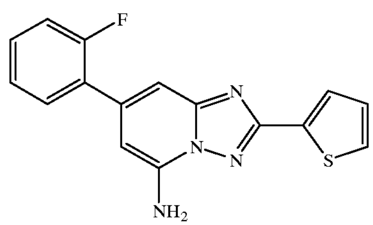 | 7-(2-Fluoro-phenyl)-2-thiophen-2-yl-[1,2,4]triazolo[1,5-a]pyridin-5-ylamine | M + H⁺ (100) | 310.4 | 63 |
| 157 | 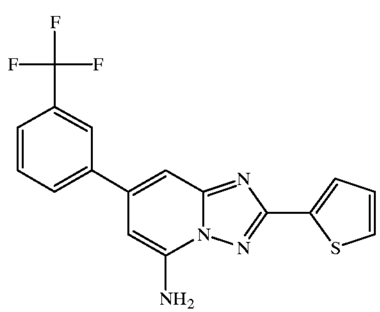 | 2-Thiophen-2-yl-7-(3-trifluoromethyl-phenyl)-[1,2,4]triazolo[1,5-a]pyridin-5-ylamine | M + H⁺ (100) | 360.4 | 63 |

-continued

| Example No. | Structure | Name | MS m/e (%) | MW | Synthesis according to example No. |
|---|---|---|---|---|---|
| 158 | 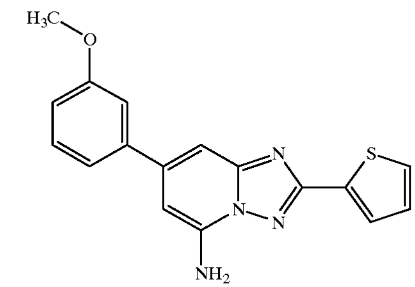 | 7-(3-Methoxy-phenyl)-2-thiophen-2-yl-[1,2,4]triazolo[1,5-a]pyridin-5-ylamine | M + H$^+$(100) | 322.4 | 63 |
| 159 | 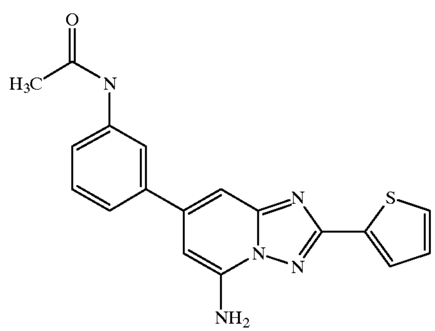 | N-[3-(5-Amino-2-thiophen-2-yl-[1,2,4]triazolo[1,5-a]pyridin-7-yl)-phenyl]-acetamide | M + H$^+$(100) | 349.4 | 63 |
| 160 | 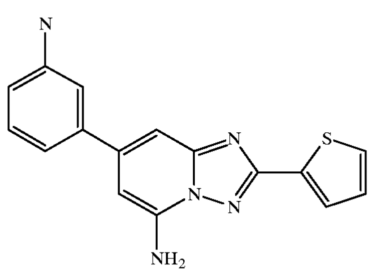 | 7-(3-Amino-phenyl)-2-thiophen-2-yl-[1,2,4]triazolo[1,5-a]pyridin-5-ylamine | M + H$^+$(100) | 307.4 | 63 |

| Example No. | Structure | Name | MS m/e (%) | MW | Synthesis according to example No. |
|---|---|---|---|---|---|
| 161 | 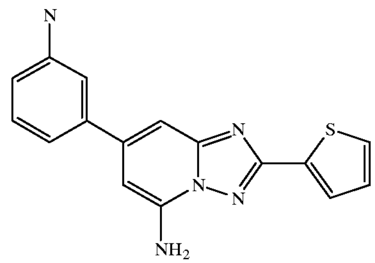 | 7-(4-Dimethylamino-phenyl)-2-thiophen-2-yl-[1,2,4]triazolo[1,5-a]pyridin-5-ylamine | M + H⁺(100) | 335.4 | 63 |
| 162 | 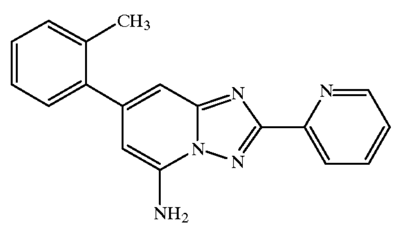 | 2-Pyridin-2-yl-7-o-tolyl-[1,2,4]triazolo[1,5-a]pyridin-5-ylamine | M + H⁺(100) | 301.4 | 92 |
| 163 | 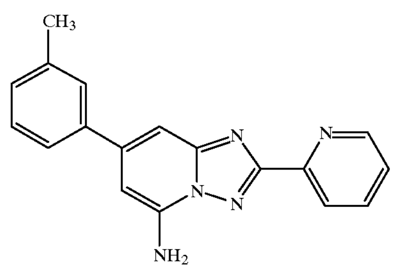 | 2-Pyridin-2-yl-7-m-tolyl-[1,2,4]triazolo[1,5-a]pyridin-5-ylamine | M + H⁺(100) | 301.4 | 92 |
| 164 | 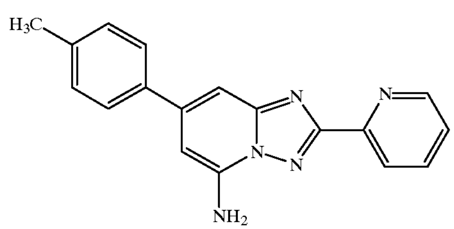 | 2-Pyridin-2-yl-7-p-tolyl-[1,2,4]triazolo[1,5-a]pyridin-5-ylamine | M + H⁺(100) | 301.4 | 92 |

-continued

| Example No. | Structure | Name | MS m/e (%) | MW | Synthesis according to example No. |
|---|---|---|---|---|---|
| 165 | 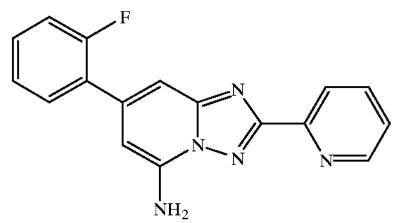 | 7-(2-Fluoro-phenyl)-2-pyridin-2-yl-[1,2,4]triazolo[1,5-a]pyridin-5-ylamine | M + H⁺(100) | 305.3 | 92 |
| 166 | 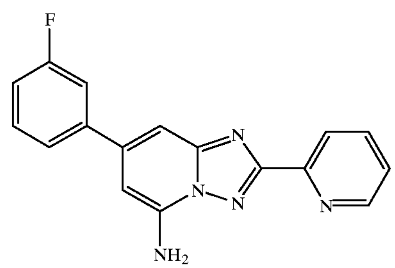 | 7-(3-Fluoro-phenyl)-2-pyridin-2-yl-[1,2,4]triazolo[1,5-a]pyridin-5-ylamine | M + H⁺(100) | 305.3 | 92 |
| 167 | 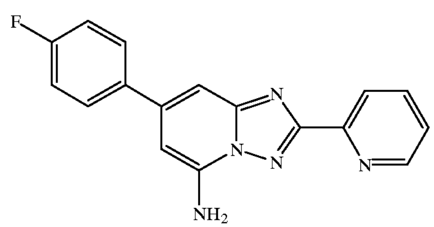 | 7-(4-Fluoro-phenyl)-2-pyridin-2-yl-[1,2,4]triazolo[1,5-a]pyridin-5-ylamine | M + H⁺(100) | 305.3 | 92 |

-continued

| Example No. | Structure | Name | MS m/e (%) | MW | Synthesis according to example No. |
|---|---|---|---|---|---|
| 168 | 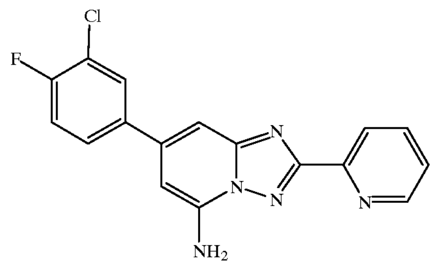 | 7-(3-Chloro-4-fluoro-phenyl)-2-pyridin-2-yl-[1,2,4]triazolo[1,5-a]pyridin-5-ylamine | M+(100) | 339.8 | 92 |
| 169 | 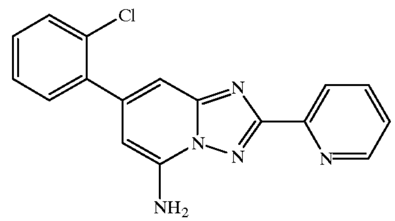 | 7-(2-Chloro-phenyl)-2-pyridin-2-yl-[1,2,4]triazolo[1,5-a]pyridin-5-ylamine | M+(100) | 321.8 | 92 |
| 170 | 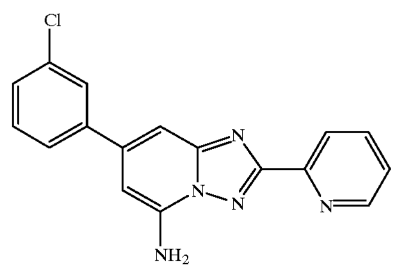 | 7-(3-Chloro-phenyl)-2-pyridin-2-yl-[1,2,4]triazolo[1,5-a]pyridin-5-ylamine | M+(100) | 321.8 | 92 |

-continued

| Example No. | Structure | Name | MS m/e (%) | MW | Synthesis according to example No. |
|---|---|---|---|---|---|
| 171 | 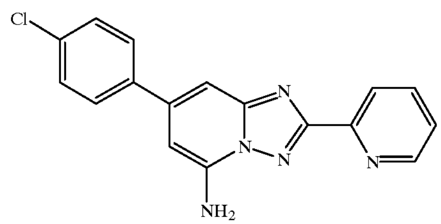 | 7-(4-Chloro-phenyl)-2-pyridin-2-yl-[1,2,4]triazolo[1,5-a]pyridin-5-ylamine | M+(100) | 321.8 | 92 |
| 172 | 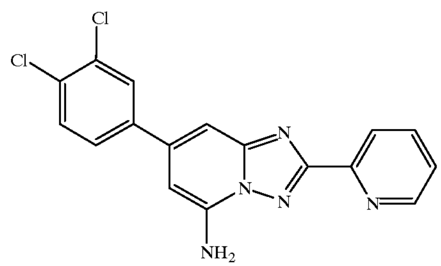 | 7-(3,4-Dichloro-phenyl)-2-pyridin-2-yl-[1,2,4]triazolo[1,5-a]pyridin-5-ylamine | M+(100) | 356.2 | 92 |
| 173 | 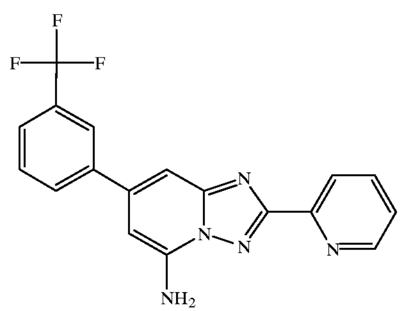 | 2-Pyridin-2-yl-7-(3-trifluoromethyl-phenyl)-[1,2,4]triazolo[1,5-a]pyridin-5-ylamine | M + H+(100) | 355.3 | 92 |

| Example No. | Structure | Name | MS m/e (%) | MW | Synthesis according to example No. |
|---|---|---|---|---|---|
| 174 | 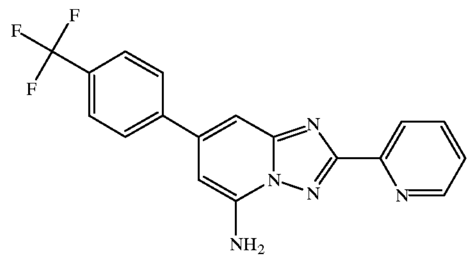 | 2-Pyridin-2-yl-7-(4-trifluoromethyl-phenyl)-[1,2,4]triazolo[1,5-a]pyridin-5-ylamine | M + H⁺(100) | 355.3 | 92 |
| 175 | 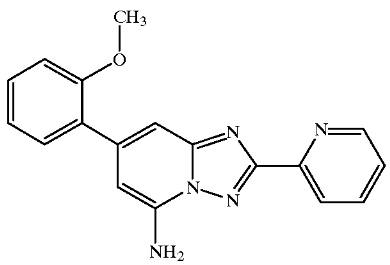 | 7-(2-Methoxy-phenyl)-2-pyridin-2-yl-[1,2,4]triazolo[1,5-a]pyridin-5-ylamine | M + H⁺(100) | 317.4 | 92 |
| 176 | 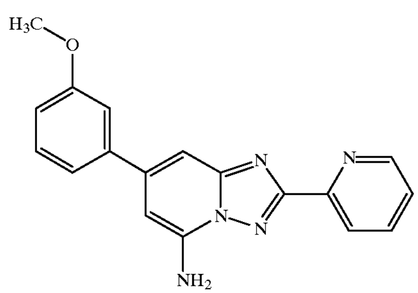 | 7-(3-Methoxy-phenyl)-2-pyridin-2-yl-[1,2,4]triazolo[1,5-a]pyridin-5-ylamine | M + H⁺(100) | 317.4 | 92 |

| Example No. | Structure | Name | MS m/e (%) | MW | Synthesis according to example No. |
|---|---|---|---|---|---|
| 177 | 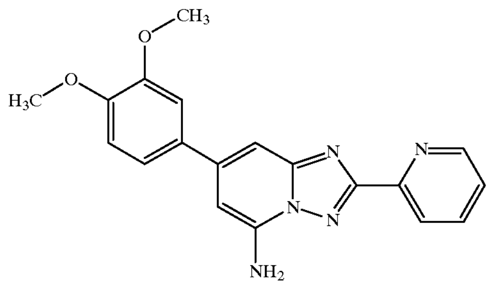 | 7-(3,4-Dimethoxy-phenyl)-2-pyridin-2-yl-[1,2,4]triazolo[1,5-a]pyridin-5-ylamine | M + H⁺(100) | 347.4 | 92 |
| 178 | 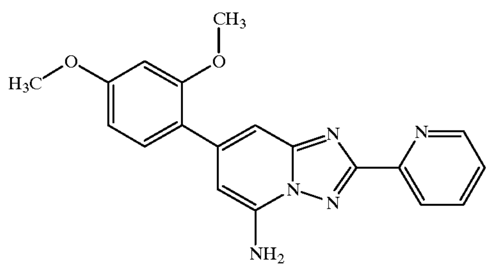 | 7-(2,4-Dimethoxy-phenyl)-2-pyridin-2-yl-[1,2,4]triazolo[1,5-a]pyridin-5-ylamine | M + H⁺(100) | 347.4 | 92 |
| 179 | 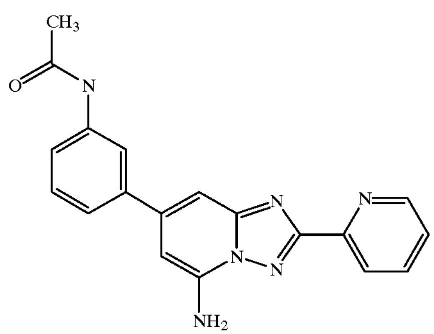 | N-[3-(5-Amino-2-pyridin-2-yl-[1,2,4]triazolo[1,5-a]pyridin-7-yl)-phenyl]-acetamide | M + H⁺(100) | 344.4 | 92 |

| Example No. | Structure | Name | MS m/e (%) | MW | Synthesis according to example No. |
|---|---|---|---|---|---|
| 180 | 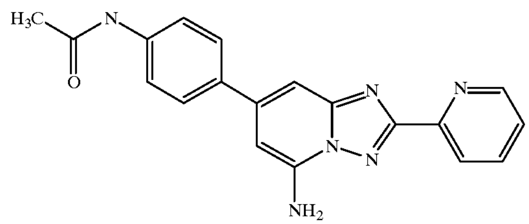 | N-[4-(5-Amino-2-pyridin-2-yl-[1,2,4]triazolo[1,5-a]pyridin-7-yl)-phenyl]-acetamide | M + H⁺(100) | 344.4 | 92 |
| 181 | 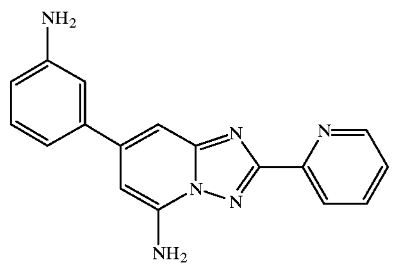 | 7-(3-Amino-phenyl)-2-pyridin-2-yl-[1,2,4]triazolo[1,5-a]pyridin-5-ylamine | M + H⁺(100) | 302.3 | 92 |
| 182 | 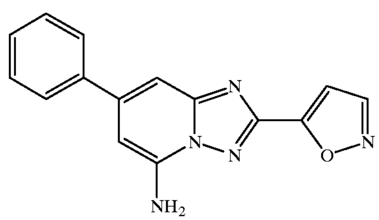 | 2-Isoxazol-5-yl-7-phenyl-[1,2,4]triazolo[1,5-a]pyridin-5-ylamine | M + H⁺(100) | 277.3 | 92 |
| 183 | 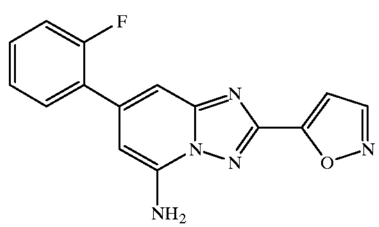 | 7-(2-Fluoro-phenyl)-2-isoxazol-5-yl-[1,2,4]triazolo[1,5-a]pyridin-5-ylamine | M + H⁺(100) | 295.3 | 92 |

-continued

| Example No. | Structure | Name | MS m/e (%) | MW | Synthesis according to example No. |
|---|---|---|---|---|---|
| 184 | 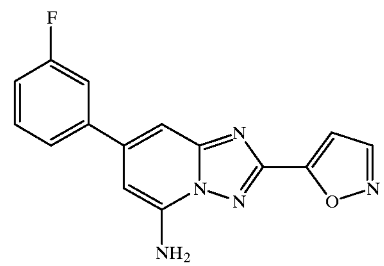 | 7-(3-Fluoro-phenyl)-2-isoxazol-5-yl-[1,2,4]triazolo[1,5-a]pyridin-5-ylamine | M + H$^+$(100) | 295.3 | 92 |
| 185 | 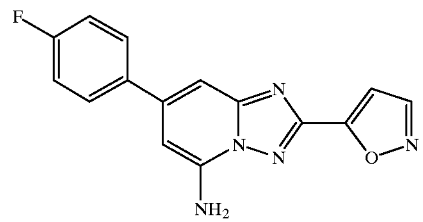 | 7-(4-Fluoro-phenyl)-2-isoxazol-5-yl-[1,2,4]triazolo[1,5-a]pyridin-5-ylamine | M + H$^+$(100) | 295.3 | 92 |
| 186 | 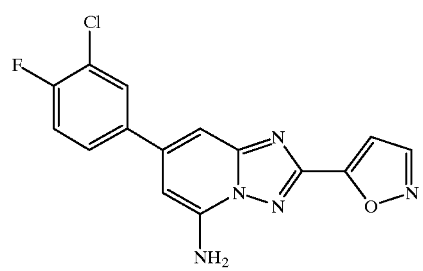 | 7-(3-Chloro-4-fluoro-phenyl)-2-isoxazol-5-yl-[1,2,4]triazolo[1,5-a]pyridin-5-ylamine | M$^+$(100) | 329.7 | 92 |

-continued

| Example No. | Structure | Name | MS m/e (%) | MW | Synthesis according to example No. |
|---|---|---|---|---|---|
| 187 | 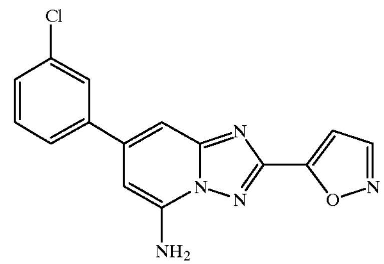 | 7-(3-Chloro-phenyl)-2-isoxazol-5-yl-[1,2,4]triazolo[1,5-a]pyridin-5-ylamine | M+(100) | 311.7 | 92 |
| 188 | 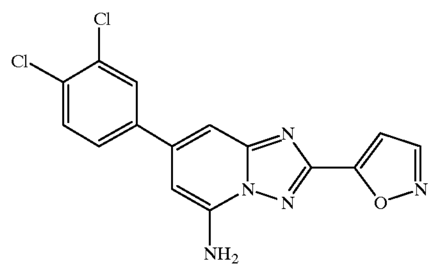 | 7-(3,4-Dichloro-phenyl)-2-isoxazol-5-yl-[1,2,4]triazolo[1,5-a]pyridin-5-ylamine | M+(100) | 346.2 | 92 |
| 189 | 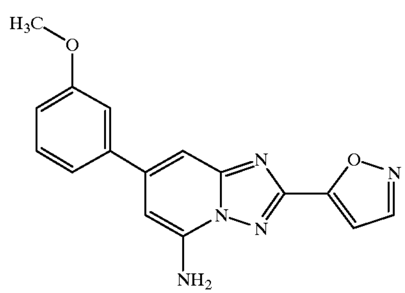 | 2-Isoxazol-5-yl-7-(3-methoxy-phenyl)-[1,2,4]triazolo[1,5-a]pyridin-5-ylamine | M + H+(100) | 307.3 | 92 |

-continued

| Example No. | Structure | Name | MS m/e (%) | MW | Synthesis according to example No. |
|---|---|---|---|---|---|
| 190 | 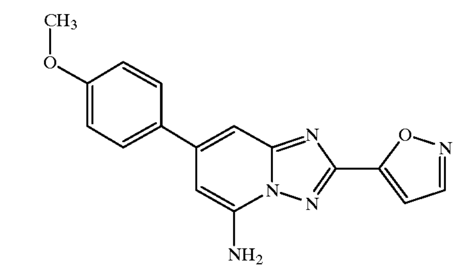 | 2-Isoxazol-5-yl-7-(4-methoxy-phenyl)-[1,2,4]triazolo[1,5-a]pyridin-5-ylamine | M + H⁺(100) | 307.3 | 92 |
| 191 | 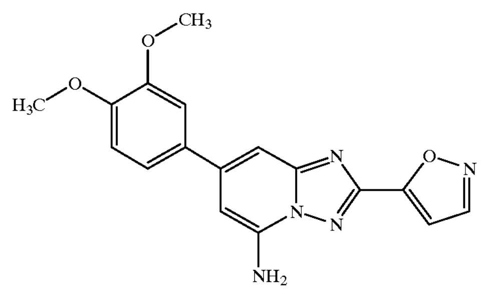 | 7-(3,4-Dimethoxy-phenyl)-2-isoxazol-5-yl-[1,2,4]triazolo[1,5-a]pyridin-5-ylamine | M + H⁺(100) | 337.3 | 92 |
| 192 | 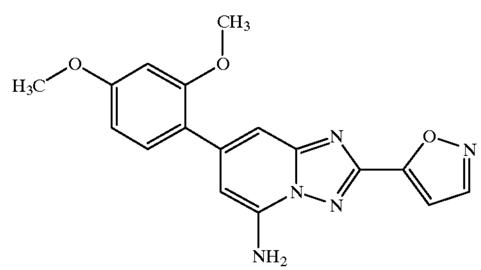 | 7-(2,4-Dimethoxy-phenyl)-2-isoxazol-5-yl-[1,2,4]triazolo[1,5-a]pyridin-5-ylamine | M + H⁺(100) | 337.3 | 92 |

-continued

| Example No. | Structure | Name | MS m/e (%) | MW | Synthesis according to example No. |
|---|---|---|---|---|---|
| 193 | 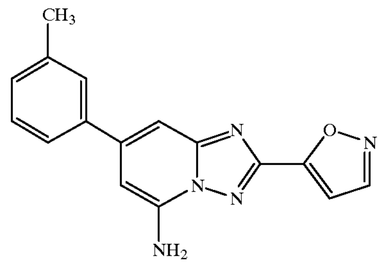 | 2-Isoxazol-5-yl-7-m-tolyl-[1,2,4]triazolo[1,5-a]pyridin-5-ylamine | M + H⁺(100) | 291.3 | 92 |
| 194 | 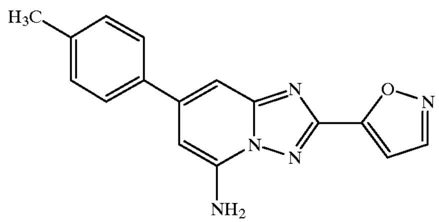 | 2-Isoxazol-5-yl-7-p-tolyl-[1,2,4]triazolo[1,5-a]pyridin-5-ylamine | M + H⁺(100) | 291.3 | 92 |
| 195 | 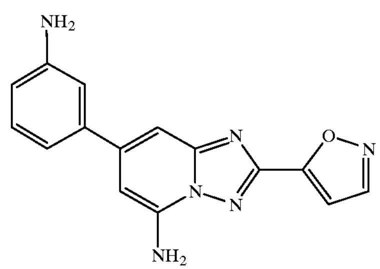 | 7-(3-Amino-phenyl)-2-isoxazol-5-yl-[1,2,4]triazolo[1,5-a]pyridin-5-ylamine | M + H⁺(100) | 292.3 | 92 |

| Example No. | Structure | Name | MS m/e (%) | MW | Synthesis according to example No. |
|---|---|---|---|---|---|
| 196 | 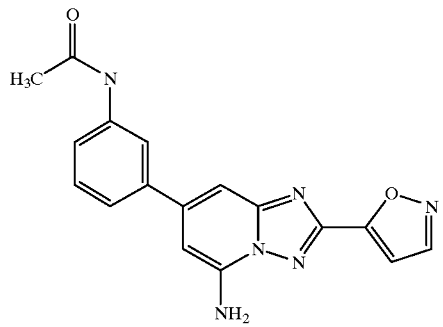 | N-[3-(5-Amino-2-isoxazol-5-yl-[1,2,4]triazolo[1,5-a]pyridin-7-yl)-phenyl]-acetamide | M + H⁺(100) | 334.3 | 92 |
| 197 | 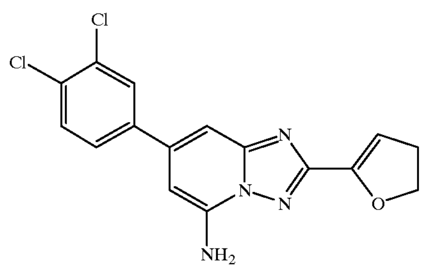 | 7-(3,4-Dichloro-phenyl)-2-(4,5-dihydro-furan-2-yl)-[1,2,4]triazolo[1,5-a]pyridin-5-ylamine | M⁺(100) | 347.2 | 92 |
| 198 | 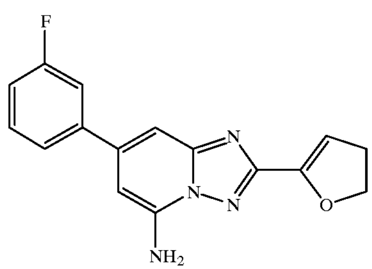 | 2-(4,5-Dihydro-furan-2-yl)-7-(3-fluoro-phenyl)-[1,2,4]triazolo[1,5-a]pyridin-5-ylamine | M + H⁺(100) | 296.3 | 92 |

-continued

| Example No. | Structure | Name | MS m/e (%) | MW | Synthesis according to example No. |
|---|---|---|---|---|---|
| 199 | 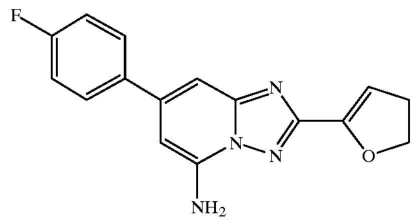 | 2-(4,5-Dihydro-furan-2-yl)-7-(4-fluoro-phenyl)-[1,2,4]triazolo[1,5-a]pyridin-5-ylamine | M + H⁺(100) | 296.3 | 92 |
| 200 | 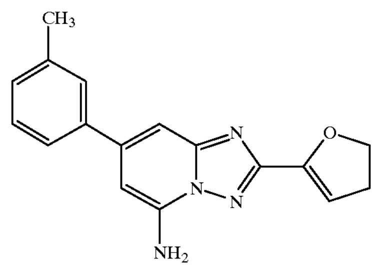 | 2-(4,5-Dihydro-furan-2-yl)-7-m-tolyl-[1,2,4]triazolo[1,5-a]pyridin-5-ylamine | M + H⁺(100) | 292.3 | 92 |
| 201 | 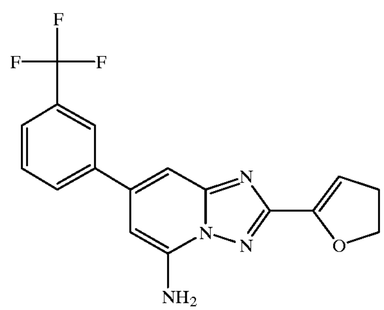 | 2-(4,5-Dihydro-furan-2-yl)-7-(3-tri-fluoromethyl-phenyl)-[1,2,4]tri-azolo[1,5-a]pyridin-5-ylamine | M + H⁺(100) | 346.3 | 92 |

-continued

| Example No. | Structure | Name | MS m/e (%) | MW | Synthesis according to example No. |
|---|---|---|---|---|---|
| 202 | 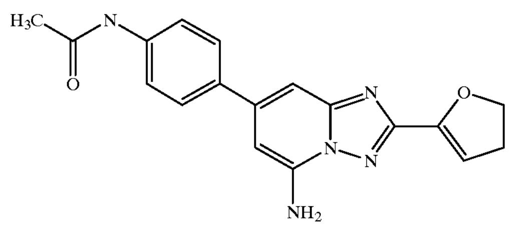 | N-{4-[5-Amino-2-(4,5-dihydro-furan-2-yl)-[1,2,4]triazolo[1,5-a]pyridin-7-yl]-phenyl}-acetamide | M + H⁺(100) | 335.4 | 92 |
| 203 | 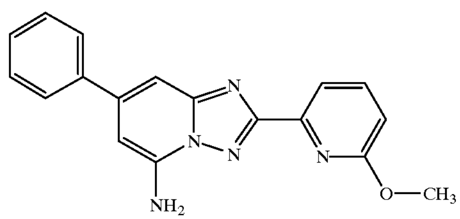 | 2-(6-Methoxy-pyridin-2-yl)-7-phenyl-[1,2,4]triazolo[1,5-a]pyridin-5-ylamine | M + H⁺(100) | 317.4 | 92 |
| 204 | 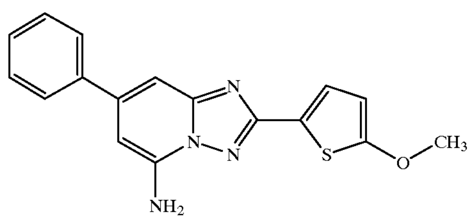 | 2-(5-Methoxy-thiophen-2-yl)-7-phenyl-[1,2,4]triazolo[1,5-a]pyridin-5-ylamine | M + H⁺(100) | 322.4 | 92 |
| 205 | 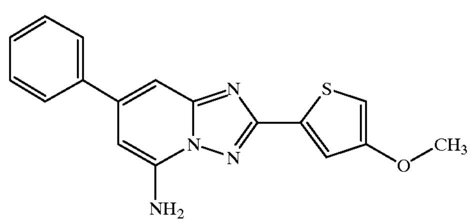 | 2-(4-Methoxy-thiophen-2-yl)-7-phenyl-[1,2,4]triazolo[1,5-a]pyridin-5-ylamine | M + H⁺(100) | 322.4 | 92 |

-continued

| Example No. | Structure | Name | MS m/e (%) | MW | Synthesis according to example No. |
|---|---|---|---|---|---|
| 206 | 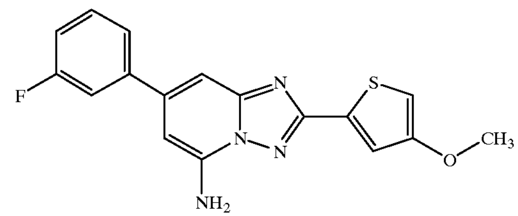 | 7-(3-Fluoro-phenyl)-2-(4-methoxy-thiophen-2-yl)-[1,2,4]triazolo[1,5-a]pyridin-5-ylamine | M + H⁺(100) | 340.4 | 92 |
| 207 | 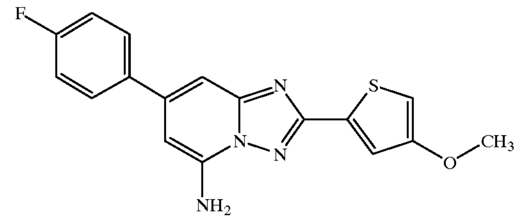 | 7-(4-Fluoro-phenyl)-2-(4-methoxy-thiophen-2-yl)-[1,2,4]triazolo[1,5-a]pyridin-5-ylamine | M + H⁺(100) | 340.4 | 92 |
| 208 | 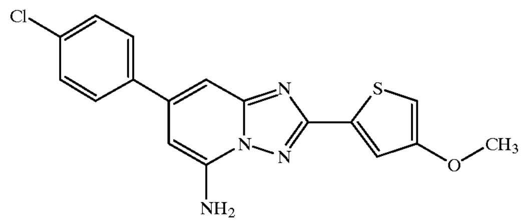 | 7-(4-Chloro-phenyl)-2-(4-methoxy-thiophen-2-yl)-[1,2,4]triazolo[1,5-a]pyridin-5-ylamine | M⁺(100) | 356.8 | 92 |
| 209 | 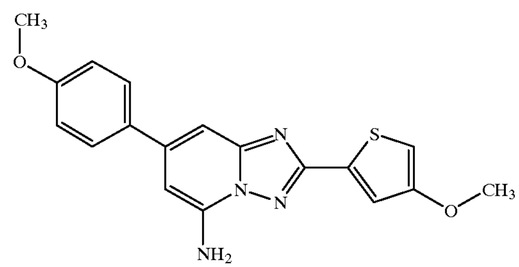 | 7-(4-Methoxy-phenyl)-2-(4-methoxy-thiophen-2-yl)-[1,2,4]triazolo[1,5-a]pyridin-5-ylamine | M + H⁺(100) | 352.4 | 92 |

| Example No. | Structure | Name | MS m/e (%) | MW | Synthesis according to example No. |
|---|---|---|---|---|---|
| 210 | 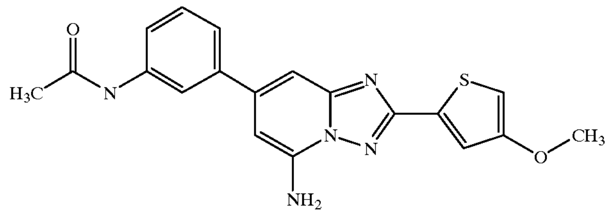 | N-{3-[5-Amino-2-(4-methoxy-thiophen-2-yl)-[1,2,4]triazolo[1,5-a]pyridin-7-yl]-phenyl}-acetamide | M + H⁺ (100) | 379.4 | 92 |
| 211 | 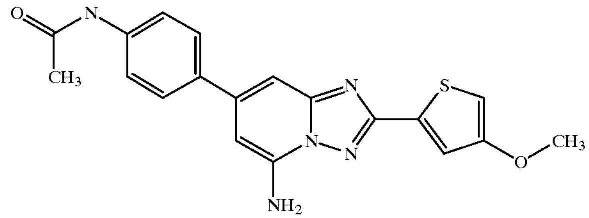 | N-{4-[5-Amino-2-(4-methoxy-thiophen-2-yl)-[1,2,4]triazolo[1,5-a]pyridin-7-yl]-phenyl}-acetamide | M + H⁺ (100) | 379.4 | 92 |
| 212 | 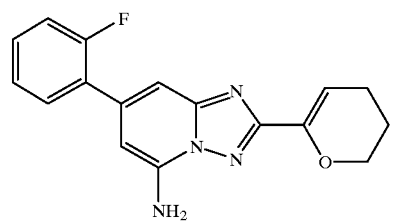 | 2-(5,6-Dihydro-4H-pyran-2-yl)-7-(2-fluoro-phenyl)-[1,2,4]triazolo[1,5-a]pyridin-5-ylamine | M + H⁺ (100) | 310.3 | 92 |
| 213 | 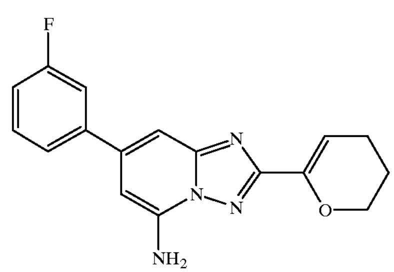 | 2-(5,6-Dihydro-4H-pyran-2-yl)-7-(3-fluoro-phenyl)-[1,2,4]triazolo[1,5-a]pyridin-5-ylamine | M + H⁺ (100) | 310.3 | 92 |

-continued

| Example No. | Structure | Name | MS m/e (%) | MW | Synthesis according to example No. |
|---|---|---|---|---|---|
| 214 | 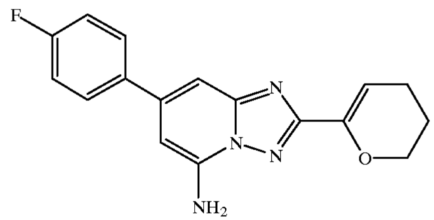 | 2-(5,6-Dihydro-4H-pyran-2-yl)-7-(4-fluoro-phenyl)-[1,2,4]triazolo[1,5-a]pyridin-5-ylamine | M + H⁺(100) | 310.3 | 92 |
| 215 | 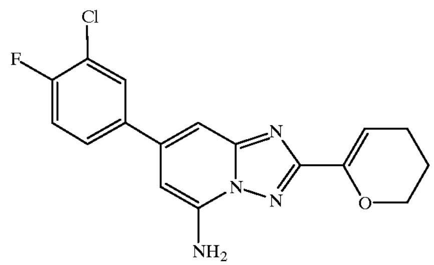 | 7-(3-Chloro-4-fluoro-phenyl)-2-(5,6-dihydro-4H-pyran-2-yl)-[1,2,4]triazolo[1,5-a]pyridin-5-ylamine | M⁺(100) | 344.8 | 92 |
| 216 | 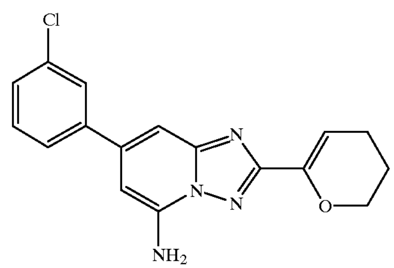 | 7-(3-Chloro-phenyl)-2-(5,6-dihydro-4H-pyran-2-yl)-[1,2,4]triazolo[1,5-a]pyridin-5-ylamine | M⁺(100) | 326.8 | 92 |
| 217 | 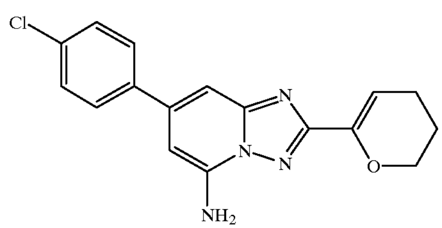 | 7-(4-Chloro-phenyl)-2-(5,6-dihydro-4H-pyran-2-yl)-[1,2,4]triazolo[1,5-a]pyridin-5-ylamine | M⁺(100) | 326.8 | 92 |

| Example No. | Structure | Name | MS m/e (%) | MW | Synthesis according to example No. |
|---|---|---|---|---|---|
| 218 | 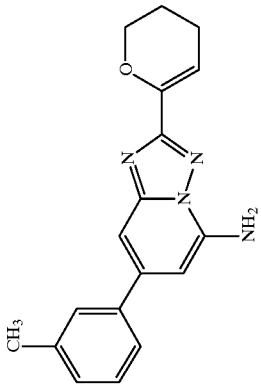 | 2-(5,6-Dihydro-4H-pyran-2-yl)-7-m-tolyl-[1,2,4]triazolo[1,5-a]pyridin-5-ylamine | M + H⁺(100) | 306.4 | 92 |
| 219 | 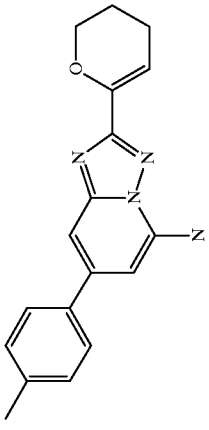 | 2-(5,6-Dihydro-4H-pyran-2-yl)-7-p-tolyl-[1,2,4]triazolo[1,5-a]pyridin-5-ylamine | M + H⁺(100) | 306.4 | 92 |
| 220 | 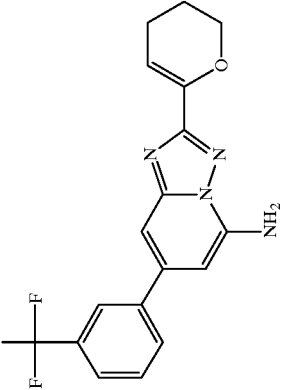 | 2-(5,6-Dihydro-4H-pyran-2-yl)-7-(3-trifluoromethyl-phenyl)-[1,2,4]triazolo[1,5-a]pyridin-5-ylamine | M + H⁺(100) | 360.3 | 92 |

EXAMPLE 221

7-Morpholin-4-yl-2-phenyl-[1,2,4]triazolo[1,5-a]pyridin-5-ylamine (RO-69-0728/000)

A mixture of 40 mg (0.138 mmol) 7-bromo-2-phenyl-[1,2,4]triazolo[1,5-a]pyridin-5-ylamine, 241 µl (2.8 mmol) morpholin and 225 mg (0.69 mmol) $Cs_2CO_3$ in 200 µl DMF was heated 20 h to 140° C. filtration and subsequent purification with reversed phase column chromatography with an acetonitrile/water gradient yielded 20 mg (49%) of the title compound, MS m/e M+H$^+$ (100%).

According to example 221 triazolopyridine derivatives have been synthesised through the reaction of the appropriate bromide substituted triazolo-pyridine with the respective amine and subsequently isolated with reversed phase column chromatography eluting with an acetonitrile/water gradient. The results are compiled in the following list comprising example 222 example 255. For some examples N-methyl-pyrolidon (NMP) at 160° C. was used instead of DMF at 140°. This is indicated in the following list with the additional comment "NMP" respectively "DMF".

| Example No. | structure | name | MS m/e (%) | MW | condition |
|---|---|---|---|---|---|
| 222 | 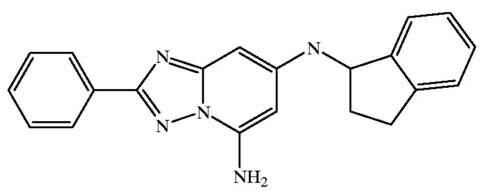 | N7-Indan-1-yl-2-phenyl-[1,2,4]triazolo[1,5-a]pyridine-5,7-diamine | M + H$^+$(100) | 341.4 | NMP |
| 223 | 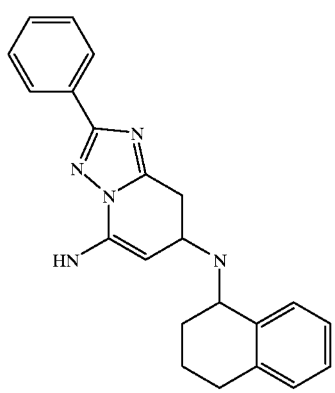 | 2-Phenyl-N7-(1,2,3,4-tetrahydro-naphthalen-1-yl)-[1,2,4]triazolo[1,5-a]pyridine-5,7-diamine | M + H$^+$(100) | 355.4 | NMP |
| 224 | 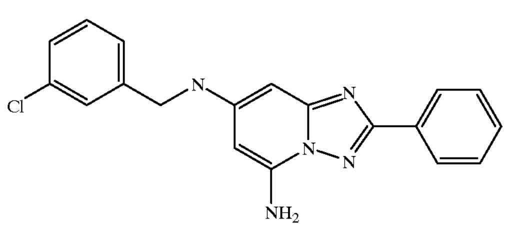 | N7-(3-Chloro-benzyl)-2-phenyl-[1,2,4]triazolo[1,5-a]pyridine-5,7-diamine | M$^+$(100) | 349.8 | NMP |
| 225 | 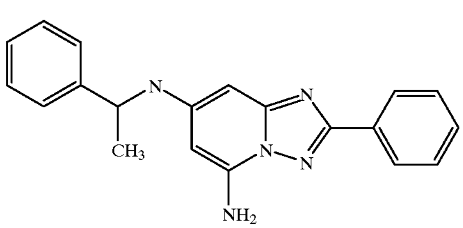 | 2-Phenyl-N7-(1-phenyl-ethyl)-[1,2,4]triazolo[1,5-a]pyridine-5,7-diamine | M + H$^+$(100) | 329.4 | NMP |

| Example No. | structure | name | MS m/e (%) | MW | condition |
|---|---|---|---|---|---|
| 226 | 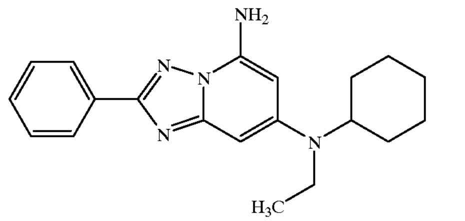 | N7-Cyclohexyl-N7-ethyl-2-phenyl-[1,2,4]triazolo[1,5-a]pyridine-5,7-diamine | M + H⁺(100) | 335.5 | NMP |
| 227 | 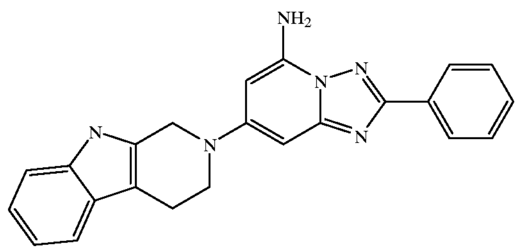 | 2-Phenyl-7-(1,3,4,9-tetrahydro-b-carbolin-2-yl)-[1,2,4]triazolo[1,5-a]pyridin-5-ylamine | M + H⁺(100) | 380.5 | NMP |
| 228 | 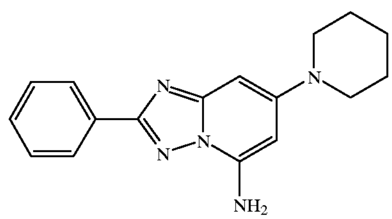 | 2-Phenyl-7-piperidin-1-yl-[1,2,4]triazolo[1,5-a]pyridin-5-ylamine | M + H⁺(100) | 293.4 | NMP |
| 229 | 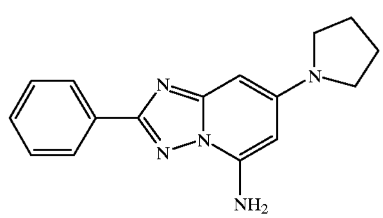 | 2-Phenyl-7-pyrrolidin-1-yl-[1,2,4]triazolo[1,5-a]pyridin-5-ylamine | M + H⁺(100) | 279.3 | NMP |
| 230 | 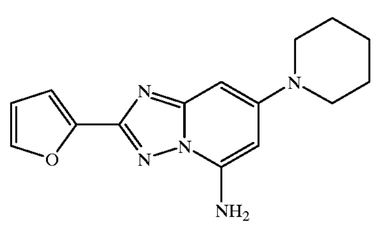 | 2-Furan-2-yl-7-piperidin-1-yl-[1,2,4]triazolo[1,5-a]pyridin-5-ylamine | M + H⁺(100) | 283.3 | NMP |
| 231 | 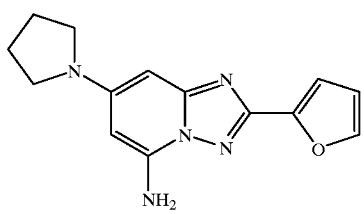 | 2-Furan-2-yl-7-pyrrolidin-1-yl-[1,2,4]triazolo[1,5-a]pyridin-5-ylamine | M + H⁺(100) | 269.3 | NMP |

| Example No. | structure | name | MS m/e (%) | MW | condition |
|---|---|---|---|---|---|
| 232 | 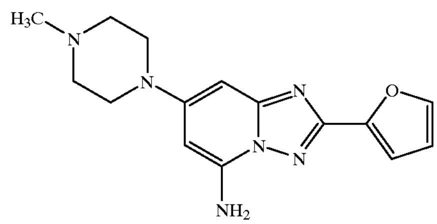 | 2-Furan-2-yl-7-(4-methyl-piperazin-1-yl)-[1,2,4]triazolo[1,5-a]pyridin-5-ylamine | M + H⁺(100) | 298.4 | NMP |
| 233 | 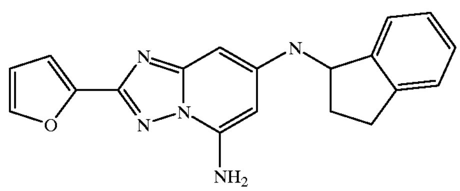 | 2-Furan-2-yl-N7-indan-1-yl-[1,2,4]triazolo[1,5-a]pyridine-5,7-diamine | M + H⁺(100) | 331.4 | NMP |
| 234 | 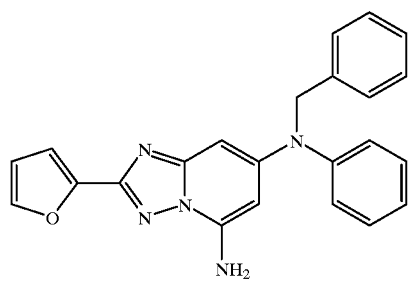 | 2-Furan-2-yl-N7-(4-methoxy-benzyl)-[1,2,4]triazolo[1,5-a]pyridine-5,7-diamine | M + H⁺(100) | 335.4 | NMP |
| 235 | 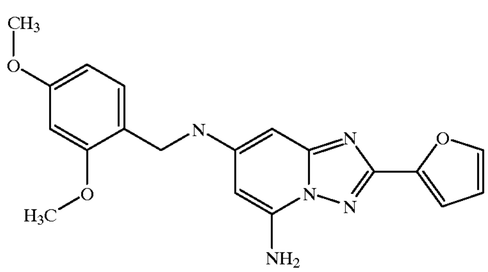 | N7-(2,4-Dimethoxy-benzyl)-2-furan-2-yl-[1,2,4]triazolo[1,5-a]pyridine-5,7-diamine | M + H⁺(100) | 365.4 | NMP |
| 236 | 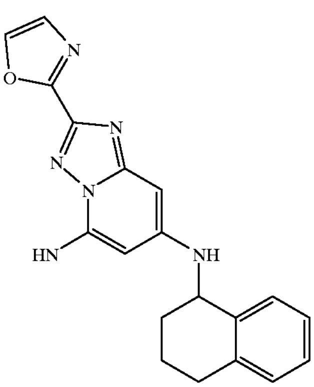 | 2-Furan-2-yl-N7-(1,2,3,4-tetrahydro-naphthalen-1-yl)-[1,2,4]triazolo[1,5-a]pyridine-5,7-diamine | M + H⁺(100) | 345.4 | NMP |

| Example No. | structure | name | MS m/e (%) | MW | condition |
|---|---|---|---|---|---|
| 237 | 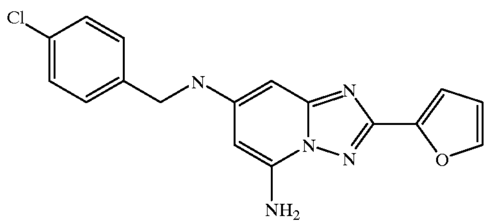 | N7-(4-Chloro-benzyl)-2-furan-2-yl-[1,2,4]triazolo[1,5-a]pyridine-5,7-diamine | M⁺(100) | 339.8 | NMP |
| 238 | 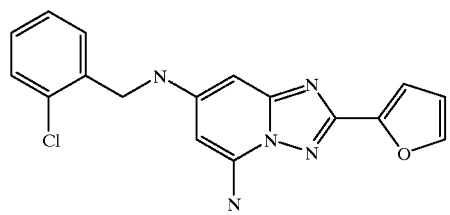 | N7-(2-Chloro-benzyl)-2-furan-2-yl-[1,2,4]triazolo[1,5-a]pyridine-5,7-diamine | M⁺(100) | 339.8 | NMP |
| 239 | 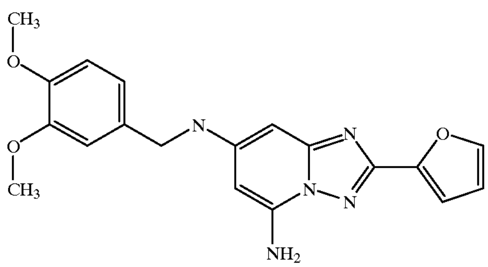 | N7-(3,4-Dimethoxy-benzyl)-2-furan-2-yl-[1,2,4]triazolo[1,5-a]pyridine-5,7-diamine | M + H⁺(100) | 365.4 | NMP |
| 240 | 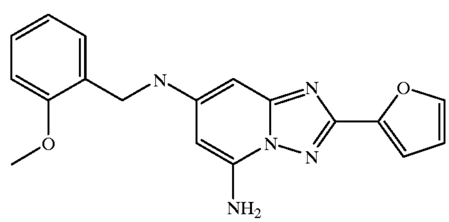 | 2-Furan-2-yl-N7-(2-methoxy-benzyl)-[1,2,4]triazolo[1,5-a]pyridine-5,7-diamine | M + H⁺(100) | 335.4 | NMP |
| 241 | 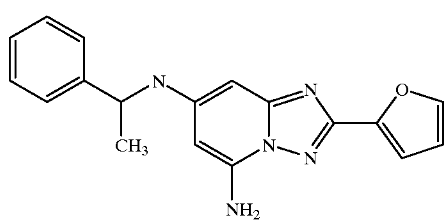 | 2-Furan-2-yl-N7-(1-phenyl-ethyl-[1,2,4]triazolo[1,5-a]pyridine-5,7-diamine | M + H⁺(100) | 319.4 | NMP |
| 242 | 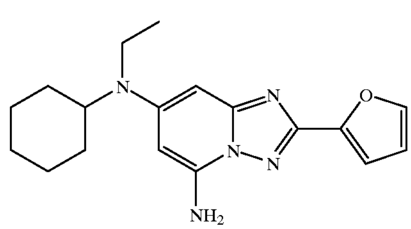 | N7-Cyclohexyl-N7-ethyl-2-furan-2-yl-[1,2,4]triazolo[1,5-a]pyridine-5,7-diamine | M + H⁺(100) | 325.4 | NMP |

-continued

| Example No. | structure | name | MS m/e (%) | MW | condition |
|---|---|---|---|---|---|
| 243 | 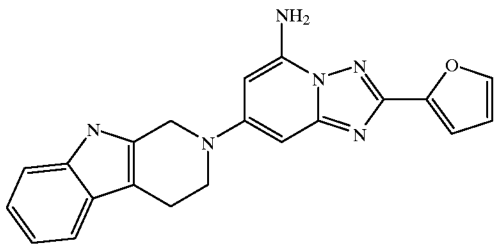 | 2-Furan-2-yl-7-(1,3,4,9-tetrahydro-b-carbolin-2-yl)-[1,2,4]triazolo[1,5-a]pyridin-5-ylamine | M + H⁺(100) | 370.4 | NMP |
| 244 | 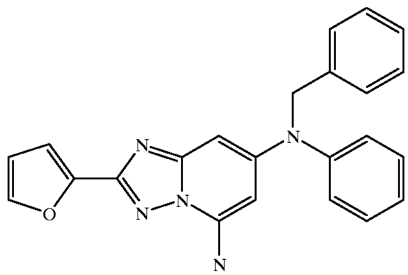 | N7-Benzyl-2-furan-2-yl-N7-phenyl-[1,2,4]triazolo[1,5-a]pyridine-5,7-diamine | M + H⁺(100) | 381.4 | NMP |
| 245 | 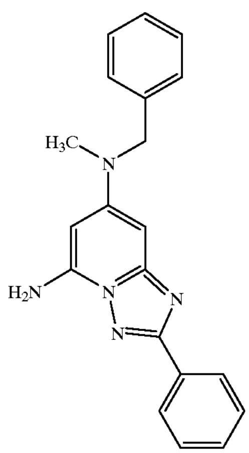 | N7-Benzyl-N7-methyl-2-phenyl-[1,2,4]triazolo[1,5-a]pyridine-5,7-diamine | M + H⁺(100) | 329.4 | DMF |
| 246 | 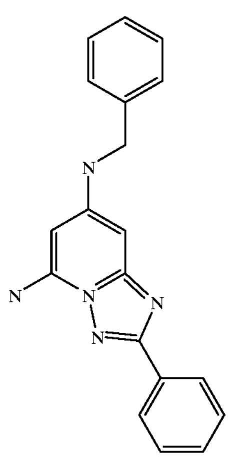 | N7-Benzyl-2-phenyl-[1,2,4]triazolo[1,5-a]pyridine-5,7-diamine | M + H⁺(100) | 315.4 | DMF |

-continued

| Example No. | structure | name | MS m/e (%) | MW | condition |
|---|---|---|---|---|---|
| 247 | 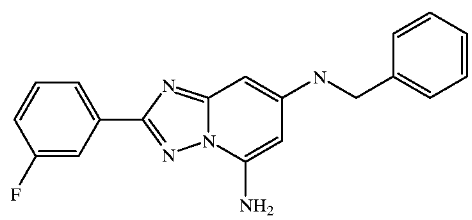 | N7-Benzyl-2-(3-fluoro-phenyl)-[1,2,4]triazolo[1,5-a]pyridine-5,7-diamine | M + H⁺(100) | 333.4 | NMP |
| 248 | 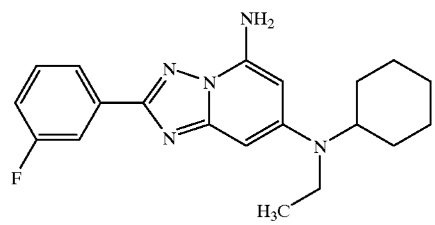 | N7-Cyclohexyl-N7-ethyl-2-(3-fluoro-phenyl)-[1,2,4]triazolo[1,5-a]pyridine-5,7-diamine | M + H⁺(100) | 353.4 | NMP |
| 249 | 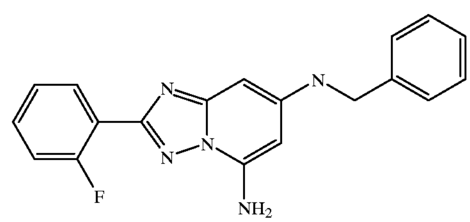 | N7-Benzyl-2-(2-fluoro-phenyl)-[1,2,4]triazolo[1,5-a]pyridine-5,7-diamine | M + H⁺(100) | 333.4 | NMP |
| 250 | 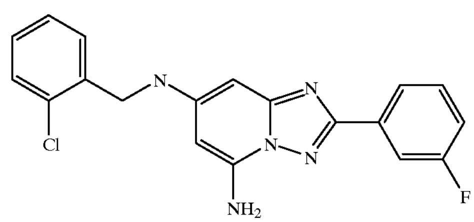 | N7-(2-Chloro-benzyl)-2-(3-fluoro-phenyl)-[1,2,4]triazolo[1,5-a]pyridine-5,7-diamine | M⁺(100) | 367.8 | NMP |
| 251 | 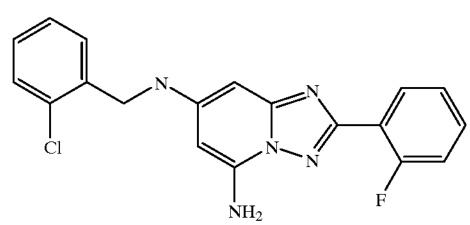 | N7-(2-Chloro-benzyl)-2-(2-fluoro-phenyl)-[1,2,4]triazolo[1,5-a]pyridine-5,7-diamine | M⁺(100) | 367.8 | NMP |
| 252 | 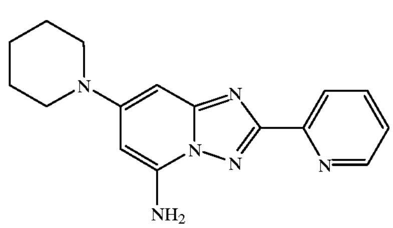 | 7-Piperidin-1-yl-2-pyridin-2-yl-[1,2,4]triazolo[1,5-a]pyridin-5-ylamine | M + H⁺(100) | 294.4 | NMP |

-continued

| Example No. | structure | name | MS m/e (%) | MW | condition |
|---|---|---|---|---|---|
| 253 | 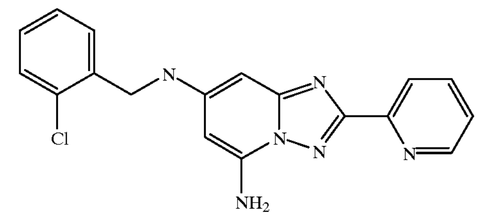 | N7-(2-Chloro-benzyl)-2-pyridin-2-yl-[1,2,4]triazolo[1,5-a]pyridine-5,7-diamine | M⁺(100) | 350.8 | NMP |
| 254 | 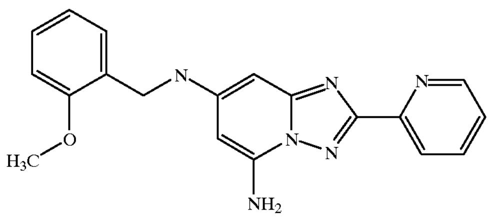 | N7-(2-Methoxy-benzyl)-2-pyridin-2-yl-[1,2,4]triazolo[1,5-a]pyridine-5,7-diamine | M + H⁺(100) | 346.4 | NMP |
| 255 | 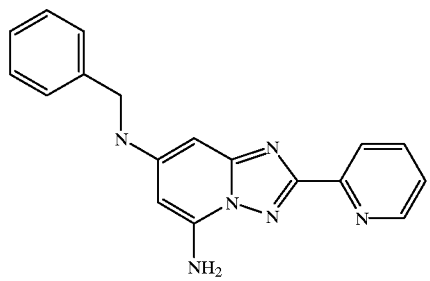 | N7-Benzyl-2-pyridin-2-yl-[1,2,4]triazolo[1,5-a]pyridine-5,7-diamine | M + H⁺(100) | 316.4 | NMP |

EXAMPLE 256

2-Furan-2-yl-7-(4-methoxy-phenoxy)-[1,2,4]triazolo[1,5-a]pyridin-5-ylamine

A mixture of 1 eq. 7-bromo-2-furan-2-yl-[1,2,4]triazolo[1,5-a]pyridin-5-ylamine, 5 eq. p-methoxy-phenol and a catalytic amount of $Cs_2CO_3$ in 200 µl N-methyl-pyrrolidon was heated for 2 h to 160°. The mixture was, after filtration, purified with reversed phase column chromatography eluting with an acetonitrile/water gradient yielding the title compound, MS m/e (%): 322 M+H⁺ (100%).

EXAMPLE 257

7-(4-Bromo-phenoxy)-2-furan-2-yl-[1,2,4]triazolo[1,5-a]pyridin-5-ylamine

A mixture of 1 eq. 7-bromo-2-furan-2-yl-[1,2,4]triazolo[1,5-a]pyridin-5-ylamine, 5 eq. p-bromo-phenol and a catalytic amount of $Cs_2CO_3$ in 200 µl N-methyl-pyrrolidon was heated for 2 h to 160°. The mixture was, after filtration, purified with reversed phase column chromatography eluting with an acetonitrile/water gradient yielding the title compound, MS m/e (%): 371 M⁺ (100%).

EXAMPLE 258

2-Furan-2-yl-7-(5,6,7,8-tetrahydro-naphthalen-1-yloxy)-[1,2,4]triazolo[1,5-a]pyridin-5-ylamine A mixture of 1 eq. 7-bromo-2-furan-2-yl-[1,2,4]triazolo[1,5-a]pyridin-5-ylamine, 5 eq. 5,6,7,8-tetrahydro-naphthalen-1-ol and a catalytic amount of $Cs_2CO_3$ in 200 µl N-methyl-pyrrolidon was heated for 2 h to 160°. The mixture was, after filtration, purified with reversed phase column chromatography eluting with an acetonitrile/water gradient yielding the title compound, MS m/e (%): 346 M+H⁺ (100%).

EXAMPLE 259

2-Furan-2-yl-7-p-tolyloxy-[1,2,4]triazolo[1,5-a]pyridin-5-ylamine (RO-69-2954/000)

A mixture of 1 eq. 7-bromo-2-furan-2-yl-[1,2,4]triazolo[1,5-a]pyridin-5-ylamine, 5 eq. p-methyl-phenol and a catalytic amount of $CsCO_3$ in 200 µl N-methyl-pyrrolidon was heated for 2 h to 160°. The mixture was, after filtration, purified with reversed phase column chromatography eluting with an acetonitrile/water gradient yielding the title compound, MS m/e (%): 306 M+H⁺ (100%).

EXAMPLE 260

7-(3-Fluoro-phenoxy)-2-furan-2-yl-[1,2,4]triazolo[1,5-a]pyridin-5-ylamine

A mixture of 1 eq. 7-bromo-2-furan-2-yl-[1,2,4]triazolo[1,5-a]pyridin-5-ylamine fluoro-phenol and a catalytic amount of $Cs_2CO_3$ in 200 µl N-methyl-pyrrolidon was heated for 2 h to 160°. The mixture was, after filtration, purified with reversed phase column chromatography eluting with an acetonitrile/water gradient yielding the title compound, MS m/e (%): 310 M+H⁺ (100%).

EXAMPLE 261

2-Furan-2-yl-7-(5,6,7,8-tetrahydro-naphthalen-2-yloxy)-[1,2,4]triazolo[1,5-a]pyridin-5-ylamine A mixture of 1 eq. 7-bromo-2-furan-2-)yl-[1,2,4]triazolo[1,5-a]pyridin-5-ylamine, 5 eq. 5,6,7,8-tetrahydro-naphthalen-2-ol and a catalytic amount of $Cs_2CO_3$ in 200 µl N-methyl-pyrrolidon was heated for 2 h to 160°. The mixture was, after filtration, purified with reversed phase column chromatography eluting with an acetonitrile/water gradient yielding the title compound, MS m/e (%): 346 M+H$^+$ (100%).

EXAMPLE 262

7-(6-Methyl-pyridin-2-ylmethoxy)-2-pyridin-2-yl-[1,2,4]triazolo[1,5-a]pyridin-5-ylamine A mixture of 1 eq. 7-bromo-2-pyridin-2-yl-[1,2,4]triazolo[1,5-a]pyridin-5-ylamine, 5 eq. (6-methyl-pyridin-2-yl)-methanol and a catalytic amount of $Cs_2CO_3$ in 200 µl N-methyl-pyrrolidon was heated for 2 h to 160°. The mixture was, after filtration, purified with reversed phase column chromatography eluting with an acetonitrile/water gradient yielding the title compound, MS m/e (%): 332 M+H$^+$ (100%).

EXAMPLE 263

7-Phenoxy-2-pyridin-2-yl-[1,2,4]triazolo[1,5-a]pyridin-5-ylamine

A mixture of 1 eq. 7-bromo-2-pyridin-2-yl-[1,2,4]triazolo[1,5-a]pyridin-5-ylamine, 5 eq. phenol and a catalytic amount of $Cs_2CO_3$ in 200 µl N-methyl-pyrrolidon was heated for 2 h to 160°. The mixture was, after filtration, purified with reversed phase column chromatography eluting with an acetonitrile/water gradient yielding the title compound, MS m/e (%): 303 M+H$^+$ (100%).

EXAMPLE 264

4-(3,4-Dichloro-phenyl)-pyridine-2,6-diamine

A mixture of 40.5 mg (0.21 mmol) 2,6-diamino-4-bromo-pyridine, 90.5 mg (0.47 mmol) 3,4-dichloro-phenyl-boronic acid, 7.8 mg (0.01 mmol) Dichloro(1,1'-bis(diphenylphosphino) ferrocene)palladium (II) dichloromethane adduct and 0.3 ml 2M $Na_2CO_3$ in 1 ml dimethoxyethane was heated to 80° C. for 17 h. The mixture was filtered over silica washed with MeOH/DCM and concentrated. The residue was taken up in 1 ml DMF and the totle compound was purified by reversed phase column chromatography eluting wit an acetonitrile/water gradient to yield 29 mg (52%), MS m/e (%): 254 M$^+$ (100).

According to the method described in Example 264 further pyridine derivatives were synthesised as intermediates for triazolo-pyridine derivatives. The results are compiled in the following list comprising example 265 to example 300.

| Example No. | Structure | Name | MW | MS m/e (%) |
|---|---|---|---|---|
| 265 | 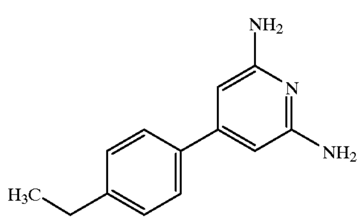 | 4-(4-Ethyl-phenyl)-pyridine-2,6-diamine | 213.3 | M + H$^+$(100) |
| 266 | 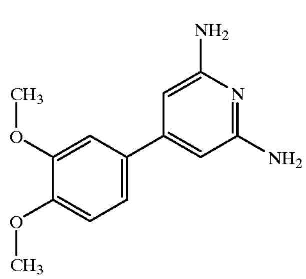 | 4-(3,4-Dimethoxy-phenyl)-pyridine-2,6-diamine | 245.3 | M + H$^+$(100) |

-continued

| Example No. | Structure | Name | MW | MS m/e (%) |
|---|---|---|---|---|
| 267 | 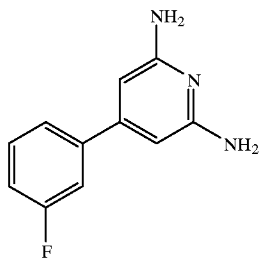 | 4-(3-Fluoro-phenyl)-pyridine-2,6-diamine | 203.2 | M + H⁺(100) |
| 268 | 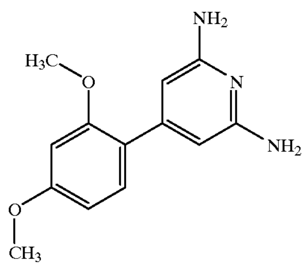 | 4-(2,4-Dimethoxy-phenyl)-pyridine-2,6-diamine | 245.3 | M + H⁺(100) |
| 269 | 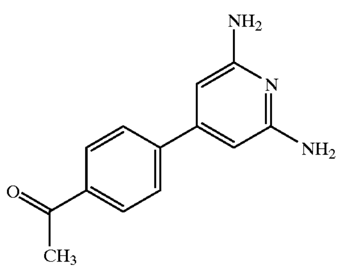 | 1-[4-(2,6-Diamino-pyridin-4-yl)-phenyl]-ethanone | 227.3 | M + H⁺(100) |
| 270 | 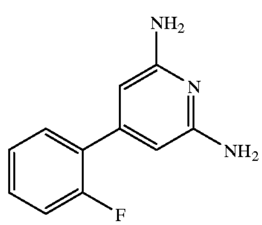 | 4-(2-Fluoro-phenyl)-pyridine-2,6-diamine | 203.2 | M + H⁺(100) |
| 271 | 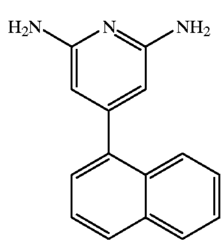 | 4-Naphthalen-1-yl-pyridine-2,6-diamine | 235.3 | M + H⁺(100) |

-continued

| Example No. | Structure | Name | MW | MS m/e (%) |
|---|---|---|---|---|
| 272 | 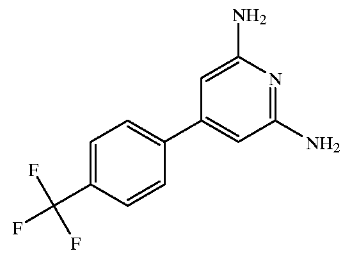 | 4-(4-Trifluoromethyl-phenyl)-pyridine-2,6-diamine | 253.2 | M + H$^+$(100) |
| 273 | 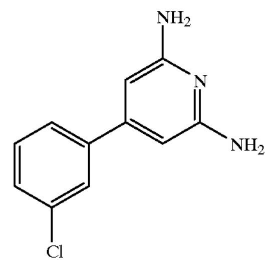 | 4-(3-Chloro-phenyl)-pyridine-2,6-diamine | 219.7 | M$^+$(100) |
| 274 | 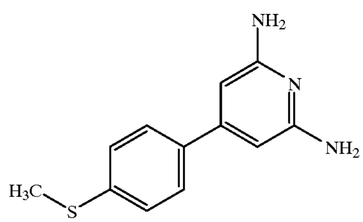 | 4-(4-Methylsulfanyl-phenyl)-pyridine-2,6-diamine | 231.3 | M + H$^+$(100) |
| 275 | 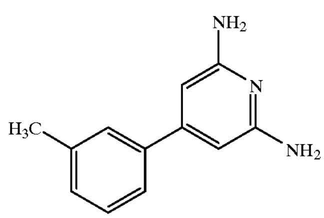 | 4-m-Tolyl-pyridine-2,6-diamine | 199.3 | M + H$^+$(100) |
| 276 | 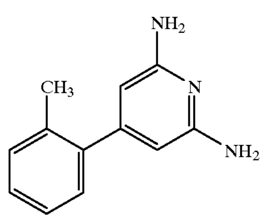 | 4-o-Tolyl-pyridine-2,6-diamine | 199.3 | M + H$^+$(100) |
| 277 | 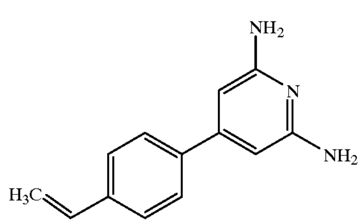 | 4-(4-Vinyl-phenyl)-pyridine-2,6-diamine | 211.3 | M + H$^+$(100) |

-continued

| Example No. | Name | MW | MS m/e (%) |
|---|---|---|---|
| 278 | 4-Thiophen-3-yl-pyridine-2,6-diamine | 191.3 | M + H⁺(100) |
| 279 | 4-(3-Trifluoromethyl-phenyl)-pyridine-2,6-diamine | 253.2 | M + H⁺(100) |
| 280 | 4-(2-Methoxy-phenyl)-pyridine-2,6-diamine | 215.3 | M + H⁺(100) |
| 281 | 4-(4-Methoxy-phenyl)-pyridine-2,6-diamine | 215.3 | M + H⁺(100) |
| 282 | 4-(4-Fluoro-phenyl)-pyridine-2,6-diamine | 203.2 | M + H⁺(100) |
| 283 | 4-(3-Chloro-4-fluoro-phenyl)-pyridine-2,6-diamine | 237.7 | M⁺(100) |

| Example No. | Structure | Name | MW | MS m/e (%) |
|---|---|---|---|---|
| 284 | 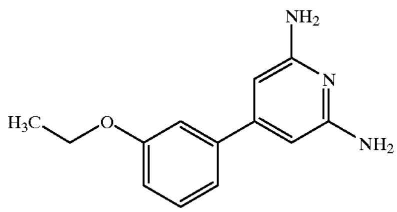 | 4-(3-Ethoxy-phenyl)-pyridine-2,6-diamine | 229.3 | M + H⁺(100) |
| 285 | 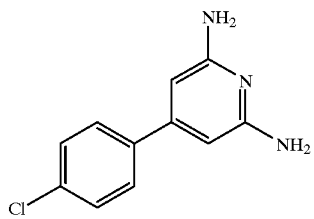 | 4-(4-Chloro-phenyl)-pyridine-2,6-diamine | 219.7 | M⁺(100) |
| 286 | 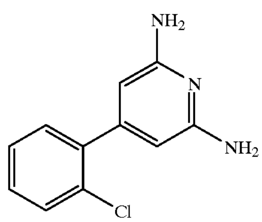 | 4-(2-Chloro-phenyl)-pyridine-2,6-diamine | 219.7 | M⁺(100) |
| 287 | 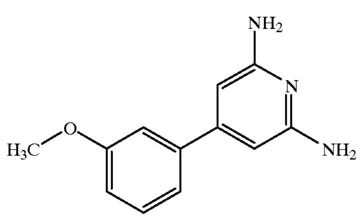 | 4-(3-Methoxy-phenyl)-pyridine-2,6-diamine | 215.3 | M + H⁺(100) |
| 288 | 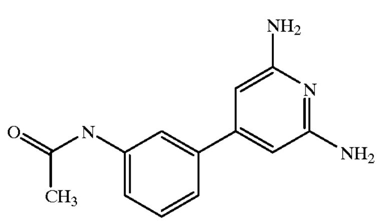 | N-[3-(2,6-Diamino-pyridin-4-yl)-phenyl]-acetamide | 242.3 | M + H⁺(100) |
| 289 | 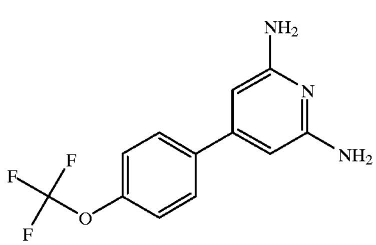 | 4-(4-Trifluoromethoxy-phenyl)-pyridine-2,6-diamine | 269.2 | M + H⁺(100) |

-continued

| Example No. | Structure | Name | MW | MS m/e (%) |
|---|---|---|---|---|
| 290 | 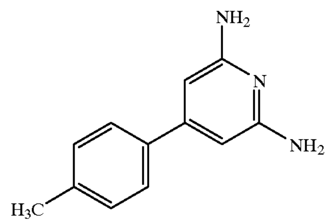 | 4-p-Tolyl-pyridine-2,6-diamine | 199.3 | M + H⁺(100) |
| 291 | 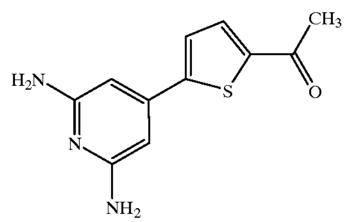 | 1-[5-(2,6-Diamino-pyridin-4-yl)-thiophen-2-yl]-ethanone | 233.3 | M + H⁺(100) |
| 292 | 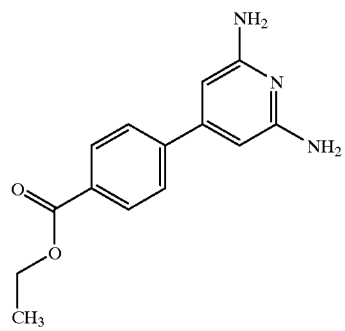 | 4-(2,6-Diamino-pyridin-4-yl)-benzoic acid ethyl ester | 257.3 | M + H⁺(100) |
| 293 | 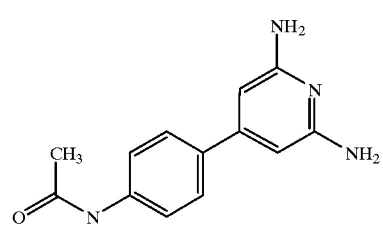 | N-[4-(2,6-Diamino-pyridin-4-yl)-phenyl]-acetamide | 242.3 | M + H⁺(100) |
| 294 | 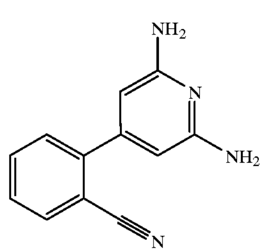 | 2-(2,6-Diamino-pyridin-4-yl)-benzonitrile | 210.2 | M + H⁺(100) |
| 295 | 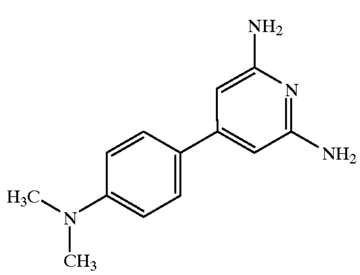 | 4-(4-Dimethylamino-phenyl)-pyridine-2,6-diamine | 228.3 | M + H⁺(100) |

-continued

| Example No. | Structure | Name | MW | MS m/e (%) |
|---|---|---|---|---|
| 296 | 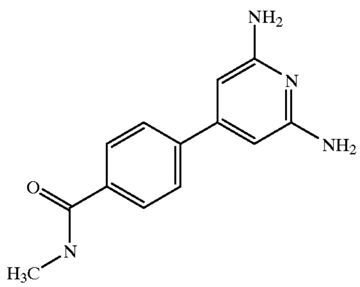 | 4-(2,6-Diamino-pyridin-4-yl)-N-methyl-benzamide | 242.3 | M + H$^+$(100) |
| 297 | 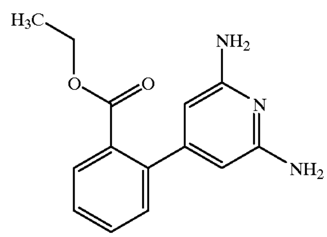 | 2-(2,6-Diamino-pyridin-4-yl)-benzoic acid ethyl ester | 257.3 | M + H$^+$(100) |
| 298 | 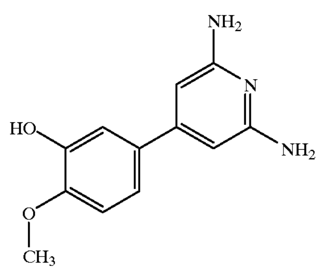 | 5-(2,6-Diamino-pyridin-4-yl)-2-methoxy-phenol | 231.3 | M + H$^+$(100) |
| 299 | 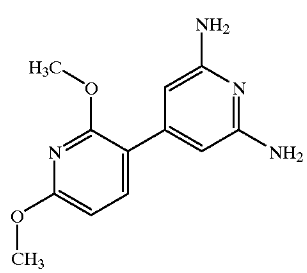 | 2,6-Dimethoxy-[3,4']bipyridinyl-2',6'-diamine | 246.3 | M + H$^+$(100) |
| 300 | 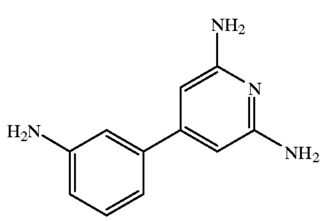 | 4-(3-Amino-phenyl)-pyridine-2,6-diamine | 200.2 | M + H$^+$(100) |

EXAMPLE 301

2-Bromo-furan-2-yl)-7-(3-chloro-phenyl)-[1,2,4]triazolo[1,5-a]pyridin-5-ylamine

To solution of 28.7 mg (0.11 mmol) 4-(3-chloro-phenyl)-pyridine-2,6-diamine in 0.1 ml was added 26.7 mg (0.12 mmol) O-mesitylenesulfonylhydroxylamine (prepared from o-mesitylenesulfonylacetohydroxamate and HClO$_4$ (70%)) in 0.2 ml dioxane at 5° C. and kept 1 h. Upon warming to 50° C. 25.1 mg (0.14 mmol) 5-bromo-2-furaldehyde in 0.25 ml and 0.05 ml 1M KOH in dioxane was added and stirred at 50° C. over night (12 h). The pound was, after addition of formic acid, purified by reversed phase column chromatography eluting with an acetonitrile/water gradient to yield 6.7 mg (15%), MS m/e M+H$^+$ (100).

According to the method described in Example 301 further triazolo-pyridine derivatives were synthesised. The results are compiled in the following list comprising example 302 to example 314.

| Example No. | Structure | Name | MW | MS m/e (%) |
|---|---|---|---|---|
| 302 | 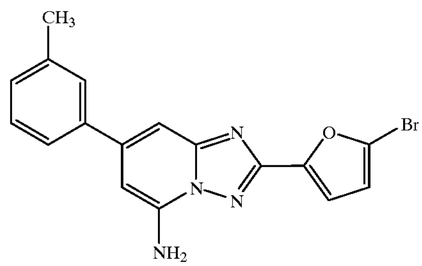 | 2-(5-Bromo-furan-2-yl)-7-m-tolyl-[1,2,4]triazolo[1,5-a]pyridin-5-ylamine | 369.2 | M + H⁺(100) |
| 303 | 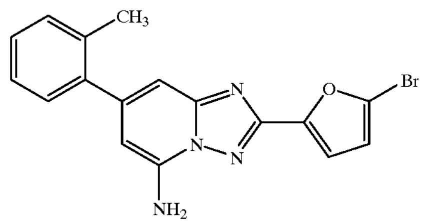 | 2-(5-Bromo-furan-2-yl)-7-o-tolyl-[1,2,4]triazolo[1,5-a]pyridin-5-ylamine | 369.2 | M + H⁺(100) |
| 304 | 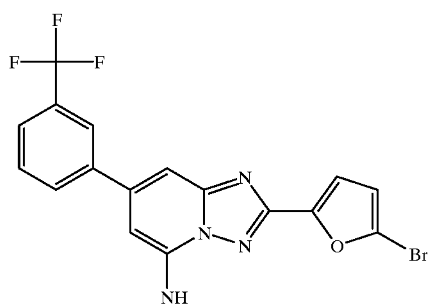 | 2-(5-Bromo-furan-2-yl)-7-(3-trifluoro-methyl-phenyl)-[1,2,4]triazolo[1,5-a]pyridin-5-ylamine | 423.2 | M + H⁺(100) |
| 305 | 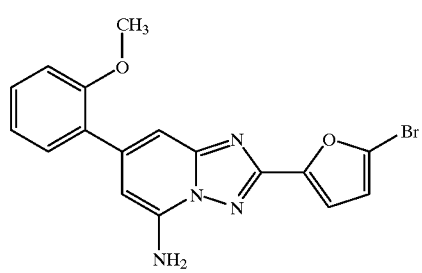 | 2-(5-Bromo-furan-2-yl)-7-(2-methoxy-phenyl)-[1,2,4]triazolo[1,5-a]pyridin-5-ylamine | 385.2 | M + H⁺(100) |
| 306 | 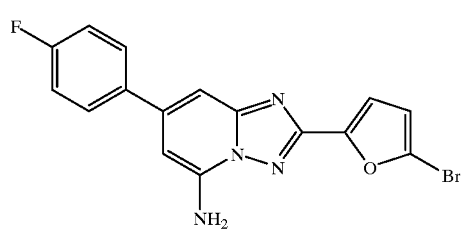 | 2-(5-Bromo-furan-2-yl)-7-(4-fluoro-phenyl)-[1,2,4]triazolo[1,5-a]pyridin-5-ylamine | 373.2 | M + H⁺(100) |

-continued

| Example No. | Structure | Name | MW | MS m/e (%) |
|---|---|---|---|---|
| 307 | 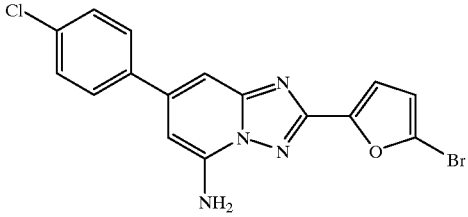 | 2-(5-Bromo-furan-2-yl)-7-(4-chloro-phenyl)-[1,2,4]triazolo[1,5-a]pyridin-5-ylamine | 389.6 | M + H$^+$(100) |
| 308 | 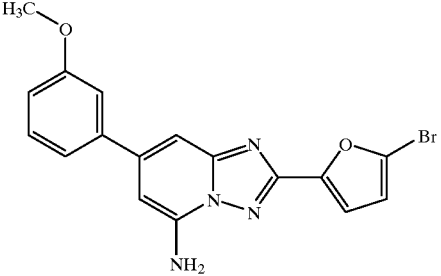 | 2-(5-Bromo-furan-2-yl)-7-(3-methoxy-phenyl)-[1,2,4]triazolo[1,5-a]pyridin-5-ylamine | 385.2 | M + H$^+$(100) |
| 309 | 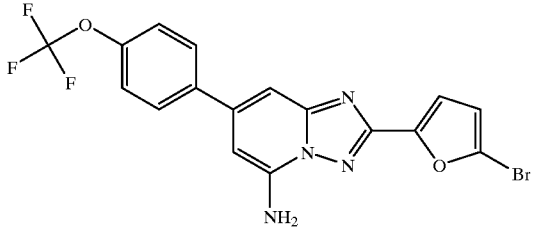 | 2-(5-Bromo-furan-2-yl)-7-(4-trifluoro-methoxy-phenyl)-[1,2,4]triazolo[1,5-a]pyridin-5-ylamine | 439.2 | M + H$^+$(100) |
| 310 | 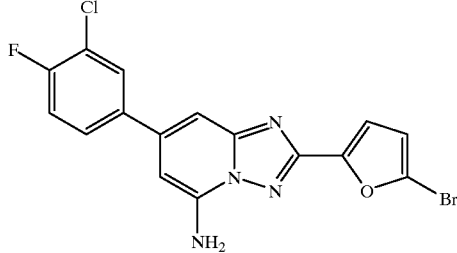 | 2-(5-Bromo-furan-2-yl)-7-(3-chloro-4-fluoro-phenyl)-[1,2,4]triazolo[1,5-a]pyridin-5-ylamine | 407.6 | M + H$^+$(100) |
| 311 | 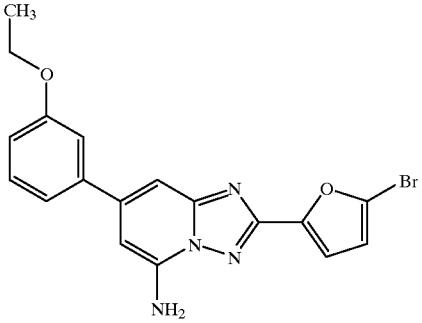 | 2-(5-Bromo-furan-2-yl)-7-(3-ethoxy-phenyl)-[1,2,4]triazolo[1,5-a]pyridin-5-ylamine | 399.3 | M + H$^+$(100) |

-continued

| Example No. | Structure | Name | MW | MS m/e (%) |
|---|---|---|---|---|
| 312 | 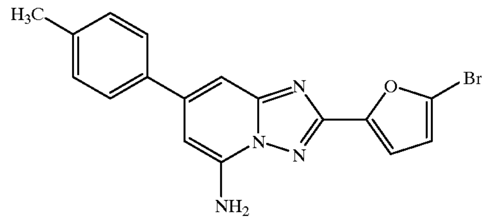 | 2-(5-Bromo-furan-2-yl)-7-p-tolyl-[1,2,4]triazolo[1,5-a]pyridin-5-ylamine | 369.2 | M + H⁺(100) |
| 313 | 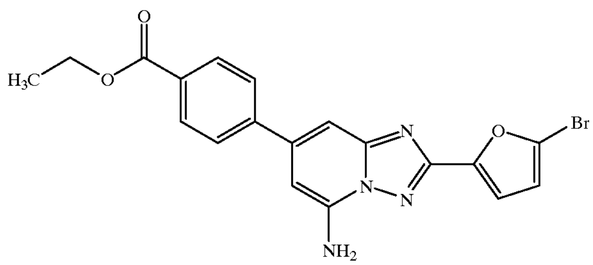 | 4-[5-Amino-2-(5-bromo-furan-2-yl)-[1,2,4]triazolo[1,5-a]pyridin-7-yl]-benzoic acid ethyl ester | 427.3 | M + H⁺(100) |
| 314 | 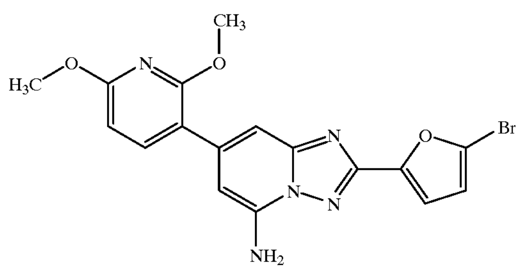 | 2-(5-Bromo-furan-2-yl)-7-(2,6-dimethoxy-pyridin-3-yl)-[1,2,4]triazolo[1,5-a]pyridin-5-ylamine | 416.2 | M + H⁺(100) |

EXAMPLE 315

7-(5-Butyl-pyridin-2-yl)-2-furan-2-yl-[1,2,4]triazolo[1,5-a]pyridin-5-ylamine a) Mixture of (E)- and (Z)-3-(5-butyl-pyridin-2-yl)-acrylonitrile To a suspension of 1.66 g (0.038 mol) sodiumhydride (60% in oil) in 70 ml tetrahydrofurane and 70 ml dimethylformamide were added 21.2 g (0.63 mol) (cyanomethyl)triphenyl-phosphonium chloride. After stirring for 1 hour at room temperature a solution of 6.83 g (0.042 mol) 5-butyl-2-pyridinecarboxaldehyde in 150 ml dioxane were added and stirring was continued for 15 hours. Then 40 ml methanol were added, the solvents were evaporated and the residue chromatographed on silicagel with ethylacetate/hexane 1/4 to yield 4.39 g (56%) (E)/(Z)-3-(5-butyl-pyridin-2-yl)-acrylonitrile as an oil. MS m/e (%): 186 (M⁺, 47), 143 (100).

b) 7-(5-Butyl-pyridin-2-yl)-2-furan-2-yl-[1,2,4]triazolo[1,5-a]pyridin-5-ylamine The title compound, MS m/e (%): 334 (M+H⁺, 100), was prepared in accordance with the general method of example 1 from 3-benzenesulfonylmethyl-5-furan-2-yl-1H-[1,2,4]triazole and (E)-3-(5-butyl-pyridin-2-yl)-acrylonitrile.

EXAMPLE 316

7-(2-Fluoro-pyridin-4-yl)-2-furan-2-yl-[1,2,4]triazolo[1,5-a]pyridin-5-ylamine a) (E) and (Z)-3-(2-Fluoro-pyridin-4-yl)-acrylonitrile To a suspension of 2.80 g (0.038 mol) sodiumhydride (60% in oil) in 120 ml tetrahydrofurane and 120 ml dimethylformamide were added 21.6 g (0.064 mol) (cyanomethyl)triphenyl-phosphonium chloride. After stirring for 1 hour at room temperature a solution of 4.00 g (0.032 mol) 2-fluoro-4-pyridinecarboxaldehyde in 35 ml tetrahydrofurane were added and stirring was continued for 2 days. Then 30 ml methanol were added, the solvents were evaporated and the residue chromatographed on silicagel with ethylacetate/hexane 1/2 to yield 0.45 g (10%) (E)-and (Z)-3-(2-fluoro-pyridin-4-yl)-acrylonitrile as light yellow solid. MS m/e (%): 148 (M⁺, 100), 128 (43).

b) 7-(2-Fluoro-pyridin-4-yl)-2-furan-2-yl-[1,2,4]triazolo[1,5-a]pyridin-5-ylamine The title compound, MS m/e (%): 296 (M+H⁺, 100), was prepared in accordance with the general method of example 1 from 3-benzenesulfonylmethyl-5-furan-2-yl-1H-[1,2,4]triazole and 3-(2-fluoro-pyridin-4-yl)-acrylonitrile.

EXAMPLE 317

7-(5-Chloro-pyridin-2-yl)-2-furan-2-yl-[1,2,4]triazolo[1,5-a]pyridin-5-ylamine a) (E)-3-(5-Chloro-pyridin-2-yl)-acrylonitrile To a suspension of 1.97 g, (0.045 mol) sodiumhydride (60% in oil) in 60 ml tetrahydrofurane and 60 ml dimethylformamide were added 15.25 g (0.045 mol) (cyanomethyl)triphenyl-phosphonium phosphonium chloride. After stirring for 1 hour at room temperature a solution of 6.39 g (0.045 mol) 5-chloro-2-pyridinecarboxaldehyde in 25 ml tetrahydrofurane were added and stirring was continued for 2 days. Then 15 ml methanol were added, the solvents were evaporated and the residue was chromatographed on aluminiumoxide with ethylacetate/hexane 3/7 to yield 4.09 g (55%) (E)-3-(5-chloro-pyridin-2-yl)-acrylonitrile as white solid. MS m/e (%): 164 ($M^{3\circ}$, 100), 137 (17), 113 (45).

b) 7-(5-Chloro-pyridin-2-yl)-2-furan-2-yl-[1,2,4]triazolo[1,5-a]pyridin-5-ylamine The title compound, MS m/e (%): 312 (M+H$^+$, 100), was prepared in accordance with the general method of example 1 from 3-benzenesulfonylmethyl-5-furan-2-yl-1H-[1,2,4]triazole and 3-(5-chloro-pyridin-2-yl)-acrylonitrile.

EXAMPLE 318

2-Furan-2-yl-7-(6-methoxy-pyridin-3-yl)-[1,2,4]triazolo[1,5-a]pyridin-5-ylamine a) (E) and (Z)-3-(6-Methoxy-pyridin-3-yl)-acrylonitrile A mixture of 5.94 g (0.03 mol) 5-bromo-2-methoxypyridine, 2.38 ml (0.036 mol) acrylonitrile, 15.1 ml (0.108 mol) triethylamine and 0.42 g (0.0006 mol) bis(triphenylphosphine)palladium(II)chloride in 120 ml dimethylformamide were stirred at 120° C. for 48 hours. The mixture was extracted with saturated aqueous sodiumbicarbonate solution and dried with sodiumsulfate. Chromatography on silicagel with hexane/ethylacetate 85/15 gave 2.47 g (51%) (E)/(Z)-3-(6-methoxy-pyridin-3-yl)-acrylonitrile as a white solid. MS m/e (%): 160 (M$^+$, 76), 159 (100), 131 (49).

b) 2-Furan-2-yl-7-(6-methoxy-pyridin-3-yl)-[1,2,4]triazolo[1,5-a]pyridin-5-ylamine The title compound, MS m/e (%): 307 (M$^+$, 100), was prepared in accordance with the general method of example 1 from 3-benzenesulfonylmethyl-5-furan-2-yl-1H-[1,2,4]triazole and 3-(6-methoxy-pyridin-2-yl)-acrylonitrile.

EXAMPLE 319

4-(5-Amino-2-furan-2-yl-[1,2,4]triazolo[1,5-a]pyridin-7-yl)-N-phenyl-benzenesulfonamide
(69-0030)

a) 4-(2-Cyano-vinyl)-N-phenyl-benzenesulfonamide

A mixture of 2.88 g (0.009 mol) 4-bromo-N-phenyl-benzenesulfonamide, 0.59 g (0.011 mol) acrylonitrile, 4.65 ml (0.033 mol) triethylamine and 129 g (0.0002 mol) bis(triphenyl-phosphine)palladium(II)chloride in 50 ml dimethylformamide were stirred at 120° C. for 72 hours. The mixture was extracted with saturated aqueous sodiumbicarbonate solution and dried with sodiumsulfate. Chromatography on silicagel with hexane/ethylacetate 7/3 gave 1.73 g (69%) (E)/(Z)-4-(2-cyano-vinyl)-N-phenyl-benzenesulfonamide as a white solid. MS m/e (%):MS m/e (%): 283 (M—H$^-$, 100).

b) 4-(5-Amino-2-furan-2-yl-[1,2,4]triazolo[1,5-a]pyridin-7-yl)-N-phenyl-benzene-sulfonamide The title compound, MS m/e (%): 430 (M—H$^-$, 100), was prepared in accordance with the general method of example 1 from 3-benzenesulfonylmethyl-5-furan-2-yl-1H-[1,2,4]triazole and 4-(2-cyano-vinyl)-N-phenyl-benzenesulfonamide

EXAMPLE 320

2-Furan-2-yl-7-[4-(4-methyl-piperazine-1-sulfonyl)-phenyl]-[1,2,4]triazolo[1,5-a]pyridin-5-ylamine a) 3-[4-(4-Methyl-piperazine-1-sulfonyl)-phenyl]-acrylonitrile A mixture of 24.1 g (0.068 mol) 1-[(4-bromophenyl)sulfonyl]-4-methyl-piperazine, 5.38 ml acrylonitrile, 18.9 ml (0.26 mol) triethylamine and 0.95 g (0.001 mol) bis(triphenyl-phosphine)palladium(II)chloride in 380 ml dimethylformamide were stirred at 120° C. for 72 hours. The mixture was extracted with saturated aqueous sodiumbicarbonate solution and dried with sodiumsulfate. Chromatography on silicagel with dichloromethane/methanol 98/2 gave 15.2 g (77%) (E)/(Z)-3-[4-(4-methyl-piperazine-1-sulfonyl)-phenyl]-acrylonitrile as a light yellow solid. MS m/e (%/): 292 (M+H$^+$, 100).

b) 2-Furan-2-yl-7-[4-(4-methyl-piperazine-1-sulfonyl)-phenyl -[1,2,4]triazolo[1,5-a]pyridin-5-ylamine The title compound, MS m/e (%): 439 (M+H$^+$, 100), was prepared in accordance with the general method of example 1 from 3-benzenesulfonylmethyl-5-furan-2-yl-1H-[1,2,4]triazole and 3-[4-(4-methyl-piperazine-1-sulfonyl)-phenyl]-acrylonitrile.

EXAMPLE 321

2-(2,4-Difluoro-phenyl)-7-pyridin-4-yl-[1,2,4]triazolo[1,5-a]pyridin-5-ylamine a) 2,4-Difluoro-benzoic acid (1-amino-2-benzenesulfonyl-ethylidene)-hydrazide A suspension of 15.3 g (0.058 mol) 2-(phenylsulfonyl)-ethanimidic acid ethyl ester hydrochloride in 125 ml chloroform was treated with 58.1 ml 1N aqueous sodium hydoxide. 18 ml of a saturated aqueous sodiumbicarbonate solution was added and the mixture was extracted with chloroform. The extracts were combined and dried with sodium sulfate and the solvents were distilled off under reduced pressure. The resulting colorless oil was stirred together with 10.0 g (0.058 mol) 2,4-difluorobenzoic acid hydrazide in 110 ml chloroform over night at 50° C. The resulting precipitate was filtered off and dried. A yield of 8.50 g (42%) 2,4-difluoro-benzoic acid (1-amino-2-benzenesulfonyl-ethylidene)-hydrazide was obtained as white solid. MS m/e (%): 354 (M+H$^+$, 100).

b) 3-Benzenesulfonylmethyl-5-(2,4-difluoro-phenyl)-1H-[1,2,4]triazole 8.0 g (0.023 mol) 2,4-Difluoro-benzoic acid (1-amino-2-benzenesulfonyl-ethylidene)-hydrazide were heated at 210° C. for 20 minutes. The molten mass was then cooled, dissolved in 30 ml hot ethanol and stirred overnight at room temperature. The precipitated crystals were filtered off and dried to yield 5.35 g (71%) 3-benzenesulfonylmethyl-5-(2,4-difluoro-phenyl)-1H-[1,2,4]triazole as white solid, MS m/e (%): 336 (M+H$^+$, 100).

c) 2-(2,4-Difluoro-phenyl)-7-pyridin-4-yl-[1,2,4]triazolo[1,5-a]pyridin-5-ylamine The title compound, MS m/e (%): 323 (M$^+$, 100), 303 (60), was prepared in accordance with the general method of example 1 from 3-benzenesulfonylmethyl-5-(2,4-difluoro-phenyl)-1H-[1,2,4]triazole and (E)/(Z)-3-pyridin-4-yl-acrylonitrile.

EXAMPLE 322

2-(2,4-Difluoro-phenyl)-7-pyridin-2-yl-[1,2,4]triazolo[1,5-a]pyridin-5-ylamine

The title compound, MS m/e (%): 324(M+H$^+$,100), was prepared in accordance with the general method of example 1 from 3-benzenesulfonylmethyl-5-(2,4-difluoro-phenyl)-1H-[1,2,4]triazole and (E)/(Z)-3-pyridin-2-yl-acrylonitrile.

EXAMPLE 323

2-(2-Fluoro-phenyl)-7-pyridin-4-yl-[1,2,4]triazolo[1,5-a]pyridin-5-ylamine a) 2-Fluoro-benzoic acid (1-amino-2-benzenesulfonyl-ethylidene)-hydrazide A suspension of 15.2 g (0.058 mol) 2-(phenylsulfonyl)-ethanimidic acid ethyl ester hydrochloride in 160 ml chloroform was treated with 57.7 ml 1N aqueous sodium hydoxide. 80 ml of a saturated aqueous sodiumbicarbonate solution was added and the mixture was extracted with chloroform. The extracts were combined and dried with sodium sulfate and the solvents were distilled off under reduced pressure. The resulting colorless oil was stirred together with 9.98 g (0.063 mol) 2-fluorobenzoic acid hydrazide in 65 ml chloroform over io night at 50° C. The resulting precipitate was filtered off and dried. A yield of 14.6 g 2-fluoro-benzoic acid (1-amino-2-benzenesulfonyl-ethylidene)-hydrazide was obtained as white solid. MS m/e (%): 336 (M+H$^+$, 100).

b) 3-Benzenesulfonylmethyl-5-(2-fluoro-phenyl)-1H-[1,2,4]triazole 14 g (0.042 mol) 2-fluoro-benzoic acid (1-amino-2-benzenesulfonyl-ethylidene)-hydrazide were heated at 210° C. for 20 minutes. The molten mass was then cooled, dissolved in 40 ml hot ethanol and stirred overnight at room temperature. The precipitated crystals were filtered off and dried to yield 11.4 g (86%) 3-benzenesulfonylmethyl-5-(2-fluoro-phenyl)-1H-[1,2,4]triazole as beige solid, MS m/e (%): 317 (M$^+$, 2), 253(68), 176(100), 122(61).

c) 2-(2-Fluoro-phenyl)-7-pyridin-4-yl-[1,2,4]triazolo[1,5-a]pyridin-5-ylamine

The title compound, MS m/e (%):306(M+H$^+$,100), was prepared in accordance with the general method of example 1 from 3-benzenesulfonylmethyl-5-(2-fluoro-phenyl)-1H-1,2,4]triazole and (E)/(Z)-3-pyridin-4-yl-acrylonitrile.

EXAMPLE 324

2-(2-Fluoro-phenyl)-7-(6-methoxy-pyridin-3-yl)-[1,2,4]triazolo[1,5-a]pyridin-5-ylamine The title compound, MS m/e (%):336(M+H$^+$,100), was prepared in accordance with the general method of example 1 from 3-benzenesulfonylmethyl-5-(2-fluoro-phenyl)-1H-[1,2,4]triazole and (E)/(Z)-3-(6-methoxy-pyridin-3-yl)-acrylonitrile.

EXAMPLE 325

7-(2-Ethyl-pyridin-4-yl)-2-pyridin-2-yl-[1,2,4]triazolo[1,5-a]pyridin-5-ylamine

The title compound, MS m/e (%):316(M$^+$,100), was prepared in accordance with the general method of example 1 from 2-(5-benzenesulfonylmethyl-2H-[1,2,4]triazol-3-yl)-pyridine and (E)-3-(2-ethyl-pyridin-4-yl)-acrylonitrile.

EXAMPLE 326

7-(2-Methyl-pyridin-4-yl)-2-pyridin-2-yl-[1,2,4]triazolo[1,5-a]pyridin-5-ylamine The title compound, MS m/e (%):303 (M+H$^+$,100), was prepared in accordance with the general method of example 1 from 2-(5-benzenesulfonylmethyl-2H-[1,2,4]triazol-3-yl)-pyridine and (E)/(Z)-3-(2-methyl-pyridin-4-yl)-acrylonitrile.

EXAMPLE 327

7-(5-Ethyl-pyridin-2-yl)-2-pyridin-2-yl-[1,2,4]triazolo[1,5-a]pyridin-5-ylamine a) (E)/(Z)-3-(5-Ethyl-pyridin-2-yl)-acrylonitrile (E)/(Z)-3-(5-Ethyl-pyridin-2-yl)-acrylonitrile was obtained from 5-ethyl-2-pyridine-carboxaldehyde and (cyanomethyl)triphenylphosphonium chloride/sodiumhydride in THF as a liquid, MS m/e (%):158(M$^+$, 100).

b) 7-(5-Ethyl-pyridin-2-yl)-2-pyridin-2-yl-[1,2,4]triazolo[1,5-a]pyridin-5-ylamine The title compound, MS m/e (%):317 (M+H$^+$,100), was prepared in accordance with the general method of example 1 from 2-(5-benzenesulfonylmethyl-2H-[1,2,4]triazol-3-yl)-pyridine and (E)/(Z)-3-(5-ethyl-pyridin-2-yl)-acrylonitrile.

EXAMPLE 328

2,7-Di-pyridin-2-yl-[1,2,4]triazolo[1,5-a]pyridin-5-ylamine

The title compound, MS m/e (%):289 (M+H$^+$,100), was prepared in accordance with the general method of example 1 from 2-(5-benzenesulfonylmethyl-2H-[1,2,4]triazol-3-yl)-pyridine and (E)/(Z)-3-pyridin-2-yl-acrylonitrile.

EXAMPLE 329

2-Pyridin-2-yl-7-pyridin-3-yl-[1,2,4]triazolo[1,5-a]pyridin-5-ylamine

The title compound, MS m/e (%):288 (M$^+$,100), was prepared in accordance with the general method of example 1 from 2-(5-benzenesulfonylmethyl-2H-[1,2,4]triazol-3-yl)-pyridine and (E)/(Z)-3-pyridin-3-yl-acrylonitrile.

EXAMPLE 330

2-Pyridin-3-yl-7-pyridin-2-yl-[1,2,4]triazolo[1,5-a]pyridin-5-ylamine a) Nicotinic acid (1-amino-2-benzenesulfonyl-ethylidene)-hydrazide A suspension of 23.6 g (0.089 mol) 2-(phenylsulfonyl)-ethanimidic acid ethyl ester hydrochloride in 300 ml chloroform was treated with 98 ml 1N aqueous sodium hydoxide. 200 ml of a saturated aqueous sodiumbicarbonate solution was added and the mixture was extracted with chloroform. The extracts were combined and dried with sodium sulfate and the solvents were distilled off under reduced pressure. The resulting colorless oil was stirred together with 13.5 g (0.098 mol) nicotinic acid hydrazide in 500 ml dioxane over night at 50° C. The resulting precipitate was filtered off and dried. A yield of 15.5 g (55%) nicotinic acid (1-amino-2-benzenesulfonyl-ethylidene)-hydrazide was obtained as white solid, MS m/e (%): 319 (M+H$^+$, 100).

b) 3-(5-Benzenesulfonylmethyl-2H-[1,2,4]triazol-3-yl)-pyridine 15.0 g (0.047 mol) nicotinic acid (1-amino-2-benzenesulfonyl-ethylidene)-hydrazide were heated at 220° C. for 20 minutes. The molten mass was then cooled, dissolved in 100 ml hot ethanol and stirred overnight at room temperature. The precipitated crystals were filtered off and dried to yield 13.6 g (96%)) 3-(5-benzenesulfonylmethyl-2H-[1,2,4]triazol-3-yl)-pyridine as white solid, MS m/e (%): 300 (M$^+$, 8), 236(99), 159 (100), 105(43), 77(35).

c) 2-Pyridin-3-yl-7-pyridin-2-yl-[1,2,4]triazolo-[1,5-a]pyridin-5-ylamine

The title compound, MS m/e (%):289 (M+H$^+$,100), was prepared in accordance with the general method of example 1 from 3-(5-benzenesulfonylmethyl-2H-[1,2,4]triazol-3-yl)-pyridine and (E)/(Z)-2-pyridin-2-yl-acrylonitrile.

EXAMPLE 331

7-(5-Chloro-pyridin-2-yl)-2-pyridin-2-yl-[1,2,4]triazolo[1,5-a]pyridin-5-ylamine a) 3-(5-Chloro-pyridin-2-yl)-acrylonitrile 3-(5-Chloro-pyridin-2-yl)-acrylonitrile was obtained from 5-chloro-picolinaldehyde and diethyl cyanomethyl-phosphonate/sodiumhydride in THF as a white solid, MS m/e (%):164 (M+,100), 137(17), 113(45).

b) 7-(5-Chloro-pyridin-2-yl)-2-pyridin-2-yl-[1,2,4]triazolo[1,5-a]pyridin-5-ylamine The title compound, MS m/e (%):323 (M+H+,100), was prepared in accordance with the general method of example 1 from 2-(5-benzenesulfonylmethyl-2H-[1,2,4]triazol-3-yl)-pyridine and (E)/(Z)-3-(5-chloro-pyridin-2-yl)-acrylonitrile.

EXAMPLE 332

7-(6-Chloro-pyridin-3-yl)-2-pyridin-2-yl-[1,2,4]triazolo[1,5-a]pyridin-5-ylamine The title compound, MS m/e (%):323 (M+H+,100), was prepared in accordance with the general method of example 1 from 2-(5-benzenesulfonylmethyl-2H-[1,2,4]triazol-3-yl)-pyridine and (E)/(Z)-3-(6-chloro-pyridin-3-yl)-acrylonitrile.

EXAMPLE 333

7-(6-Morpholin-4-yl-pyridin-3-yl)-2-pyridin-2-yl-[1,2,4]triazolo[1,5-a]pyridin

A solution of 0.10 g (0.0003 mol) 7-(6-chloro-pyridin-3-yl)-2-pyridin-2-yl-[1,2,4]triazolo[1,5-a]pyridin-5-ylamine in 15 ml morpholine were stirred at 130° C. for 4 hours. Removal of the amine and chromatography on silicagel with dichloromethane/methanol 9/1 gave 0.07 g (62%) 7-(6-morpholin-4-yl-pyridin-3-yl)-2-pyridin-2-yl-[1,2,4]triazolo[1,5-a]pyridin beige solid, MS m/e (%):374 (M+H+,100).

EXAMPLE 334

7-(6-Isopropylamino-pyridin-3-yl)-2-pyridin-2-yl-[1,2,4]triazolo[1,5-a]pyridin-5-ylamine A solution of 0.16 g (0.00035 mol) 7-(6-chloro-pyridin-3-yl)-2-pyridin-2-yl-[1,2,4]triazolo[1,5-a]pyridin-5-ylamine in 80 ml isopropylamine were stirred at 150° C. for 150 hours in an autoclav. Removal of the amine and chromatography on silicagel with dichloro-methane/methanol 9/1 gave 0.05 g (29%) 7-(6-isopropylamino-pyridin-3-yl)-2-pyridin-2-yl-[1,2,4]triazolo[1,5-a]pyridin-5-ylamine as beige solid, MS m/e (%): 346 (M+H+,100).

EXAMPLE 335

7-(6-Ethylamino-pyridin-3-yl)-2-pyridin-2-yl-[1,2,4]triazolo[1,5-a]pyridin-5-ylamine The title compound, MS m/e (%):331 (M+,100). was prepared from 7-(6-chloro-pyridin-3-yl)-2-pyridin-2-yl-[1,2,4]triazolo[1,5-a]pyridin-5-ylamine and ethylamine as described for the previous example 334.

EXAMPLE 336

7-(6-Chloro-pyridin-2-yl)-2-pyridin-2-yl-[1,2,4]triazolo[1,5-a]pyridin-5-ylamine a) E-3-(6-Chloro-pyridin-2-yl)-acrylonitrile E-3-(6-Chloro-pyridin-2-yl)-acrylonitrile was obtained from 6-chloro-2-pyridine-carboxaldehyde and diethyl cyanomethyl-phosphonate/sodiumhydride in THF as a white solid, MS m/e (%):164(M+,100), 137(14),113(75).

b) 7-(6-Chloro-pyridin-2-yl)-2-pyridin-2-yl-[1,2,4]triazolo[1,5-a]pyridin-5-ylamine The title compound, MS m/e (%):323 (M+H+,100), was prepared in accordance with the general method of example 1 from 2-(5-benzenesulfonylmethyl-2H-[1,2,4]triazol-3-yl)-pyridine and E-3-(6-chloro-pyridin-2-yl )-acrylonitrile.

EXAMPLE 337

7-(6-Ethylamino-pyridin-2-yl)-2-pyridin-2-yl-[1,2,4]triazolo[1,5-a]pyridin-5-ylamine The title compound, MS m/e (%):331 (M+,100). was prepared from 7-(6-chloro-pyridin-2-yl)-2-pyridin-2-yl-[1,2,4]triazolo[1,5-a]pyridin-5-ylamine and ethylamine as described for the example 334.

EXAMPLE 338

2-Methylsulfanyl-7-pyridin-2-yl-[1,2,4]triazolo[1,5-a]pyridin-5-ylamine a) 1-[[1-Amino-2-(phenylsulfonyl)ethylidene]amino]-2-methyl-2-thiopseudourea (or tautomer)

A suspension of 211 g (0.80 mol) 2-(phenylsulfonyl)-ethanimidic acid ethyl ester hydrochloride in 2 l chloroform was treated with 801 ml 1N aqueous sodium hydoxide. 350 ml of a saturated aqueous sodiumbicarbonate solution was added and the mixture was extracted with chloroform. The extracts were combined and dried with sodium sulfate and the solvents were distilled off under reduced pressure. The resulting oil was dissolved in 450 ml ethanol and the solution was added to a suspension of 44.6 g (0.82 mol) sodiummethylate and 187 g (0.80 mol) methyl aminomethanehydrazonothioate hydroiodide. After 75 minutes at room temperature 4.8 l of a 3/1 water/saturated aqueous sodiumbicarbonate solution was added and the mixture was extracted with chloroform. The organic phase was dried with sodiumsulfate and the solvents were evaporated. Recrystallisation from 1.81 ethanol gave 121 g (53%) 1-[[1-amino-2-(phenylsulfonyl)ethylidene]amino]-2-methyl-2-thiopseudourea (or tautomer), MS m/e (%): 287 (M+H+, 100), 270 (28).

b) 3-Benzenesulfonylmethyl-5-methylsulfanyl-1H-[1,2,4]triazole 83.0 g (0.29 mol) 1-[[1-Amino-2-(phenylsulfonyl)ethylidene]amino]-2-methyl-2-thiopseudourea in 830 ml 1N HCl were refluxed for 30 minutes. After cooling the product crystallised. It was filtered off, washed with water and dried at 50° C./vacuum.Yield: 67.4 g (86%), white solid with melting point 160–161° C.

c) 2-Methylsulfanyl-7-pyridin-2-yl-[1,2,4]triazolo[1,5-a]pyridin-5-ylamine

The title compound, MS m/e (%):258 (M+H+,100), was prepared in accordance with the general method of example 1 from 3-benzenesulfonylmethyl-5-methylsulfanyl-1H-[1,2,4]triazole and (E)/(Z)-3-pyridin-2-yl-acrylonitrile.

EXAMPLE 339

2-Pyrazol-1-yl-7-pyridin-2-yl-[1,2,4]triazolo[1,5-a]
pyridin-5-ylamine a) 2-Methanesulfinyl-7-pyridin-2-yl-[1,2,4]triazolo[1,5-a]
pyridin-5-ylamine 8.66 g (0.034 mol) 2-Methylsulfanyl-7-pyridin-2-yl-[1,2,4]triazolo[1,5-a]pyridin-5-ylamine in 850 ml dichloromethane were oxidised with a solution of 17.6 g (0.067 mol) 3-phenyl-2-(phenylsulfonyl)oxaziridine in 150 ml dichloromethane overnight. Chromatography on aluminiumoxide (dichloromethane/ methanol 97:3) and on silicagel (ethylacetate/methanol 9:1) yielded 5.2 g (57%) 2-methanesulfinyl-7-pyridin-2-yl-[1,2,4]triazolo[1,5-a]pyridin-5-ylamine, MS m/e (%):274 (M+H$^+$,100).

b) 2-Pyrazol-1-yl-7-pyridin-2-yl-1,2,4]triazolo[1,5-a]
pyridin-5-ylamine

A mixture of 0.50 g (0.002 mol) 2-methanesulfinyl-7-pyridin-2-yl-[1,2,4]triazolo[1,5-a]pyridin-5-ylamine and 0.33 ml (0.002 mol) 1,8-diazabicyclo[5.4.0]undec-7-en in 12.5 g molten pyrazole as solvent was stirred overnight at 120° C. Destillation of the solvent and chromatography on silicagel with ethylacetate/methanol 95/5 gave 0.13 g (26%) 2-pyrazol-1-yl-7-pyridin-2-yl-[1,2,4]triazolo[1,5-a]pyridin-5-ylamine as a white solid, MS m/e (%):278 (M+H$^+$,100).

EXAMPLE 340

7-Pyridin-2-yl-2-[1,2,4]triazol-1-yl-[1,2,4]triazolo[1,
5-a]pyridin-5-ylamine

The title compound, MS m/e (%):279 (M+H$^+$,100), was prepared in accordance with the method of example 339b) from 2-methanesulfinyl-7-pyridin-2-yl-[1,2,4]triazolo[1,5-a]pyridin-5-ylamine and 1,8-diazabicyclo[5.4.0]undec-7-en in 1,2,4-triazole at 130° C.

EXAMPLE 341

2-(2-Methyl-imidazol-1-yl)-7-pyridin-2-yl-[1,2,4]
triazolo[1,5-a]pyridin-5-ylamine The title compound, MS m/e (%):292 (M+H$^+$,100), was prepared in accordance with the method of example 339b) from 2-methanesulfinyl-7-pyridin-2-yl-[1,2,4]triazolo[1,5-a]pyridin-5-ylamine and 1,8-diazabicyclo[5.4.0]undec-7-en in 2-methylimidazole at 170° C.

EXAMPLE 342

2-Phenethyloxy-7-pyridin-2-yl-[1,2,4]triazolo[1,5-a]
pyridin-5-ylamine 0.06 g (0.003 mol) sodium in 50 ml 2-phenylethanol were stirred overnight at 60° C. 0.2 g (0.0007 mol) 2-methanesulfinyl-7-pyridin-2-yl-[1,2,4]triazolo[1,5-a]pyridin-5-ylamine added and stirring was continued at 160° C. for 16 hours. Evaporation of the solvent and chromatography on silicagel with ethylacetate gave 0.2 g (83%) 2-phenethyloxy-7-pyridin-2-yl-[1,2,4]triazolo[1,5-a]pyridin-5-ylamine, MS m/e (%):332 (M+H$^+$,100).

EXAMPLE 343

2-Pyridin-2-yl-7-thiophen-3-yl-[1,2,4]triazolo[1,5-a]
pyridin-5-ylamine

The title compound, MS m/e (%):294 (M+H$^+$,100). was prepared according to the procedure of example 92 from 7-bromo-2-pyridin-2-yl-[1,2,4]triazolo[1,5-a]pyridin-5-ylamine and 3-thiophenboronic acid.

EXAMPLE 344

2-Pyrazol-1-yl-7-pyridin-3-yl-[1,2,4]triazolo[1,5-a]
pyridin-5-ylamine a) 2-Methylsulfanyl-7-pyridin-3-yl-[1,2,4]triazolo[1,5-a]
pyridin-5-ylamine 2-Methylsulfanyl-7-pyridin-3-yl-[1,2,4]triazolo[1,5-a]pyridin-5-ylamine, a white solid with melting point 161–163° C., was prepared in accordance with the general method of example 1 from 3-benzenesulfonylmethyl-5-methylsulfanyl-1H-[1,2,4]triazole and (E)/(Z)-3-pyridin-3-yl-acrylonitrile.

b) 2-Methanesulfinyl-7-pyridin-3-yl-[1,2,4]triazolo[1,5-a]
pyridin-5-ylamine

2-Methanesulfinyl-7-pyridin-3-yl-[1,2,4]triazolo[1,5-a]pyridin-5-ylamine, MS m/e (%):274 (M+H$^+$,100), was prepared in accordance with the method of example 339a) from 2-methylsulfanyl-7-pyridin-3-yl-[1,2,4]triazolo[1,5-a]pyridin-5-ylamine and 3-phenyl-2-(phenylsulfonyl) oxaziridine.

c) 2-Pyrazol-1-yl-7-pyridin-3-yl-[1,2,4]triazolo[1,5-a]
pyridin-5-ylamine

The title compound, MS m/e (%):277 (M$^+$,100), was prepared in accordance with the method of example 339b) from 2-methanesulfinyl-7-pyridin-3-yl—([1,2,4]triazolo[1,5-a]pyridin-5-ylamine and 1,8-diazabicyclo[5.4.0]undec-7-en in pyrazole at 75° C.

EXAMPLE 345

8-Benzenesulfonyl-2-furan-2-yl-[1,2,4]triazolo[1,5-
a]pyridin-5-ylamine

The title compound, MS m/e (%): 341 (M+H$^+$, 100), was prepared in accordance with the general method of example 1 from 3-benzenesulfonylmethyl -5-furan-2-yl-1H-[1,2,4]triazole and 3-methoxy-2-propenitrile.

EXAMPLE 346

8-Benzenesulfonyl-2-pyridin-2-yl-[1,2,4]triazolo[1,
5-a]pyridin-5-ylamine

The title compound, MS m/e (%): 351 (M$^+$, 92), 286(100), 171(54), was prepared in accordance with the general method of example 1 from 2-(5-benzenesulfonylmethyl-2H-[1,2,4]triazol-3-yl)-pyridine and 3-methoxy-2-propenitrile.

EXAMPLE 347

5-Amino-2-phenyl-[1,2,4]triazolo[1,5-a]pyridine-8-
carbonitrile

The title compound, MS m/e (%): 235 (M$^+$, 100), 208(10), 104(16), was prepared in accordance with the general method of example 1 from (5-phenyl-2H-[1,2,4]triazol-3-yl)-acetonitrile and 3-methoxy-2-propenitrile.

EXAMPLE 348

2-[1-(2,7-di-pyridin-2-yl-[1,2,4]triazolo[1,5-a]
pyridin-5-yl)-1,4,5,6-tetrahydro-pyrimidin-2-yl]-
benzoic acid The title compound, ms m/e (%): 476 (M+H$^+$, 100), was prepared in accordance with the general method of example 27 from 2,7-di-pyridin-2-yl-[1,2,4]triazolo[1,5-a]pyridin-5-ylamine and N-(3-bromopropyl)-phthalimide.

What is claimed is:
1. A compound of the formula

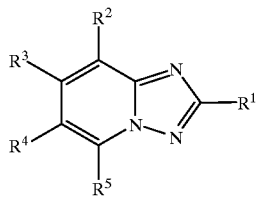

I wherein
$R^1$ is fur-2yl, lower alkyl substituted fur-2yl, pyridin-2yl, (4,5)dihydrofur-2yl, 2-pyrazol-1yl or phenyl;
$R^2$ and $R^4$ are hydrogen;
$R^3$ is pyridin-2yl, pyridin-3yl, or pyridin-4yl, wherein said pyridinyl moieties are unsubstituted or substituted by one or two substituents selected from the group consisting of oxo, lower alkyl, halogen and lower alkoxy; or
unsubstituted pyranyl, unsubstituted indolyl or unsubstituted thiophen; or
unsubstituted phenyl or phenyl substituted by one or two substituents selected from the group consisting of trifluoromethyl, lower alkoxy, lower thioalkyl, —NH—C(O)-lower alkyl, —NH$_2$, —C(O)—CH$_3$ and —NH(CH$_2$)$_n$-phenyl, wherein said phenyl is substituted by one or two substituents selected from the group consisting of halogen or lower alkoxy;
$R_5$ is —NH$_2$, —N(lower alkyl)$_2$, —NH(lower alkyl), —NH—CH$_2$—CH=CH$_2$—, —NHC(O)O-lower alkyl, —NH—C(O)(CH$_2$)$_n$-phenyl, wherein said phenyl is substituted by one or two substituents selected from the group consisting of halogen and —CF$_3$; and
n is 0, 1 or 2 or a
pharmaceutically acceptable salt thereof.
2. A compound according to claim 1, wherein $R^5$ is an unsubstituted amino group.
3. A compound according to claim 2, wherein $R^1$ is furyl.
4. A compound according to claim 3, which is 2-furan-2-yl-7-pyridin-4-yl-[1,2,4]triazolo[1,5-a]pyridin-5-ylamine.
5. A compound according to claim 3 which is 2-furan-2-yl-7-pyridin-3-yl-[1,2,4]triazolo[1,5-a]pyridin-5-ylamine.
6. A compound according to claim 3, which is 2-furan-2-yl-7-pyridin-2-yl-[1,2,4]triazolo[1,5-a]pyridin-5-ylamine.
7. A compound according to claim 3, which is 7-(3,5-bis-trifluoromethyl-phenyl)-2-furan-2-yl-[1,2,4]triazolo[1,5-a]pyridin-5-ylamine.
8. A compound according to claim 3, which is 7-(3,5-dichloro-phenyl)-2-furan-2-yl-[1,2,4]triazolo[1,5-a]pyridin-5-ylamine.
9. A compound according to claim 3, which is 7-(4-chloro-phenyl)-2-furan-2-yl-[1,2,4]triazolo[1,5-a]pyridin-5-ylamine.
10. A compound according to claim 3, which is 2-furan-2-yl-7-(2-methyl-pyridin-4-yl)-[1,2,4]triazolo[1,5-a]pyridin-5-ylamine.
11. A compound according to claim 3, which is 7-(2-ethyl-pyridin-4-yl)-2-furan-2-yl-[1,2,4]triazolo[1,5-a]pyridin-5-ylamine.
12. A compound according to claim 3, which is 2-furan-2-yl-7-(2-propyl-pyridin-4-yl)-[1,2,4]triazolo[1,5-a]pyridin-5-ylamine.
13. A compound according to claim 3, which is 2-furan-2-yl-7-(2-isopropyl-pyridin-4-yl)-[1,2,4]triazolo[1,5-a]pyridin-5-ylamine.
14. A compound according to claim 3, which is 7-(4-fluoro-phenyl)-2-furan-2-yl-[1,2,4]triazolo[1,5-a]pyridin-5-ylamine.
15. A compound according to claim 3, which is 2-furan-2-yl-7-(1-oxy-pyridin-4-yl)-[1,2,4]triazolo[1,5-a]pyridin-5-ylamine.
16. A compound according to claim 3, which is 5-amino-2-furan-2-yl-7-pyridin-4-yl-[1,2,4]triazolo[1,5-a]pyridine-6-carbonitrile.
17. A compound according to claim 3, which is 7-(3-amino-phenyl)-2-furan-2-yl-[1,2,4]triazolo[1,5-a]pyridin-5-ylamine.
18. A compound according to claim 3, which is 7-(3,4-dimethoxy-phenyl)-2-furan-2-yl-[1,2,4]triazolo[1,5-a]pyridin-5-ylamine.
19. A compound according to claim 3, which is 7-(3,4-dichloro-phenyl)-2-furan-2-yl-[1,2,4]triazolo[1,5-a]pyridin-5-ylamine.
20. A compound according to claim 3, which is 7-(3-fluoro-phenyl)-2-furan-2-yl-[1,2,4]triazolo[1,5-a]pyridin-5-ylamine.
21. A compound according to claim 3, which is 1-[3-(5-amino-2-furan-2-yl-[1,2,4]triazolo[1,5-a]pyridin-7-yl)-phenyl]-ethanone.
22. A compound according to claim 3, which is 7-(2-fluoro-phenyl)-2-furan-2-yl-[1,2,4]triazolo[1,5-a]pyridin-5-ylamine.
23. A compound according to claim 3, which is 2-furan-2-yl-7-m-tolyl-[1,2,4]triazolo[1,5-a]pyridin-5-ylamine.
24. A compound according to claim 3, which is 2-furan-2-yl-7-(4-methylsulfanyl-phenyl)-[1,2,4]triazolo[1,5-a]pyridin-5-ylamine.
25. A compound according to claim 3, which is 2-furan-2-yl-7-thiophen-3-yl-[1,2,4]triazolo[1,5-a]pyridin-5-ylamine.
26. A compound according to claim 3, which is 2-furan-2-yl-7-(3-trifluoromethyl-phenyl)-[1,2,4]triazolo[1,5-a]pyridin-5-ylamine.
27. A compound according to claim 3, which is 2-furan-2-yl-7-(3-methoxy-phenyl)-[1,2,4]triazolo[1,5-a]pyridin-5-ylamine.
28. A compound according to claim 3, which is N-[3-(5-amino-2-furan-2-yl-[1,2,4]triazolo[1,5-a]pyridin-7-yl)-phenyl]-acetamide.
29. A compound according to claim 3, which is 2-furan-2-yl-7-(1H-indol-5-yl)-[1,2,4]triazolo[1,5-a]pyridin-5-ylamine.
30. A compound according to claim 3, which is N-[4-(5-amino-2-furan-2-yl-[1,2,4]triazolo[1,5-a]pyridin-7-yl)-2-methyl-phenyl]-acetamide.
31. A compound according to claim 3, which is 2-furan-2-yl-7-pyrrolidin-1-yl-[1,2,4]triazolo[1,5-a]pyridin-5-ylamine.
32. A compound according to claim 3, which is N7-(2-chloro-benzyl)-2-furan-2-yl-[1,2,4]triazolo[1,5-a]pyridine-5,7-diamine.
33. A compound according to claim 3, which is 2-furan-2-yl-N7-(2-methoxy-benzyl)-[1,2,4]triazolo[1,5-a]pyridine-5,7-diamine.
34. A compound according to claim 3, which is 2-furan-2-yl-N7-(1-phenyl-ethyl)-[1,2,4]triazolo[1,5-a]pyridine-5,7-diamine.
35. A compound according to claim 3, which is 7-(5-butyl-pyridin-2-yl)-2-furan-2-yl-[1,2,4]triazolo[1,5-a]pyridin-5-ylamine.
36. A compound according to claim 3, which is 7-(2-fluoro-pyridin-4-yl)-2-furan-2-yl-[1,2,4]triazolo[1,5-a]pyridin-5-ylamine.

37. A compound according to claim 3, which is 7-(5-chloro-pyridin-2-yl)-2-furan-2-yl-[1,2,4]triazolo[1,5-a]pyridin -5-ylamine.

38. A compound according to claim 3, which is 2-furan-2-yl-7-(6-methoxy-pyridin-3-yl)-[1,2,4]triazolo[1,5-a]pyridin-5-ylamine.

39. A compound according to claim 2, wherein $R^1$ is methyl substituted furyl.

40. A compound according to claim 39, which is 7-(4-chloro-phenyl)-2-(5-methyl-furan-2-yl)-[1,2,4]triazolo[1,5-a]pyridin-5-ylamine.

41. A compound according to claim 39, which is 7-(3-methoxy-phenyl)-2-(5-methyl-furan-2-yl)-[1,2,4]triazolo[1,5-a]pyridin-5-ylamine.

42. A compound according to claim 39, which is 7-(3,4-dimethoxy-phenyl)-2-(5-methyl-furan-2-yl)-[1,2,4]triazolo[1,5-a]pyridin-5-ylamine.

43. A compound according to claim 39, which is N-{3-[5-amino-2-(5-methyl-furan-2-yl)-[1,2,4]triazolo[1,5-a]pyridin-7-yl]-phenyl}-acetamide.

44. A compound according to claim 39, which is N-{4-[5-amino-2-(5-methyl-furan-2-yl)-[1,2,4]triazolo[1,5-a]pyridin-7-yl]-phenyl}-acetamide.

45. A compound according to claim 2, wherein $R^1$ is pyridin-2-yl.

46. A compound according to claim 45, which is 7-(4-fluoro-phenyl)-2-pyridin-2-yl-[1,2,4]triazolo[1,5-a]pyridin-5-ylamine.

47. A compound according to claim 45, which is 7-(3-methoxy-phenyl)-2-pyridin-2-yl-[1,2,4]triazolo[1,5-a]pyridin-5-ylamine.

48. A compound according to claim 45, which is 7-(3-amino-phenyl)-2-pyridin-2-yl -[1,2,4]triazolo[1,5-a]pyridin-5-ylamine.

49. A compound according to claim 45, which is 7-(2-ethyl-pyridin-4-yl)-2-pyridin-2-yl-[1,2,4]triazolo[1,5-a]pyridin-5-ylamine.

50. A compound according to claim 45, which is 7-(2-methyl-pyridin-4-yl)-2-pyridin-2-yl-[1,2,4]triazolo[1,5-a]pyridin-5-ylamine.

51. A compound according to claim 45, which is 7-(5-ethyl-pyridin-2-yl)-2-pyridin-2-yl-[1,2,4]triazolo[1,5-a]pyridin-5-ylamine.

52. A compound according to claim 45, which is 2,7-di-pyridin-2-yl-[1,2,4]triazolo[1,5-a]pyridin-5-ylamine.

53. A compound according to claim 45, which is 7-(5-chloro-pyridin-2-yl)-2-pyridin-2-yl-[1,2,4]triazolo[1,5-a]pyridin-5-ylamine.

54. A compound according to claim 45, which is 7-(6-chloro-pyridin-2-yl)-2-pyridin-2-yl-[1,2,4]triazolo[1,5-a]pyridin-5-ylamine.

55. A compound according to claim 2, wherein $R^1$ is 4,5-dihydro-furan-2-yl.

56. A compound according to claim 55, which is 7-(3,4-dichloro-phenyl)-2-(4,5-dihydro-furan-2-yl)-[1,2,4]triazolo[1,5-a]pyridin-5-ylamine.

57. A compound according to claim 55, which is 2-(4,5-dihydro-furan-2-yl)-7-(3-fluoro-phenyl)-[1,2,4]triazolo[1,5-a]pyridin-5-ylamine.

58. A compound according to claim 55, which is 2-(4,5-dihydro-furan-2-yl)-7-(4-fluoro-phenyl)-[1,2,4]triazolo[1,5-a]pyridin-5-ylamine.

59. A compound according to claim 55, which is 2-(4,5-dihydro-furan-2-yl)-7-m-tolyl-[1,2,4]triazolo[1,5-a]pyridin-5-ylamine.

60. A compound according to claim 55, which is 2-(4,5-dihydro-furan-2-yl)-7-(3-trifluoromethyl-phenyl)-[1,2,4]triazolo[1,5-a]pyridin-5-ylamine.

61. A compound according to claim 2, wherein $R^1$ is pyrazol-1-yl.

62. A compound according to claim 61, which is 2-pyrazol-1-yl-7-pyridin-2-yl-[1,2,4]triazolo[1,5-a]pyridin-5-ylamine.

63. A compound according to claim 1, wherein $R^5$ is a substituted amino group.

64. A compound according to claim 63, wherein $R^1$ is phenyl.

65. A compound according to claim 64, which is but-3-enyl—(2-phenyl-7-pyridin-4-yl-[1,2,4]triazolo[1,5-a]pyridin-5-yl)-amine.

66. A compound according to claim 64, which is ethyl-(2-phenyl-7-pyridin-4-yl-[1,2,4]triazolo[1,5-a]pyridin-5-yl)-amine.

67. A compound according to claim 64, which is (2-phenyl-7-pyridin-4-yl-[1,2,4]triazolo[1,5-a]pyridin-5-yl)-carbamic acid ethyl ester.

68. A compound according to claim 64, which is N-(2-phenyl-7-pyridin-4-yl-[1,2,4]triazolo[1,5-a]pyridin-5-yl)-4-trifluoromethyl-benzamide.

69. A compound according to claim 64, which is 2-(2-chloro-phenyl)-N-(2-phenyl-7-pyridin-4-yl-[1,2,4]triazolo[1,5-a]pyridin-5-yl)-acetamide.

70. A compound according to claim 64, which is 2-(2,4-dichloro-phenyl)-N-(2-phenyl-7-pyridin-4-yl-[1,2,4]triazolo[1,5-a]pyridin-5-yl)-acetamide.

71. A compound according to claim 64, which is N-(2-phenyl-7-pyridin-4-yl-[1,2,4]triazolo[1,5-a]pyridin-5-yl)-2-(2-trifluoromethyl-phenyl)-acetamide.

72. A compound according to claim 64, which is N-(2-phenyl-7-pyridin-4-yl-[1,2,4]triazolo[1,5-a]pyridin-5-yl)-2-(4-trifluoromethyl-phenyl)-acetamide.

73. A compound according to claim 64, which is 3-phenyl-N-(2-phenyl-7-pyridin-4-yl-[1,2,4]triazolo[1,5-a]pyridin-5-yl)-propionamide.

74. A compound according to claim 64, which is N-(2-phenyl-7-pyridin-4-yl-[1,2,4]triazolo[1,5-a]pyridin-5-yl)-2-o-tolyl-acetamide.

75. A compound according to claim 64, which is 2-(2-bromo-phenyl)-N-(2-5 phenyl-7-pyridin-4-yl-[1,2,4]triazolo[1,5-a]pyridin-5-yl)-acetamide.

76. A compound according to claim 64, which is 2-(2-iodo-phenyl)-N-(2-phenyl-7-pyridin-4-yl-[1,2,4]triazolo[1,5-a]pyridin-5-yl)-acetamide.

77. A compound according to claim 64, which is 3-(2-phenyl-7-pyridin-4-yl-[1,2,4]triazolo[1,5-a]pyridin-5-ylcarbamoyl)-propyl]-carbamic acid tert-butyl ester.

78. A compound according to claim 64, which is 2-(2-chloro-phenyl)-ethyl]-(2-phenyl-7-pyridin-4-yl-[1,2,4]triazolo[1,5-a]pyridin-5-yl)-amine.

79. A compound according to claim 64, which is 2-(2,4-dichloro-phenyl)-ethyl]-(2-phenyl-7-pyridin-4-yl-[1,2,4]triazolo[1,5-a]pyridin-5-yl)-amine.

80. A compound according to claim 64, which is (2-phenyl-7-pyridin-4-yl-[1,2,4]triazolo[1,5-a]pyridin-5-yl)-(4-trifluoromethyl-benzyl)-amine.

81. A compound according to claim 64, which is (3-phenyl-propyl)-(2-phenyl-7-pyridin-4-yl-[1,2,4]triazolo[1,5-a]pyridin-5-yl)-amine.

82. A compound according to claim 64, which is diethyl-(2-phenyl-7-pyridin-4-yl-[1,2,4]triazolo[1,5-a]pyridin-5-yl)-amine.

83. A compound according to claim 63, which is N-[2-(5-Methyl-furan-2-yl)-7-pyridin-4-yl-[1,2,4]triazolo[1,5-a]pyridin-5-yl]-acetamide.

84. A composition containing a compound according to claim 64, and a pharmaceutically acceptable carrier.

* * * * *

UNITED STATES PATENT AND TRADEMARK OFFICE
CERTIFICATE OF CORRECTION

PATENT NO. : 6,355,653 B1
DATED : March 12, 2002
INVENTOR(S) : Gerda H. Trattmann et al.

It is certified that error appears in the above-identified patent and that said Letters Patent is hereby corrected as shown below:

<u>Column 158,</u>
Line 39, delete "5" after "(2-" and before "phenyl".
Line 65, delete "64" and insert -- 1 --.

Signed and Sealed this

First Day of April, 2003

JAMES E. ROGAN
*Director of the United States Patent and Trademark Office*